US008007995B2

(12) United States Patent
Finn et al.

(10) Patent No.: US 8,007,995 B2
(45) Date of Patent: Aug. 30, 2011

(54) MOESIN, CAVEOLIN 1 AND YES ASSOCIATED PROTEIN 1 AS PREDICTIVE MARKERS OF RESPONSE TO DASATINIB IN BREAST CANCERS

(75) Inventors: Richard S. Finn, Encino, CA (US); Judy Dering, Westlake Village, CA (US); Dennis J. Slamon, Woodland Hills, CA (US); Charles L. Ginther, Los Angeles, CA (US); Edwin A. Clark, Pennington, NJ (US)

(73) Assignees: Bristol-Myers Squibb Company, Princeton, NJ (US); The Regents of the University of California, Oakland, CA (US)

( * ) Notice: Subject to any disclaimer, the term of this patent is extended or adjusted under 35 U.S.C. 154(b) by 164 days.

(21) Appl. No.: 12/093,042

(22) PCT Filed: Nov. 10, 2006

(86) PCT No.: PCT/US2006/060776
§ 371 (c)(1),
(2), (4) Date: Oct. 29, 2008

(87) PCT Pub. No.: WO2007/059430
PCT Pub. Date: May 24, 2007

(65) Prior Publication Data
US 2009/0170866 A1 Jul. 2, 2009

Related U.S. Application Data

(60) Provisional application No. 60/735,475, filed on Nov. 10, 2005.

(51) Int. Cl.
*C12Q 1/00* (2006.01)
*C12Q 1/68* (2006.01)
*G01N 33/53* (2006.01)
*G01N 33/574* (2006.01)

(52) U.S. Cl. ............... 435/4; 435/6; 435/7.1; 435/7.21; 435/7.23

(58) Field of Classification Search .................. None
See application file for complete search history.

(56) References Cited

U.S. PATENT DOCUMENTS

| | | | |
|---|---|---|---|
| 4,275,149 A | 6/1981 | Litman et al. | |
| 4,318,980 A | 3/1982 | Boguslaski et al. | |
| 4,736,866 A | 4/1988 | Leder et al. | |
| 4,737,456 A | 4/1988 | Weng et al. | |
| 4,870,009 A | 9/1989 | Evans et al. | |
| 5,242,828 A | 9/1993 | Bergstrom et al. | |
| 5,382,510 A | 1/1995 | Levine et al. | |
| 5,428,130 A | 6/1995 | Capon et al. | |
| 5,667,171 A | 9/1997 | Fowell et al. | |
| 5,720,954 A | 2/1998 | Hudziak et al. | |
| 5,725,856 A | 3/1998 | Hudziak et al. | |
| 5,770,195 A | 6/1998 | Hudziak et al. | |
| 5,772,997 A | 6/1998 | Hudziak et al. | |
| 5,952,170 A | 9/1999 | Stroun et al. | |
| 6,165,464 A | 12/2000 | Hudziak et al. | |
| 6,225,047 B1 | 5/2001 | Hutchens et al. | |
| 6,329,209 B1 | 12/2001 | Wagner et al. | |
| 6,399,063 B1 | 6/2002 | Hudziak et al. | |
| 6,596,746 B1 | 7/2003 | Das et al. | |
| 6,767,541 B2 | 7/2004 | Slamon et al. | |
| 2003/0153013 A1 | 8/2003 | Huang | |
| 2004/0038428 A1 | 2/2004 | MacBeath et al. | |
| 2006/0019256 A1* | 1/2006 | Clarke et al. | ....................... 435/6 |

FOREIGN PATENT DOCUMENTS

| | | |
|---|---|---|
| WO | WO 98/24893 | 6/1998 |
| WO | WO 99/51773 | 10/1999 |
| WO | WO 00/56934 | 9/2000 |
| WO | WO 2004/020583 A2 * | 3/2004 |

OTHER PUBLICATIONS

Taber's Cyclopedic Medical Dictionary (1985, F.A. Davis Company, Philadelphia, p. 274).*
Busken, C et al. (Digestive Disease Week Abstracts and Itinerary Planner, 2003, abstract No. 850).*
Kaiser (Science, 2006, 313: 1370).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C.*
U.S. Appl. No. 10/395,503, filed Mar. 24, 2003.
U.S. Appl. No. 11/401,502, filed Apr. 11, 2006.
Aghmesheh et al., Gynecol Oncol. Apr. 2005; 97(1):16-25.
Altschul et al.; 1996, Methods in Enzymology 266:460-480.
Ausubul et al. eds., 1995, Current Protocols in Molecular Biology, Units 2 [Northern Blotting], 4 [Southern Blotting], 15 [Immunoblotting] and 18 [PCR Analysis].
Bao, J. Chromatogyr. B. Biomed. Sci. 699:463-80 (1997).
Bartek et al., Int J. Cancer (1985) 36:299-306.
Bradley, in Robertson, ed., 1987, Teratocarcinomas and Embryonic Stem Cells: A Practical Approach, (IRL, Oxford), pp. 113-152.
Bromann PA, et al., Oncogene. Oct. 18, 2004; 23(48):7957-68.
Brooks et al., Cancer Epidemiol. Biomarkers Prev., 1998, 7:531-536.
Carter et al., 1993, Proc. Natl. Acad. Sci. USA 89:4285.
Carter, et al., 1986, Nucl. Acids Res. 13:4331.
Chang et al., Breast Cancer Res Treat. Sep. 2001; 69(2):101-13.
Chothia, 1976, J. Mol. Biol., 150:1.
Clark E, et al., Proceedings of the Am Soc Clin Oncol Abstract 3010, 2005.
Clark, M., ed., 1993, Protein Engineering of Antibody Molecules for Prophylactic and Therapeutic Applications in Man, Nottingham Academic, pp. 45-64.
Cohen, Jack, 1988, Oligodeoxynucleotides, Antisense Inhibitors of Gene Expression, CRC Press.
Couture, L.A. and Stinchcomb, D.T.; 1996, Tends Genet. 12:510-515.
Creighton, The Proteins, (W.H. Freeman & Co., N.Y.), 1996 p. v-x.

(Continued)

Primary Examiner — Peter J Reddig
(74) Attorney, Agent, or Firm — Woodcock Washburn LLP

(57) ABSTRACT

The invention described herein relates to methods and compositions useful in the diagnosis, treatment and management of cancers that express particular genes, including the moesin, caveolin 1, and/or yes-associated protein 1 genes.

15 Claims, 2 Drawing Sheets

OTHER PUBLICATIONS

De Marzo et al., Am. J.Patol. 155(6):1985-1992 (1999).
Donnelly et al., 1997, Ann. Rev. Immunol. 15:617-648.
Fiucci et al, Oncogene, 2002, 4:21(15) 2365-2375.
Fossati R, et al., J. Clin. Oncol Oct. 1998; 16(10:3439-60.
Foulkes et al., Cancer Res. Feb. 1, 2004: 64(3):830-5.
Gamallo et al., Mod. Pathol. 2001, 14(7):650-4.
Gipponni et al., J. Surg. Oncol. Mar. 1, 2004; 85(3):102-111.
Hanahan D., et al., Cell. Jan. 7, 2000; 100(1):57-70.
Harlow and Lane, Antibodies A Laboratory Manual, Cold Spring Harbor Laboratory: New York, 1988).
Irby RB et al., Oncogene. Nov. 20, 2000; 19(49):5636-42.
Ishizawar R et al., Cancer Cell. Sep. 2004; 6(3):209-14.
Iyer, R.P., et al.; J. Am. Chem. Soc. 112:1253-1254.
Iyer, R.P., et al.; J. Org. Chem. 55:4693-4698.
Jakobovits, 1998, Exp. Opin. Invest. Drugs 7(4):607-614.
Jemal A. et al., 2002, CA Cancer J. Clin. Jan.-Feb. 2002, 52(1):23-47.
Jensen OM, et al, Eur. J. Cancer. 1990; 26(11-12):1167-256.
Johnson F.M., et al., Dasatinib Tyrosine Kinase Inhibitor Suppresses Invasion and Induces Cell Cycle Arest and Apoptosis of Head and Neck Squamous Cell Carcinoma and Non-Small Cell Lung Cancer Cells; Clinical Cancer Research, The American Association for Cancer Research, US, Oct. 1, 2005; vol. 11 No. 19 I, pp. 6924-6932.
Jones et al., 1986, Nature 321:522-525.
Joo, H.J. et al., Increases Expression of Caveolin-1 and Microvessel Density Correlates with Metastasis and Poor Prognosis in Clear Cell Renal Carcinoma; BJU international, vol. 93, 2004, pp. 291-296, XP002439942.
Kobayashi et al., Clinical Cancer Research, 10, 572-580, 2004.
Korsching et al., J. Pathol. Aug. 2005; 206(4):451-7.
Kovacs et al., J Clin Pathol Feb. 2003; 56(2):139-41.
Kozak, 1989, Mol. Cell Biol., 9:5073-5080.
Laakso M., et alk.; Clin Cancer Res. Jul. 15, 2006; 12(14 Pt 1):4185-91.
Leong et al., Appl. Immunohistochem. 4(3):201 (1996).
Lethe et al., Int. J. Cancer 76(6):903-908 (1998).
Li et al., 1992, Cell 69:915.
Lombardo L.J. et al., Discovery of N-(2-chloro-6-methyl-phenyl)-2-(6-(4-(2-hydroxyethyl-piperazin-1-yl-2-methylpyrimidin-4-ylamino)thiazole-5-carboxamide, a Dual Scr/Able kinase Inhibitor with Potent Antitumor Activity in Preclinical Assays; Journal of Medical Chemistry, American Chemical Society, Washington, DC, Dec. 7, 2004, vol. 47(27):6658-61.
Manual of Histological Staining Method of the Armed Forces Institute of Pathology, 3rd edition (196) Lee G. Luna, HT (ASCP) Editor, The Blakston Division McGraw-Hill Book Company, New York.
Marrogi et al., 1999, J. Cutan, Pathol. 26(8):369-378.
Muller et al., 1991, MCB 11:1785.
Nam, Sangkil et al., Action of the Src Family Kinase Inhibito, Dasatinib (BMS-354825), on Human Prostate Cancer Cells; Cancer Research, American Association for Cancer Research, Baltimore, Maryland US, vol. 65, No. 20, pp. 9185-9189, Oct. 15, 2005.
National Cancer Institute of Canada: Canadian Cancer Statistics 1996, Toronto, Canada 1996; 21-23.
Nishizuka, S. et al., Diagnostic Markers That Distinguish Colon and Ovarian Adenocarcinomas: Identification by Genomic, Proteomic, Tissue Array Profiling, Cancer Research, vol. 63, Sep. 1, 2003, pp. 5243-5250, XP002439941.
O'Sullivan et al., Methods for the Preparation of Enzyme-Antibody conjugates for use in Enzyme Immunoassay, in Methods in Enzym, (ed. J. Langone & H. Van Vunakis), Academic press, New York, 73:147-166 (1981).
Paredes et al., Pathol. Res. Pract. 2002; 198(12):795-801.
Parra et al., J. Vasc. Surg. 28:669-675 (1998).
Partridge et al., 1996, Antisense & Nucleic Acid Drug Development 6:169-175.
Peralta et al., Cancer Oct. 1, 1999; 86(7):12630-72.
Perou CM, et al.; Nature, Aug. 17, 2000; 406(6796):747-52.
Playford MP et al., Oncogen. Oct. 18, 2004; 23(48):7928-46.
Protein Microarrays (2004) Mark Schena (Ed) Jones & Bartlett Publishers, Inc.
Reis-Filbo JS, J. Pathol. Nov. 2005; 207(3):367-369.
Riechmann et al., 1988, Nature 332:323-327.
Rongen et al., J. Immunol. Methods 204:105-133 (1997).
Sambrook et al.; 1989, Molecular Cloning: A Laboratory Manual, 2nd ed., New York: Cold Spring Harbor Press.
Schmalzing and Mashabeh, Electrophoresis 18:2184-93 (1997).
Self and Cook, Curr. Opin. Biotechnol. 7:60-65 (1996).
Shupnik MA et al., Oncogene. Oct. 18, 2004; 23(48):7979-89.
Sims et al., 1993, J. Immunol. 151:2296.
Slamon DJ, et al., N Engl J. Med. Mar. 15, 2001; 344(11):783-92.
Song I, et al., Cancer Res 66(11):5542-8, 2006.
Sorlie T et al., Proc Natl Acad Sci USA, Sep. 11, 2001; 98:10869-74.
Sotiriou C., et al., Proc Natl Acad Sci USA—Sep. 2, 2003; 100(18):10393-8.
Srinivasan D, et al., Cancer Res Jun. 1, 2006; 66(11):5648-55.
Strizzi et al., J Cell Physiol. Nov. 2004; 201(2):266-76.
Sudol M., Oncogen. Aug. 1994; 9(8):2145-52.
Synthesis 1:1-5 (1988), Negishi, E. et al.
The Armed Forces Institute of Pathology Advanced Laboratory Methods in Histology and Pathology (1994) Ulreka V. Mikel, Editor, Armed Forces Institute of Pathology7, American Registry of Pathology, Washington, D.C.
Thomas and Capecchi, 1987, Cell 51:503.
Thomas PA, et alk.; Clin Cancer Res. Oct. 1999; 5(10):2698-703.
Trevino JG, et al., Am J Pathol. Mar. 2006; 168(3):962-72.
Tsuda et al., Cancer Sci. Jan. 2005; 96(1):48-53.
Vaughan et al., 1998, Nature Biotechnology 16:535-539.
Verhoeyen et al., 1988, Science 239:1534-1536.
Wagner et al., Int J Cancer, Jul. 29, 1998; 77(3):354-60.
Wary KK, et al., Cell. Sep. 4, 1998; 94(5):625-34.
Wells et al, 1986, Philos. Trans. R. Soc. London Ser. A, 317:415.
Wells et al., 1985, Gene 34:315.
Wetels et al., Am J Path, (1991) 138:p. 751-63.
Williams TM, et al., Am J Cell Physiol. Mar. 2005; 288(3):C494-C506.
Wilson C.A. et al., Recent Translation Resaerch: Microarray Expression Profiling of Breast Cancer-Beyond Classification and Prognostic Markers; Breast Cancer Research. Jul. 19, 2004; 6(5):192-200.
Wilson CA, et al., Breast Cancer Research 2005, 7 Suppl 2:S 4.25.
Wolff et al., 1993, Cancer Res. 53:2560-2565.
Xiao et al (2005) Mol Cell Endocrino; 230(1):95-10.
Zoller et al., 1987, Nucl. Acids Res. 10:6487.
Ulusoy et al., "Mesenchymal Tumor of the Breast: Images of Two Cases," The Breast Journal, Sep. 2005, vol. 11, No. 5, pp. 358-359.
Coligan et al., "Current Protocols in Immunology," Jun. 1999, vol. 1, Supplement 31, 11 pages, pp. 1-9.

* cited by examiner

SEQUENCE LISTING

<160> NUMBER OF SEQ ID NOS: 16

<210> SEQ ID NO 1
<211> LENGTH: 3981
<212> TYPE: DNA
<213> ORGANISM: Homo sapiens

<400> SEQUENCE: 1

```
cgacaggggc ggctctttcc tgggtgsggt tgtgaagtc gtggcccgtt agcaggaagc        60
ctaacagtcg ccccgacgct agtgagggac ccaatctgag tccccggcca gccgaatcca       120
agccgtgtgt actgcgtgct cagcactgcc cgacagtcct agctaaactt cgccaactcc       180
gctgcctttg ccgccaccat gcccaaaacg atcagtgtgc gtgtgaccac catggatgca       240
gagctggagt ttgccatcca gcccaacacc accgggaagc agctatttga ccaggtggtg       300
aaaactattg gcttgaggga gtttggttc tttggtctgc agtaccagga cactaaaggt        360
ttctccacct ggctgaaact caataagaag gtgactgccc aggatgtgcg gaaggaaagc       420
cccctgctct ttaagttccg tgccaagttc taccctgagg atgtgtccga ggaattgatt       480
caggacatca ctcagcgcct gttctttctg caagtgaaag agggcattct caatgatgat       540
atttactgcc cgcctgagac cgctgtgctg ctggcctcgt atgctgtcca gtctaagtat       600
ggcgacttca ataaggaagt gcataagtct ggctacctgg ccggagacaa gttgctcccg       660
cagagagtcc tggaacagca caaactcaac aaggaccagt gggaggagcg gatccaggtg       720
tggcatgagg aacaccgtgg catgctcagg gaggatgctg tcctggaata tctgaagatt       780
gctcaagatc tggagatgta tggtgtgaac tacttcagca tcaagaacaa gaaaggctca       840
gagctgtggc tggggtgga tgccctgggt ctcaacatct atgagcagaa tgacagacta       900
actcccaaga taggcttccc ctggagtgaa atcaggaaca tctctttcaa tgataagaaa       960
tttgtcatca gcccattga caaaaaagcc ccggacttcg tcttctatgc tccccggctg      1020
cggattaaca agcggatctt ggccttgtgc atggggaacc atgaactata catgcgccgt      1080
cgcaagcctg ataccattga ggtgcagcag atgaaggcac aggcccggga ggagaagcac      1140
cagaagcaga tggagcgtgc tatgctgaa aatgagaaga gaagcgtga atggcagag         1200 aaggagaaag agaagattga acgggagaag gaggagctga tgagaggct gaagcagatc      1260 gaggaacaga ctaagaaggc tcagcaagaa ctggaagaac agaccgtag gctctggaa       1320 cttgagcagg aacggaagcg tgcccagagc gaggctgaaa agctggccaa ggagcgtcaa      1380
gaagctgaag aggccaagga ggccttgctg caggcctccc gggaccagaa aaagactcag      1440
gaacagctgg ccttggaaat ggcagagctg acagctcgaa tctcccagct ggagatggcc      1500
cgacagaaga aggagagtga ggctgtggag tggcagcaga aggcccagat ggtacaggaa      1560
gacttggaga agaccgtgc tgagctgaag actgccatga gtacacctca tggcagag        1620
```

```
cctgctgaga atgagcagga tgagcaggat gagaatgggg cagaggctag tgctgaccta      1680
cgggctgatg ctatggccaa ggaccgcagt gaggaggaac gtaccactga ggcagagaag      1740
aatgagcgtg tgcagaagca cctgaaggcc ctcacttcgg agctggccaa tgccagagat      1800
gagtccaaga agactgccaa tgacatgatc catgctgaga acatgcgact gggccgagac      1860
aaatacaaga ccctgcgcca gatccggcag ggcaacacca agcagcgcat tgacgaattt      1920
gagtctatgt aatgggcacc cagcctctag ggacccctcc tccctttttc cttgtcccca      1980
cactcctaca cctaactcac ctaactcata ctgtgctgga gccactaact agagcagccc      2040
tggagtcatg ccaagcattt aatgtagcca tgggaccaaa cctagcccct tagccccac       2100 ccacttccct gggcaaatga atggctcact atggtgccaa tggaacctcc tttctcttct      2160
ctgttccatt gaatctgtat ggctagaata cctacttct ccagcctaga ggtactttcc       2220
acttgatttt gcaaatgccc ttacacttac tgttgtccta tgggagtcaa gtgtggagta      2280
ggttggaagc tagctcccct cctctcccct accactgtct tcttcagggt cctgagattt      2340
acacggttgg agtgttatgc ggtctaggga atgagacagg acctaggata tcttctccag      2400
gatgtcaact gacctaaaat ttgccctccc atcccgttta gagttattta ggctttgtaa      2460
cgattggggg ataaaaagat gttcagtcat ttttgtttct acctcccaga tcggatctgt      2520
tgcaaactca gcctcaataa gccttgtcgt tgactttagg gactcaattt ctccccaggg      2580
tggatggggg aaatggtgcc ttcaagacct tcaccaaaca tactagaagg gcattggcca      2640
ttctattgtg gcaaggctga gtagaagatc ctaccccaat tccttgtagg agtataggcc      2700
ggtctaaagt gagctctatg ggcagatcta ccccttactt attattccag atctgcagtc      2760
acttcgtggg atctgcccct ccctgcttca atacccaaat cctctccagc tataacagta      2820
gggatgagta cccaaaagct cagccagccc catcaggact cttgtgaaaa gagaggatat      2880
gttcacacct agcgtcagta ttttccctgc taggggtttt aggtctcttc ccctctcaga      2940
gctacttggg ccatagctcc tgctccacag ccatcccagc cttggcatct agagcttgat      3000
gccagtaggc tcaactaggg agtgagtgca aaaagctgag tatggtgaga gaagcctgtg      3060
ccctgatcca agtttactca accctctcag gtgaccaaaa tccccttctc atcactcccc      3120
tccaaagagg tgactgggcc ctgcctctgt ttgacaaacc tctaacccag gtcttgacac      3180
cagctgttct gtcccttgga gctgtaaacc agagagctgc tggggattct ggcctagtcc      3240
cttccacacc cccaccccctt gctctcaacc caggagcatc cacctccttc tctgtctcat      3300
gtgtgctctt cttctttcta cagtattatg tactctactg atatctaaat attgatttct      3360
gccttccttg ctaatgcacc attagaagat attagtcttg gggcaggatg attttggcct      3420
cattacttta ccaccccac acctggaaag catatactat attacaaaat gacattttgc       3480
caaaattatt aatataagaa gctttcagta ttagtgatgt catctgtcac tataggtcat      3540
acaatccatt cttaaagtac ttgttatttg tttttattat tactgtttgt cttctcccca      3600
gggttcagtc ctcaaggggc catcctgtcc caccatgcag tgcccctagc ttagagcctc      3660
cctcaattcc ccctggccac cacccccac tctgtgcctg accttgagga gtcttgtgtg       3720
cattgctgtg aattagctca cttggtgata tgtcctatat tggctaaatt gaaacctgga      3780 attgtgggc aatctattaa tagctgcctt aaagtcagta acttacccctt agggaggctg      3840 ggggaaaagg ttagattttg tattcagggg ttttttgtgt acttttttggg ttttttaaaa      3900 attgttttg gagggttta tgctcaatcc atgttctatt tcagtgccaa taaaatttag        3960
gaagacttca aaaaaaaaaa a                                                3981
```

<210> SEQ ID NO 2
<211> LENGTH: 2704
<212> TYPE: DNA
<213> ORGANISM: Homo sapiens

<400> SEQUENCE: 2

```
gggagaaacg ttctcactcg ctctctgctc gctgcgggcg ctccccgccc tctgctgcca      60
gaaccttggg gatgtgccta gacccggcgc agcacacgtc cgggccaacc gcgagcagaa     120
caaacctttg gcgggcggcc aggaggctcc ctcccagcca ccgcccccct ccagcgcctt     180 ttttccccc catacaatac aagatcttcc ttcctcagtt cccttaaagc acagcccagg     240
gaaacctcct cacagttttc atccagccac gggccagcat gtctgggggc aaatacgtag     300
actcggaggg acatctctac accgttccca tccgggaaca gggcaacatc tacaagccca     360
acaacaaggc catggcagac gagctgagcg agaagcaagt gtacgacgcg cacaccaagg     420
agatcgacct ggtcaaccgc gaccctaaac acctcaacga tgacgtggtc aagattgact     480
ttgaagatgt gattgcagaa ccagaaggga cacacagttt tgacggcatt tggaaggcca     540
gcttcaccac cttcactgtg acgaaatact ggttttaccg cttgctgtct gccctctttg     600
gcatcccgat ggcactcatc tggggcattt acttcgccat tctctctttc ctgcacatct     660
gggcagttgt accatgcatt aagagcttcc tgattgagat tcagtgcatc agccgtgtct     720
attccatcta cgtccacacc gtctgtgacc cactctttga agctgttggg aaaatattca     780
gcaatgtccg catcaacttg cagaaagaaa tataaatgac atttcaagga tagaagtata     840
cctgattttt tttccttta attttcctgg tgccaatttc aagttccaag ttgctaatac     900
agcaacaatt tatgaattga attatcttgg ttgaaaataa aaagatcact ttctcagttt     960
tcataagtat tatgtctctt ctgagctatt tcatctattt ttggcagtct gaatttttaa    1020
aacccattta aatttttttc cttacctttt tatttgcatg tggatcaacc atcgctttat    1080
tggctgagat atgaacatat tgttgaaagg taatttgaga gaaatatgaa gaactgagga    1140
ggaaaaaaaa aaaaaagaaa agaaccaaca acctcaactg cctactccaa aatgttggtc    1200
attttatgtt aagggaagaa ttccagggta tggccatgga gtgtacaagt atgtgggcag    1260
attttcagca aactcttttc ccactgttta aggagttagt ggattactgc cattcacttc    1320
ataatccagt aggatccagt gatccttaca agttagaaaa cataatcttc tgccttctca    1380
tgatccaact aatgccttac tcttcttgaa atttttaacct atgatatttt ctgtgcctga    1440
atatttgtta tgtagataac aagacctcag tgccttcctg ttttttcacat tttccttttc    1500 aaatagggtc taactcagca actcgcttta ggtcagcagc ctccctgaag accaaaatta    1560
gaatatccat gacctagttt tccatgcgtg tttctgactc tgagctacag agtctggtga    1620
agctcacttc tgggcttcat ctggcaacat ctttatccgt agtgggtatg gttgacacta    1680
gcccaatgaa atgaattaaa gtggaccaat agggctgagc tctctgtggg ctggcagtcc    1740
tggaagccag cttttccctgc ctctcatcaa ctgaatgagg tcagcatgtc tattcagctt    1800
cgtttatttt caagaataat cacgctttcc tgaatccaaa ctaatccatc accgggtgg    1860 tttagtggct caacattgtg ttcccatttc agctgatcag tgggcctcca aggaggggct    1920
gtaaaatgga ggccattgtg tgagcctatc agagttgctg caaacctgac ccctgctcag    1980
taaagcactt gcaaccgtct gttatgctgt gacacatggc cctcccccct gccaggagct    2040
ttggacctaa tccaagcatc cctttgccca gaaagaagat gggggaggag gcagtaataa    2100
aaagattgaa gtattttgct ggaataagtt caaattcttc tgaactcaaa ctgaggaatt    2160
tcacctgtaa acctgagtcg tacagaaagc tgcctggtat atccaaaagc ttttattcc    2220
```

```
tcctgctcat attgtgattc tgcctttggg gacttttctt aaaccttcag ttatgatttt    2280
tttttcatac acttattgga actctgcttg atttttgcct cttccagtct tcctgacact    2340
ttaattacca acctgttacc tactttgact ttttgcattt aaaacagaca ctggcatgga    2400
tatagtttta cttttaaact gtgtacataa ctgaaaatgt gctatactgc atactttta    2460 aatgtaaaga tattttatc tttatatgaa gaaaatcact taggaaatgg ctttgtgatt    2520
caatctgtaa actgtgtatt ccaagacatg tctgttctac atagatgctt agtccctcat    2580
gcaaatcaat tactggtcca aaagattgct gaaattttat atgcttactg atatatttta    2640
caatttttta tcatgcatgt cctgtaaagg ttacaagcct gcacaataaa aatgtttaac    2700
ggtt                                                                 2704

<210> SEQ ID NO 3
<211> LENGTH: 5128
<212> TYPE: DNA
<213> ORGANISM: Homo sapiens

<400> SEQUENCE: 3
ccgagtgcct cgcagcccct cccgaggcgc agccgccaga ccagtggagc cggggcgcag      60
ggcgggggcg gaggcgccgg ggcggggat gcggggccgc ggcgcagccc ccggccctg      120 agagcgagga cagcgccgcc cggcccgcag ccgtcgccgc ttctccacct cggcccgtgg    180
agccggggcg tccgggcgta gccctcgctc gcctgggtca ggggtgcgc gtcggggggag    240 gcagaagcca tggatcccgg gcagcagccg ccgcctcaac cggcccccca gggccaaggg    300
cagccgcctt cgcagccccc gcaggggcag ggcccgccgt ccggaccccgg gcaaccggca    360 cccgcggcga cccaggcggc gccgcaggca ccccccgccg ggcatcagat cgtgcacgtc    420 cgcgggggact cggagaccga cctggaggcg ctcttcaacg ccgtcatgaa ccccaagacg    480
gccaacgtgc cccagaccgt gcccatgagg ctccggaagc tgcccgactc cttcttcaag    540
ccgccggagc ccaaatccca ctcccgacag gccagtactg atgcaggcac tgcaggagcc    600
ctgactccac agcatgttcg agctcattcc tctccagctt ctctgcagtt gggagctgtt    660
tctcctggga cactgacccc cactggagta gtctctggcc cagcagctac acccacagct    720
cagcatcttc gacagtcttc ttttgagata cctgatgatg tacctctgcc agcaggttgg    780
gagatggcaa agacatcttc tggtcagaga tacttcttaa atcacatcga tcagacaaca    840
acatggcagg accccaggaa ggccatgctg tcccagatga acgtcacagc ccccaccagt    900
ccaccagtgc agcagaatat gatgaactcg gcttcagcca tgaaccagag aatcagtcag    960
agtgctccag tgaaacagcc accacccctg gctccccaga gcccacaggg aggcgtcatg    1020
ggtggcagca actccaacca gcagcaacag atgcgactgc agcaactgca gatggagaag    1080
gagaggctgc ggctgaaaca gcaagaactg cttcggcagg tgaggccaca ggagttagcc    1140
ctgcgtagcc agttaccaac actggagcag gatggtggga ctcaaaatcc agtgtcttct    1200
cccgggatgt ctcaggaatt gagaacaatg acgaccaata gctcagatcc tttccttaac    1260
agtggcacct atcactctcg agatgagagt acagacagtg gactaagcat gagcagctac    1320
agtgtccctc gaaccccaga tgacttcctg aacagtgtgg atgagatgga tacaggtgat    1380
actatcaacc aaagcaccct gcctcacag cagaaccgtt tcccagacta ccttgaagcc    1440
attcctggga caaatgtgga ccttggaaca ctgaaggag atggaatgaa catagaagga    1500
gaggagctga tgccaagtct gcaggaagct ttgagtctg acatccttaa tgacatggag    1560 tctgtttgg ctgccaccaa gctagataaa gaaagctttc ttacatggtt atagagccct    1620
```

```
caggcagact gaattctaaa tctgtgaagg atctaaggag acacatgcac cggaaatttc   1680
cataagccag ttgcagtttt caggctaata cagaaaaaga tgaacaaacg tccagcaaga   1740
tactttaatc ctctattttg ctcttccttg tccattgctg ctgttaatgt attgctgacc   1800
tctttcacag ttggctctaa agaatcaaaa gaaaaaaact ttttatttct tttgctatta   1860
aaactactgt tcattttggg ggctggggga agtgagcctg tttggatgat ggatgccatt   1920
ccttttgccc agttaaatgt tcaccaatca ttttaactaa atactcagac ttagaagtca   1980
gatgcttcat gtcacagcat ttagtttgtt caacagttgt ttcttcagct tcctttgtcc   2040
agtggaaaaa catgatttac tggtctgaca agccaaaaat gttatatctg atattaaata   2100
cttaatgctg atttgaagag atagctgaaa ccaaggctga agactgtttt actttcagta   2160
ttttcttttc ctcctagtgc tatcattagt cacataatga ccttgatttt attttaggag   2220
cttataaggc atgagacaat ttccatataa atatattaat tattgccaca tactctaata   2280
tagattttgg tggataattt tgtgggtgtg catttttgttc tgttttgttg ggttttttgt   2340 ttttttttgtt tttggcaggg tcggtggggg ggttggttgg ttggttggtt ttgtcggaac   2400
ctaggcaaat gaccatatta gtgaatctgt taatagttgt agcttgggat ggttattgta   2460
gttgttttgg taaaatcttc atttcctggt ttttttttacc accttattta aatctcgatt   2520
atctgctctc tcttttatat acatacacac acccaaacat aacatttata atagtgtggt   2580
agtggaatgt atccttttt aggtttccct gctttccagt taattttttaa aatggtagcg   2640 ctttgtatgc atttagaata catgactagt agtttatatt tcactggtag tttaaatctg   2700
gttggggcag tctgcagatg tttgaagtag tttagtgttc tagaaagagc tattactgtg   2760
gatagtgcct agggagtgc tccacgccct ctgggcatac ggtagatatt atctgatgaa   2820
ttggaaagga gcaaaccaga aatggcttta ttttctccct tggactaatt tttaagtctc   2880
gattggaatt cagtgagtag gttcataatg tgcatgacag aaataagctt tatagtggtt   2940
taccttcatt tagctttgga agttttcttt gccttagttt tggaagtaaa ttctagtttg   3000
tagttctcat ttgtaatgaa cacattaacg actagattaa aatattgcct tcaagattgt   3060
tcttacttac aagacttgct cctacttcta tgctgaaaat tgaccctgga tagaatacta   3120
taaggttttg agttagctgg aaaagtgatc agattaataa atgtatattg gtagttgaat   3180
ttagcaaaga aatagagata atcatgatta tacctttatt tttacaggaa gagatgatgt   3240
aactagagta tgtgtctaca ggagtaataa tggtttccaa agagtatttt ttaaaggaac   3300
aaaacgagca tgaattaact cttcaatata agctatgaag taatagttgg ttgtgaatta   3360
aagtggcacc agctagcacc tctgtgtttt aagggtcttt caatgttttct agaataagcc   3420 cttattttca agggttcata acaggcataa aatctcttct cctggcaaaa gctgctatga   3480
aaagcctcag cttgggaaga tagatttttt tccccccaat tacaaaatct aagtattttg   3540
gcccttcaat ttggaggagg gcaaaagttg gaagtaagaa gttttatttt aagtactttc   3600
agtgctcaaa aaaatgcaat cactgtgttg tatataatag ttcataggtt gatcactcat   3660
aataattgac tctaaggctt ttattaagaa aacagcagaa agattaaatc ttgaattaag   3720
tctgggggga aatggccact gcagatggag ttttagagta gtaatgaaat tctacctaga   3780
atgcaaaatt gggtatatga attacatagc atgttgttgg gatttttttt aatgtgcaga   3840
agatcaaagc tacttggaag gagtgcctat aatttgccag tagccacaga ttaagattat   3900
atcttatata tcagcagatt agctttagct taggggagg gtgggaaagt ttgggggggg   3960
ggttgtgaag atttaggggg accttgatag agaactttat aaacttcttt ctctttaata   4020
```

```
aagacttgtc ttacaccgtg ctgccattaa aggcagctgt tctagagttt cagtcaccta    4080
agtacaccca caaacaata tgaatatgga gatcttcctt tacccctcaa ctttaatttg    4140
cccagttata cctcagtgtt gtagcagtac tgtgatacct ggcacagtgc tttgatctta    4200
cgatgccctc tgtactgacc tgaaggagac ctaagagtcc tttcccttt tgagtttgaa    4260 tcatagcctt gatgtggtct cttgttttat gtccttgttc ctaatgtaaa agtgcttaac    4320
tgcttcttgg ttgtattggg tagcattggg ataagatttt aactgggtat tcttgaattg    4380
cttttacaat aaaccaattt tataatcttt aaatttatca acttttaca tttgtgttat    4440 tttcagtcag ggcttcttag atctactat ggttgatgga gcacattgat ttggagtttc    4500
agatcttcca aagcactatt tgttgtaata acttttctaa atgtagtgcc tttaaaggaa    4560
aaatgaacac agggaagtga ctttgctaca aataatgttg ctgtgttaag tattcatatt    4620
aaatacatgc cttctatatg gaacatggca gaaagactga aaaataacag taattaattg    4680
tgtaattcag aattcatacc aatcagtgtt gaaactcaaa cattgcaaaa gtgggtggca    4740
atattcagtg cttaacactt ttctagcgtt ggtacatctg agaaatgagt gctcaggtgg    4800
attttatcct cgcaagcatg ttgttataag aattgtgggt gtgcctatca taacaattgt    4860
tttctgtatc ttgaaaaagt attctccaca ttttaaatgt tttatattag agaattcttt    4920
aatgcacact tgtcaaatat atatatatag taccaatgtt acctttttat tttttgtttt    4980
agatgtaaga gcatgctcat atgttaggta cttacataaa ttgttacatt attttttctt    5040
atgtaatacc ttttgtttg tttatgtggt tcaaatatat tctttcctta aaaaaaaaa    5100 aaaaaaaaaa aaaaaaaaa aaaaaaaa                                        5128
```

<210> SEQ ID NO 4
<211> LENGTH: 577
<212> TYPE: PRT
<213> ORGANISM: Homo sapiens

<400> SEQUENCE: 4

```
Met Pro Lys Thr Ile Ser Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Phe Phe Gly Leu Gln
        35                  40                  45

Tyr Gln Asp Thr Lys Gly Phe Ser Thr Trp Leu Lys Leu Asn Lys Lys
    50                  55                  60

Val Thr Ala Gln Asp Val Arg Lys Glu Ser Pro Leu Leu Phe Lys Phe
65                  70                  75                  80

Arg Ala Lys Phe Tyr Pro Glu Asp Val Ser Glu Glu Leu Ile Gln Asp
                85                  90                  95

Ile Thr Gln Arg Leu Phe Phe Leu Gln Val Lys Glu Gly Ile Leu Asn
            100                 105                 110

Asp Asp Ile Tyr Cys Pro Pro Glu Thr Ala Val Leu Leu Ala Ser Tyr
        115                 120                 125

Ala Val Gln Ser Lys Tyr Gly Asp Phe Asn Lys Glu Val His Lys Ser
    130                 135                 140

Gly Tyr Leu Ala Gly Asp Lys Leu Leu Pro Gln Arg Val Leu Glu Gln
145                 150                 155                 160

His Lys Leu Asn Lys Asp Gln Trp Glu Glu Arg Ile Gln Val Trp His
                165                 170                 175
```

```
Glu Glu His Arg Gly Met Leu Arg Glu Asp Ala Val Leu Glu Tyr Leu
                180                 185                 190

Lys Ile Ala Gln Asp Leu Glu Met Tyr Gly Val Asn Tyr Phe Ser Ile
                195                 200                 205

Lys Asn Lys Lys Gly Ser Glu Leu Trp Leu Gly Val Asp Ala Leu Gly
            210                 215                 220

Leu Asn Ile Tyr Glu Gln Asn Asp Arg Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
                260                 265                 270

Arg Leu Arg Ile Asn Lys Arg Ile Leu Ala Leu Cys Met Gly Asn His
                275                 280                 285

Glu Leu Tyr Met Arg Arg Arg Lys Pro Asp Thr Ile Glu Val Gln Gln
                290                 295                 300

Met Lys Ala Gln Ala Arg Glu Glu Lys His Gln Lys Gln Met Glu Arg
305                 310                 315                 320

Ala Met Leu Glu Asn Glu Lys Lys Lys Arg Glu Met Ala Glu Lys Glu
                325                 330                 335

Lys Glu Lys Ile Glu Arg Glu Lys Glu Glu Leu Met Glu Arg Leu Lys
                340                 345                 350

Gln Ile Glu Glu Gln Thr Lys Lys Ala Gln Gln Glu Leu Glu Glu Gln
                355                 360                 365

Thr Arg Arg Ala Leu Glu Leu Glu Gln Glu Arg Lys Arg Ala Gln Ser
370                 375                 380

Glu Ala Glu Lys Leu Ala Lys Glu Arg Gln Glu Ala Glu Glu Ala Lys
385                 390                 395                 400

Glu Ala Leu Leu Gln Ala Ser Arg Asp Gln Lys Lys Thr Gln Glu Gln
                405                 410                 415

Leu Ala Leu Glu Met Ala Glu Leu Thr Ala Arg Ile Ser Gln Leu Glu
                420                 425                 430

Met Ala Arg Gln Lys Lys Glu Ser Glu Ala Val Glu Trp Gln Gln Lys
                435                 440                 445

Ala Gln Met Val Gln Glu Asp Leu Glu Lys Thr Arg Ala Glu Leu Lys
450                 455                 460

Thr Ala Met Ser Thr Pro His Val Ala Glu Pro Ala Glu Asn Glu Gln
465                 470                 475                 480

Asp Glu Gln Asp Glu Asn Gly Ala Glu Ala Ser Ala Asp Leu Arg Ala
                485                 490                 495

Asp Ala Met Ala Lys Asp Arg Ser Glu Glu Glu Arg Thr Thr Glu Ala
                500                 505                 510

Glu Lys Asn Glu Arg Val Gln Lys His Leu Lys Ala Leu Thr Ser Glu
                515                 520                 525

Leu Ala Asn Ala Arg Asp Glu Ser Lys Lys Thr Ala Asn Asp Met Ile
530                 535                 540

His Ala Glu Asn Met Arg Leu Gly Arg Asp Lys Tyr Lys Thr Leu Arg
545                 550                 555                 560

Gln Ile Arg Gln Gly Asn Thr Lys Gln Arg Ile Asp Glu Phe Glu Ser
                565                 570                 575

Met
```

-continued

```
<210> SEQ ID NO 5
<211> LENGTH: 178
<212> TYPE: PRT
<213> ORGANISM: Homo sapiens

<400> SEQUENCE: 5

Met Ser Gly Gly Lys Tyr Val Asp Ser Glu Gly His Leu Tyr Thr Val
1               5                   10                  15

Pro Ile Arg Glu Gln Gly Asn Ile Tyr Lys Pro Asn Asn Lys Ala Met
            20                  25                  30

Ala Asp Glu Leu Ser Glu Lys Gln Val Tyr Asp Ala His Thr Lys Glu
        35                  40                  45

Ile Asp Leu Val Asn Arg Asp Pro Lys His Leu Asn Asp Val Val
    50                  55                  60

Lys Ile Asp Phe Glu Asp Val Ile Ala Glu Pro Glu Gly Thr His Ser
65                  70                  75                  80

Phe Asp Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
            100                 105                 110

Leu Ile Trp Gly Ile Tyr Phe Ala Ile Leu Ser Phe Leu His Ile Trp
        115                 120                 125

Ala Val Val Pro Cys Ile Lys Ser Phe Leu Ile Glu Ile Gln Cys Ile
    130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175

Glu Ile

<210> SEQ ID NO 6
<211> LENGTH: 454
<212> TYPE: PRT
<213> ORGANISM: Homo sapiens

<400> SEQUENCE: 6

Met Asp Pro Gly Gln Gln Pro Pro Gln Pro Ala Pro Gln Gly Gln
1               5                   10                  15

Gly Gln Pro Pro Ser Gln Pro Pro Gln Gly Gln Gly Pro Ser Gly
            20                  25                  30

Pro Gly Gln Pro Ala Pro Ala Ala Thr Gln Ala Ala Pro Gln Ala Pro
        35                  40                  45

Pro Ala Gly His Gln Ile Val His Val Arg Gly Asp Ser Glu Thr Asp
    50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
            100                 105                 110

Gly Thr Ala Gly Ala Leu Thr Pro Gln His Val Arg Ala His Ser Ser
        115                 120                 125

Pro Ala Ser Leu Gln Leu Gly Ala Val Ser Pro Gly Thr Leu Thr Pro
    130                 135                 140

Thr Gly Val Val Ser Gly Pro Ala Ala Thr Pro Thr Ala Gln His Leu
145                 150                 155                 160
```

```
Arg Gln Ser Ser Phe Glu Ile Pro Asp Asp Val Pro Leu Pro Ala Gly
            165                 170                 175
Trp Glu Met Ala Lys Thr Ser Ser Gly Gln Arg Tyr Phe Leu Asn His
        180                 185                 190
Ile Asp Gln Thr Thr Thr Trp Gln Asp Pro Arg Lys Ala Met Leu Ser
    195                 200                 205
Gln Met Asn Val Thr Ala Pro Thr Ser Pro Pro Val Gln Gln Asn Met
210                 215                 220
Met Asn Ser Ala Ser Ala Met Asn Gln Arg Ile Ser Gln Ser Ala Pro
225                 230                 235                 240
Val Lys Gln Pro Pro Leu Ala Pro Gln Ser Pro Gln Gly Gly Val
                245                 250                 255
Met Gly Gly Ser Asn Ser Asn Gln Gln Gln Met Arg Leu Gln Gln
            260                 265                 270
Leu Gln Met Glu Lys Glu Arg Leu Arg Leu Lys Gln Gln Glu Leu Leu
        275                 280                 285
Arg Gln Val Arg Pro Gln Glu Leu Ala Leu Arg Ser Gln Leu Pro Thr
    290                 295                 300
Leu Glu Gln Asp Gly Gly Thr Gln Asn Pro Val Ser Ser Pro Gly Met
305                 310                 315                 320
Ser Gln Glu Leu Arg Thr Met Thr Thr Asn Ser Ser Asp Pro Phe Leu
                325                 330                 335
Asn Ser Gly Thr Tyr His Ser Arg Asp Glu Ser Thr Asp Ser Gly Leu
            340                 345                 350
Ser Met Ser Ser Tyr Ser Val Pro Arg Thr Pro Asp Asp Phe Leu Asn
        355                 360                 365
Ser Val Asp Glu Met Asp Thr Gly Asp Thr Ile Asn Gln Ser Thr Leu
    370                 375                 380
Pro Ser Gln Gln Asn Arg Phe Pro Asp Tyr Leu Glu Ala Ile Pro Gly
385                 390                 395                 400
Thr Asn Val Asp Leu Gly Thr Leu Glu Gly Asp Gly Met Asn Ile Glu
                405                 410                 415
Gly Glu Glu Leu Met Pro Ser Leu Gln Glu Ala Leu Ser Ser Asp Ile
            420                 425                 430
Leu Asn Asp Met Glu Ser Val Leu Ala Ala Thr Lys Leu Asp Lys Glu
        435                 440                 445
Ser Phe Leu Thr Trp Leu
    450
```

<210> SEQ ID NO 7
<211> LENGTH: 6456
<212> TYPE: DNA
<213> ORGANISM: Homo sapiens

<400> SEQUENCE: 7

```
gagttgtgcc tggagtgatg tttaagccaa tgtcagggca aggcaacagt ccctggccgt      60
cctccagcac ctttgtaatg catatgagct cgggagacca gtacttaaag ttggaggccc     120
gggagcccag gagctggcgg agggcgttcg tcctgggact gcacttgctc ccgtcgggtc     180
gcccggcttc accggacccg caggctcccg ggcagggcc ggggccagag ctcgcgtgtc      240
ggcgggacat gcgctgcgtc gcctctaacc tcgggctgtg ctcttttcc aggtggcccg      300
ccggtttctg agccttctgc cctgcgggga cacggtctgc accctgcccg cggccacgga     360
ccatgaccat gaccctccac accaaagcat ccgggatggc cctactgcat cagatccaag     420
ggaacgagct ggagcccctg aaccgtccgc agctcaagat cccctggag cggccccctgg    480
```

```
gcgaggtgta cctggacagc agcaagcccg ccgtgtacaa ctaccccgag ggcgccgcct      540
acgagttcaa cgccgcggcc gccgccaacg cgcaggtcta cggtcagacc ggcctcccct      600
acggccccgg gtctgaggct gcggcgttcg gctccaacgg cctgggggt tcccccccac      660 tcaacagcgt gtctccgagc ccgctgatgc tactgcaccc gccgccgcag ctgtcgcctt      720
tcctgcagcc ccacggccag caggtgccct actacctgga gaacgagccc agcggctaca      780
cggtgcgcga ggccggcccg ccggcattct acaggccaaa ttcagataat cgacgccagg      840
gtggcagaga aagattggcc agtaccaatg acaagggaag tatggctatg aatctgcca       900 aggagactcg ctactgtgca gtgtgcaatg actatgcttc aggctaccat tatggagtct      960
ggtcctgtga gggctgcaag gccttcttca agagaagtat tcaaggacat aacgactata     1020
tgtgtccagc caccaaccag tgcaccattg ataaaaacag gaggaagagc tgccaggcct     1080
gccggctccg caaatgctac gaagtgggaa tgatgaaagg tgggatacga aagaccgaa      1140 gaggagggag aatgttgaaa cacaagcgcc agagagatga tggggagggc agggtgaag     1200 tggggtctgc tggagacatg agagctgcca acctttggcc aagcccgctc atgatcaaac     1260
gctctaagaa gaacagcctg ccttgtccc tgacggccga ccagatggtc agtgccttgt     1320
tggatgctga gccccccata ctctattccg agtatgatcc taccagaccc ttcagtgaag     1380
cttcgatgat gggcttactg accaacctgg cagacaggga gctggttcac atgatcaact     1440
gggcgaagag ggtgccaggc tttgtggatt tgaccctcca tgatcaggtc accttctag      1500 aatgtgcctg gctagagatc ctgatgattg gtctcgtctg cgcgctccatg agcacccag     1560 ggaagctact gtttgctcct aacttgctct tggacaggaa ccagggaaaa tgtgtagagg     1620
gcatggtgga gatcttcgac atgctgctgg ctacatcatc tcggttccgc atgatgaatc     1680
tgcagggaga ggagtttgtg tgcctcaaat ctattatttt gcttaattct ggagtgtaca     1740
catttctgtc cagcaccctg aagtctctgg aagagaagga ccatatccac cgagtcctgg     1800
acaagatcac agacactttg atccacctga tggccaaggc aggcctgacc ctgcagcagc     1860
agcaccagcg gctggcccag ctcctcctca tcctctccca catcaggcac atgagtaaca     1920
aaggcatgga gcatctgtac agcatgaagt gcaagaacgt ggtgcccctc tatgacctgc     1980
tgctggagat gctggacgcc caccgcctac atgcgcccac tagccgtgga ggggcatccg     2040
tggaggagac ggaccaaagc cacttggcca ctgcgggctc tacttcatcg cattccttgc     2100
aaaagtatta catcacgggg gaggcagagg gtttccctgc cacggtctga gagctccctg     2160
gctcccacac ggttcagata atccctgctg cattttaccc tcatcatgca ccactttagc     2220
caaattctgt ctcctgcata cactccggca tgcatccaac accaatggct ttctagatga     2280
gtggccattc atttgcttgc tcagttctta gtggcacatc ttctgtcttc tgttgggaac     2340
agccaaaggg attccaaggc taaatctttg taacagctct ctttccccct tgctatgtta     2400
ctaagcgtga ggattcccgt agctcttcac agctgaactc agtctatggg ttggggctca     2460
gataactctg tgcatttaag ctacttgtag agacccaggc ctggagagta gacatttgc      2520 ctctgataag cacttttaa atggctctaa gaataagcca cagcaaagaa tttaaagtgg      2580
ctcctttaat tggtgacttg gagaaagcta ggtcaagggt ttattatagc accctcttgt     2640
attcctatgg caatgcatcc ttttatgaaa gtggtacacc ttaaagcttt tatatgactg     2700
tagcagagta tctggtgatt gtcaattcat tcccctata ggaatacaag ggcacacag      2760 ggaaggcaga tccctagtt ggcaagacta ttttaacttg atacactgca gattcagatg      2820
tgctgaaagc tctgcctctg ctttccggt catgggttcc agttaattca tgcctcccat      2880
```

```
ggacctatgg agagcagcaa gttgatctta gttaagtctc cctatatgag ggataagttc    2940
ctgattttg  tttttatttt tgtgttacaa aagaaagccc tccctccctg aacttgcagt    3000
aaggtcagct tcaggacctg ttccagtggg cactgtactt ggatcttccc ggcgtgtgtg    3060
tgccttacac aggggtgaac tgttcactgt ggtgatgcat gatgagggta aatggtagtt    3120
gaaaggagca ggggccctgg tgttgcattt agccctgggg catggagctg aacagtactt    3180
gtgcaggatt gttgtggcta ctagagaaca agagggaaag tagggcagaa actggataca    3240
gttctgaggc acagccagac ttgctcaggg tggccctgcc acaggctgca gctacctagg    3300
aacattcctt gcagaccccg cattgccctt tgggggtgcc ctgggatccc tggggtagtc    3360
cagctcttct tcatttccca gcgtggccct ggttggaaga agcagctgtc acagctgctg    3420
tagacagctg tgttcctaca attggcccag caccctgggg cacggagaa gggtggggac     3480
cgttgctgtc actactcagg ctgactgggg cctggtcaga ttacgtatgc ccttggtggt    3540
ttagagataa tccaaaatca gggtttggtt tggggaagaa aatcctcccc cttcctcccc    3600
cgccccgttc cctaccgcct ccactcctgc cagctcattt ccttcaattt cctttgaacc    3660
tataggctaa aaaagaaagg ctcattccag ccacagggca gccttccctg gcctttgct     3720
tctctagcac aattatgggt tacttccttt ttcttaacaa aaaagaatgt ttgatttcct    3780
ctgggtgacc ttattgtctg taattgaaac cctattgaga ggtgatgtct gtgttagcca    3840
atgacccagg tgagctgctc gggcttctct tggtatgtct tgtttggaaa agtggatttc    3900
attcatttct gattgtccag ttaagtgatc accaaaggac tgagaatctg ggagggcaaa    3960
aaaaaaaaaa aagtttttat gtgcacttaa atttgggac  aattttatgt atctgtgtta    4020
aggatatgtt taagaacata attcttttgt tgctgtttgt ttaagaagca ccttagtttg    4080
tttaagaagc accttatata gtataatata tattttttg  aaattacatt gcttgtttat    4140
cagacaattg aatgtagtaa ttctgttctg gatttaattt gactgggtta acatgcaaaa    4200
accaaggaaa aatatttagt tttttttttt tttttgtat  acttttcaag ctaccttgtc    4260
atgtatacag tcatttatgc ctaaagcctg gtgattattc atttaaatga agatcacatt    4320
tcatatcaac ttttgtatcc acagtagaca aaatagcact aatccagatg cctattgttg    4380
gatattgaat gacagacaat cttatgtagc aaagattatg cctgaaaagg aaaattattc    4440
agggcagcta attttgcttt taccaaaata tcagtagtaa tatttttgga cagtagctaa    4500
tgggtcagtg ggttcttttt aatgtttata cttagatttt cttttaaaaa aattaaaata    4560
aaacaaaaaa aaatttctag gactagacga tgtaatacca gctaaagcca aacaattata    4620
cagtggaagg ttttacatta ttcatccaat gtgtttctat tcatgttaag atactactac    4680
atttgaagtg gcagagaac  atcagatgat tgaaatgttc gcccaggggt ctccagcaac    4740
tttggaaatc tctttgtatt tttacttgaa gtgccactaa tggacagcag atattttctg    4800
gctgatgttg gtattgggtg taggaacatg atttaaaaaa aaactcttgc ctctgctttc    4860
ccccactctg aggcaagtta aaatgtaaaa gatgtgattt atctgggggg ctcaggtatg    4920
gtgggaagt  ggattcagga atctggggaa tggcaaatat attaagaaga gtattgaaag    4980
tatttggagg aaaatggtta attctgggtg tgcaccaggg ttcagtagag tccacttctg    5040
ccctggagac cacaaatcaa ctagctccat ttacagccat ttctaaaatg gcagcttcag    5100
ttctagagaa gaaagaacaa catcagcagt aaagtccatg gaatagctag tggtctgtgt    5160
ttcttttcgc cattgcctag cttgccgtaa tgattcctata atgccatcat gcagcaatta   5220
tgagaggcta ggtcatccaa agagaagacc ctatcaatgt aggttgcaaa atctaacccc    5280
```

| | |
|---|---|
| taaggaagtg cagtctttga tttgatttcc ctagtaacct tgcagatatg tttaaccaag | 5340 |
| ccatagccca tgccttttga gggctgaaca aataagggac ttactgataa tttactttg | 5400 |
| atcacattaa ggtgttctca ccttgaaatc ttatacactg aaatggccat tgatttaggc | 5460 |
| cactggctta gagtactcct tcccctgcat gacactgatt acaaatactt tcctattcat | 5520 |
| actttccaat tatgagatgg actgtgggta ctgggagtga tcactaacac catagtaatg | 5580 |
| tctaatattc acaggcagat ctgcttgggg aagctagtta tgtgaaaggc aaatagagtc | 5640 |
| atacagtagc tcaaaaggca accataattc tctttggtgc aggtcttggg agcgtgatct | 5700 |
| agattacact gcaccattcc caagttaatc ccctgaaaac ttactctcaa ctggagcaaa | 5760 |
| tgaactttgg tcccaaatat ccatcttttc agtagcgtta attatgctct gtttccaact | 5820 |
| gcatttcctt tccaattgaa ttaaagtgtg gcctcgtttt tagtcattta aaattgtttt | 5880 |
| ctaagtaatt gctgcctcta ttatggcact tcaattttgc actgtctttt gagattcaag | 5940 |
| aaaaatttct attcttttt ttgcatccaa ttgtgcctga acttttaaaa tatgtaaatg | 6000 |
| ctgccatgtt ccaaacccat cgtcagtgtg tgtgtttaga gctgtgcacc ctagaaacaa | 6060 |
| catattgtcc catgagcagg tgcctgagac acagacccct ttgcattcac agagaggtca | 6120 |
| ttggttatag agacttgaat aataagtga cattatgcca gtttctgttc tctcacaggt | 6180 |
| gataaacaat gcttttgtg cactacatac tcttcagtgt agagctcttg ttttatggga | 6240 |
| aaaggctcaa atgccaaatt gtgtttgatg gattaatatg ccctttgcc gatgcatact | 6300 |
| attactgatg tgactcggtt ttgtcgcagc tttgctttgt ttaatgaaac acacttgtaa | 6360 |
| acctcttttg cactttgaaa aagaatccag cgggatgctc gagcacctgt aaacaatttt | 6420 |
| ctcaacctat ttgatgttca aataaagaat taaact | 6456 |

<210> SEQ ID NO 8
<211> LENGTH: 5000
<212> TYPE: DNA
<213> ORGANISM: Homo sapiens

<400> SEQUENCE: 8

| | |
|---|---|
| ggatccattt tataagctca aagataatta cttttcagac taagaatatt tagggtaaaa | 60 |
| agtactgttc aacatctcta ctgaggatgt tatgatgtag cacactgtat aagctggagc | 120 |
| taaaggaaac tttccttaaa gtgctatta ctaaaaattg aacacattc cttaagacaa | 180 |
| atcgaagtgt ggcacacaac atccaaactt ccatcataga tacagaggtg ttaccatctc | 240 |
| ccactcccaa atttctttgt cacgctgagg atactcaaga ggagcaggac atgttggtcg | 300 |
| cagcaggaga aacttgaaag cattcacttt tatggaactc ataagggaga gaatctctta | 360 |
| tttagtatcg tccttgatac atttattatt ttaaagata atgtagccaa atgtcttcct | 420 |
| ctgtgttaaa tctttacaaa actgaaatct taaaatggtg acaaaaattc tacttctgat | 480 |
| agaatctatt cattttcca attagatagg gcataattct taatttgcaa acaaaacgt | 540 |
| aatatgctta tgaggttcca tcccaaagaa cctgctattg agagtagcat tcagaataac | 600 |
| gggtggaaat gccaactcca gagtttcaga tcctaccggt aattggggta gggaggggct | 660 |
| ttgggcgggg cctccctaga ggaggaggcg ttgttagaaa gctgtctggc cagtccacag | 720 |
| ctgtcactaa tcggggtaag ccttgttgta tttgtgcgtg tgggtggcat tctcaatgag | 780 |
| aactagcttc acttgtcatt tgagtgaaat ctacaacccg aggcggctag tgctcccgca | 840 |
| ctactgggat ctgagatctt cggagatgac tgtcgcccgc agtacggagc cagcagaagt | 900 |
| ccgacccttc ctgggaatgg gctgtaccga gaggtccgac tagccccagg gtttagtga | 960 |

-continued

```
gggggcagtg gaactcagcg agggactgag agcttcacag catgcacgag tttgatgcca    1020
gagaaaaagt cgggagataa aggagccgcg tgtcactaaa ttgccgtcgc agccgcagcc    1080
actcaagtgc cggacttgtg agtactctgc gtctccagtc ctcggacaga agttggagaa    1140
ctctcttgga gaactccccg agttaggaga cgagatctcc taacaattac tactttttct    1200
tgcgctcccc acttgccgct cgctgggaca aacgacagcc acagttcccc tgacgacagg    1260
atggaggcca agggcaggag ctgaccagcg ccgccctccc ccgccccgga cccaggaggt    1320
ggagatccct ccggtccagc cacattcaac acccactttc tcctccctct gccctatat    1380 tcccgaaacc ccctcctcct tccctttccc ctcctcctgg agacggggga ggagaaaagg    1440
ggagtccagt cgtcatgact gagctgaagg caaagggtcc ccgggctccc cacgtggcgg    1500
gcggcccgcc ctcccccgag gtcggatccc cactgctgtg tcgcccagcc gcaggtccgt    1560
tcccggggag ccagacctcg gacaccttgc ctgaagtttc ggccatacct atctccctgg    1620
acgggctact cttccctcgg ccctgccagg acaggaccc ctccgacgaa aagacgcagg     1680
accagcagtc gctgtcggac gtggagggcg catattccag agctgaagct acaaggggtg    1740
ctggaggcag cagttctagt cccccagaaa aggacagcgg actgctggac agtgtcttgg    1800
acactctgtt ggcgccctca ggtcccgggc agagccaacc cagccctccc gcctgcgagg    1860
tcaccagctc ttggtgcctg tttggccccg aacttcccga agatccaccg gctgcccccg    1920
ccacccagcg ggtgttgtcc ccgctcatga gccggtccgg gtgcaaggtt ggagacagct    1980
ccgggacggc agctgcccat aaagtgctgc cccggggcct gtcaccagcc cggcagctgc    2040
tgctcccggc ctctgagagc cctcactggt ccggggcccc agtgaagccg tctccgcagg    2100 ccgctgcgt ggaggttgag gaggaggatg ctctgagtc cgaggagtct gcgggtccgc      2160
ttctgaaggg caaacctcgg gctctgggtg gcgcggcggc tggaggagga gccgcggctg    2220
tcccgccggg ggcggcagca ggaggcgtcg ccctggtccc caaggaagat tcccgcttct    2280
cagcgcccag ggtcgccctg gtggagcagg acgcgccgat ggcgcccggg cgctccccgc    2340
tggccaccac ggtgatggat ttcatccacg tgcctatcct gcctctcaat cacgccttat    2400
tggcagcccg cactcggcag ctgctggaag acgaaagtta cgacggcggg gccggggctg    2460
ccagcgcctt tgccccgccg cggagttcac cctgtgcctc gtccaccccg gtcgctgtag    2520
gcgacttccc cgactgcgcg tacccgcccg acgccgagcc caaggacgac gcgtaccctc    2580
tctatagcga cttccagccc cccgctctaa agataaagga ggaggaggaa ggcgcggagg    2640
cctccgcgcg ctccccgcgt tcctaccttg tggccggtgc caaccccgca gccttcccgg    2700
atttcccgtt ggggccaccg ccccgctgc cgccgcgagc gaccccatcc agacccgggg     2760
aagcggcggt gacggccgca cccgccagtg cctcagtctc gtctgcgtcc tcctcggggt    2820
cgaccctgga gtgcatcctg tacaaagcgg agggcgcgcc gccccagcag ggcccgttcg    2880
cgccgccgcc ctgcaaggcg ccgggcgcga cggctgcct gctcccgcgg gacggcctgc     2940
cctccacctc cgcctctgcc gccgccgccg gggcggcccc cgcgctctac cctgcactcg    3000
gcctcaacgg gctcccgcag ctcggctacc aggccgccgt gctcaaggag ggcctgccgc    3060
aggtctaccc gccctatctc aactacctga ggccggattc agaagccagc cagagcccac    3120
aatacagctt cgagtcatta cctcagaaga tttgtttaat ctgtggggat gaagcatcag    3180
gctgtcatta tggtgtcctt acctgtggga gctgtaaggt cttctttaag agggcaatgg    3240
aagggcagca caactactta tgtgctggaa gaaatgactg catcgttgat aaaatccgca    3300
gaaaaaactg cccagcatgt cgccttagaa agtgctgtca ggctggcatg gtccttggag    3360
```

-continued

| | |
|---|---|
| gtcgaaaatt taaaaagttc aataaagtca gagttgtgag agcactggat gctgttgctc | 3420 |
| tcccacagcc agtgggcgtt ccaaatgaaa gccaagccct aagccagaga ttcactttt | 3480 |
| caccaggtca agacatacag ttgattccac cactgatcaa cctgttaatg agcattgaac | 3540 |
| cagatgtgat ctatgcagga catgacaaca caaaacctga cacctccagt tctttgctga | 3600 |
| caagtcttaa tcaactaggc gagaggcaac ttctttcagt agtcaagtgg tctaaatcat | 3660 |
| tgccaggttt tcgaaactta catattgatg accagataac tctcattcag tattcttgga | 3720 |
| tgagcttaat ggtgtttggt ctaggatgga gatcctacaa acacgtcagt gggcagatgc | 3780 |
| tgtattttgc acctgatcta atactaaatg aacagcggat gaaagaatca tcattctatt | 3840 |
| cattatgcct taccatgtgg cagatcccac aggagtttgt caagcttcaa gttagccaag | 3900 |
| aagagttcct ctgtatgaaa gtattgttac ttcttaatac aattcctttg aagggctac | 3960 |
| gaagtcaaac ccagtttgag gagatgaggt caagctacat tagagagctc atcaaggcaa | 4020 |
| ttggtttgag gcaaaaagga gttgtgtcga gctcacagcg tttctatcaa cttacaaaac | 4080 |
| ttcttgataa cttgcatgat cttgtcaaac aacttcatct gtactgcttg aatacattta | 4140 |
| tccagtcccg ggcactgagt gttgaatttc cagaaatgat gtctgaagtt attgctgcac | 4200 |
| aattacccaa gatattggca gggatggtga aacccttct ctttcataaa aagtgaatgt | 4260 |
| catctttttc ttttaaagaa ttaaattttg tggtatgtct ttttgttttg gtcaggatta | 4320 |
| tgaggtcttg agttttata atgttcttct gaaagcctta catttataac atcatagtgt | 4380 |
| gtaaatttaa aagaaaaatt gtgaggttct aattattttc ttttataaag tataattaga | 4440 |
| atgtttaact gttttgttta cccatatttt cttgaagaat ttacaagatt gaaaaagtac | 4500 |
| taaaattgtt aaagtaaact atcttatcca tattatttca taccatgtag gtgaggattt | 4560 |
| ttaacttttg catctaacaa atcatcgact taagagaaaa aatcttacat gtaataacac | 4620 |
| aaagctatta tatgttattt ctaggtaact ccctttgtgt caattatatt tccaaaaatg | 4680 |
| aacctttaaa atggtatgca aaattttgtc tatatatatt tgtgtgagga ggaaattcat | 4740 |
| aactttcctc agattttcaa aagtattttt aatgcaaaaa atgtagaaag agtttaaaac | 4800 |
| cactaaaata gattgatgtt cttcaaacta ggcaaaacaa ctcatatgtt aagaccattt | 4860 |
| tccagattgg aaacacaaat ctcttaggaa gttaataagt agattcatat cattatgcaa | 4920 |
| atagtattgt gggttttgta ggttttaaa ataacctttt tggggagag aattgtcctc | 4980 |
| taatgaggta ttgcgagtgg | 5000 |

```
<210> SEQ ID NO 9
<211> LENGTH: 4624
<212> TYPE: DNA
<213> ORGANISM: Homo sapiens

<400> SEQUENCE: 9
```

| | |
|---|---|
| ggaggaggtg gaggaggagg gctgcttgag gaagtataag aatgaagttg tgaagctgag | 60 |
| attcccctcc attgggaccg gagaaaccag gggagccccc cgggcagccg cgcgcccctt | 120 |
| cccacggggc cctttactgc gccgcgcgcc cggcccccac ccctcgcagc accccgcgcc | 180 |
| ccgcgccctc ccagccgggt ccagccgag ccatggggcc ggagccgcag tgagcaccat | 240 |
| ggagctggcg gccttgtgcc gctgggggct cctcctcgcc ctcttgcccc cggagccgc | 300 |
| gagcacccaa gtgtgcaccg gcacagacat gaagctgcgg ctccctgcca gtcccgagac | 360 |
| ccacctggac atgctccgcc acctctacca gggctgccag gtggtgcagg gaaacctgga | 420 |
| actcacctac ctgcccacca atgccagcct gtccttcctg caggatatcc aggaggtgca | 480 |

```
gggctacgtg ctcatcgctc acaaccaagt gaggcaggtc ccactgcaga ggctgcggat    540
tgtgcgaggc acccagctct ttgaggacaa ctatgccctg gccgtgctag acaatggaga    600
cccgctgaac aataccaccc ctgtcacagg ggcctcccca ggaggcctgc gggagctgca    660
gcttcgaagc ctcacagaga tcttgaaagg aggggtcttg atccagcgga acccccagct    720
ctgctaccag gacacgattt tgtggaagga catcttccac aagaacaacc agctggctct    780
cacactgata gacaccaacc gctctcgggc ctgccacccc tgttctccga tgtgtaaggg    840
ctcccgctgc tggggagaga gttctgagga ttgtcagagc ctgacgcgca ctgtctgtgc    900
cggtggctgt gcccgctgca aggggccact gcccactgac tgctgccatg agcagtgtgc    960
tgccggctgc acgggcccca agcactctga ctgcctggcc tgcctccact caaccacag   1020 tggcatctgt gagctgcact gcccagccct ggtcacctac aacacagaca cgtttgagtc   1080
catgcccaat cccgagggcc ggtatacatt cggcgccagc tgtgtgactg cctgtcccta   1140
caactacctt tctacggacg tgggatcctg caccctcgtc tgcccctgc acaaccaaga    1200 ggtgacagca gaggatggaa cacagcggtg tgagaagtgc agcaagccct gtgcccgagt   1260
gtgctatggt ctgggcatgg agcacttgcg agaggtgagg gcagttacca gtgccaatat   1320
ccaggagttt gctggctgca agaagatctt tgggagcctg gcatttctgc cggagagctt   1380
tgatggggac ccagcctcca acactgcccc gctccagcca gagcagctcc aagtgtttga   1440
gactctggaa gagatcacag gttacctata catctcagca tggccggaca gcctgcctga   1500
cctcagcgtc ttccagaacc tgcaagtaat ccggggacga attctgcaca atggcgccta   1560
ctcgctgacc ctgcaagggc tgggcatcag ctggctgggg ctgcgctcac tgagggaact   1620
gggcagtgga ctggccctca tccaccataa cacccacctc tgcttcgtgc acacggtgcc   1680
ctgggaccag ctctttcgga acccgcacca agctctgctc cacactgcca accggccaga   1740
ggacgagtgt gtgggcgagg gcctggcctg ccaccagctg tgcgcccgag ggcactgctg   1800
gggtccaggg cccacccagt gtgtcaactg cagccagttc cttcggggcc aggagtgcgt   1860
ggaggaatgc cgagtactgc aggggctccc cagggagtat gtgaatgcca ggcactgttt   1920
gccgtgccac cctgagtgtc agccccagaa tggctcagtg acctgttttg gaccggaggc   1980
tgaccagtgt gtggcctgtg cccactataa ggaccctccc ttctgcgtgg cccgctgccc   2040
cagcggtgtg aaacctgacc tctcctacat gcccatctgg aagtttccag atgaggaggg   2100
cgcatgccag ccttgcccca tcaactgcac ccactcctgt gtggacctgg atgacaaggg   2160
ctgccccgcc gagcagagag ccagccctct gacgtccatc atctctgcgg tggttggcat   2220
tctgctggtc gtggtcttgg gggtggtctt tgggatcctc atcaagcgac ggcagcagaa   2280
gatccggaag tacacgatgc ggagactgct gcaggaaacg gagctggtgg agccgctgac   2340
acctagcgga gcgatgccca accaggcgca gatgcggatc ctgaaagaga cggagctgag   2400
gaaggtgaag gtgcttggat ctggcgcttt tggcacagtc tacaagggca tctggatccc   2460
tgatggggag aatgtgaaaa ttccagtggc catcaaagtg ttgagggaaa acacatcccc   2520
caaagccaac aaagaaatct tagacgaagc atacgtgatg ctggtgtggg ctccccata    2580 tgtctcccgc cttctgggca tctgcctgac atccacggtg cagctggtga cacagcttat   2640
gccctatggc tgcctcttag accatgtccg ggaaaaccgc ggacgcctgg ctcccagga    2700 cctgctgaac tggtgtatgc agattgccaa ggggatgagc tacctggagg atgtgcggct   2760
cgtacacagg gacttggccg ctcggaacgt gctggtcaag agtccaacc atgtcaaaat    2820 tacagacttc gggctggctc ggctgctgga cattgacgag acagagtacc atgcagatgg   2880
```

| | |
|---|---|
| gggcaaggtg cccatcaagt ggatggcgct ggagtccatt ctccgccggc ggttcaccca | 2940 |
| ccagagtgat gtgtggagtt atggtgtgac tgtgtgggag ctgatgactt ttggggccaa | 3000 |
| accttacgat gggatcccag cccgggagat ccctgacctg ctggaaaagg gggagcggct | 3060 |
| gccccagccc cccatctgca ccattgatgt ctacatgatc atggtcaaat gttggatgat | 3120 |
| tgactctgaa tgtcggccaa gattccggga gttggtgtct gaattctccc gcatggccag | 3180 |
| ggaccccag cgctttgtgg tcatccgaaa tgaggacttg ggcccagcca gtcccttgga | 3240 |
| cagcaccttc taccgctcac tgctggagga cgatgacatg ggggacctgg tggatgctga | 3300 |
| ggagtatctg gtaccccagc agggcttctt ctgtccagac cctgccccgg cgctgggg | 3360 |
| catggtccac cacaggcacc gcagctcatc taccaggagt ggcggtgggg acctgacact | 3420 |
| agggctggag ccctctgaag aggaggcccc caggtctcca ctggcaccct ccgaaggggc | 3480 |
| tggctccgat gtatttgatg gtgacctggg aatgggggca gccaaggggc tgcaaagcct | 3540 |
| ccccacacat gaccccagcc ctctacagcg gtacagtgag gacccacag tacccctgcc | 3600 |
| ctctgagact gatggctacg ttgcccccct gacctgcagc cccagcctg aatatgtgaa | 3660 |
| ccagccagat gttcggcccc agccccttc gccccgagag ggccctctgc ctgctgcccg | 3720 |
| acctgctggt gccactctgg aaaggcccaa gactctctcc ccagggaaga atgggggtcgt | 3780 |
| caaagacgtt tttgccttg ggggtgccgt ggagaacccc gagtacttga caccccaggg | 3840 |
| aggagctgcc cctcagcccc accctcctcc tgccttcagc ccagccttcg acaacctcta | 3900 |
| ttactgggac caggacccac cagagcgggg ggctccaccc agcaccttca aagggacacc | 3960 |
| tacggcagag aacccagagt acctgggtct ggacgtgcca gtgtgaacca gaaggccaag | 4020 |
| tccgcagaag ccctgatgtg tcctcaggga gcagggaagg cctgacttct gctggcatca | 4080 |
| agaggtggga gggccctccg accacttcca ggggaacctg ccatgccagg aacctgtcct | 4140 |
| aaggaacctt ccttcctgct tgagttccca gatggctgga aggggtccag cctcgttgga | 4200 |
| agaggaacag cactggggag tctttgtgga ttctgaggcc ctgcccaatg agactctagg | 4260 |
| gtccagtgga tgccacagcc cagcttggcc cttttccttcc agatcctggg tactgaaagc | 4320 |
| cttagggaag ctggcctgag aggggaagcg gccctaaggg agtgtctaag aacaaaagcg | 4380 |
| acccattcag agactgtccc tgaaacctag tactgccccc catgaggaag gaacagcaat | 4440 |
| ggtgtcagta tccaggcttt gtacagagtg cttttctgtt tagttttttac tttttttgtt | 4500 |
| ttgttttttt aaagatgaaa taaagaccca gggagaat gggtgttgta tggggaggca | 4560 |
| agtgtggggg gtccttctcc acacccactt tgtccatttg caaatatatt ttggaaaaca | 4620 |
| gcta | 4624 |

<210> SEQ ID NO 10
<211> LENGTH: 1847
<212> TYPE: DNA
<213> ORGANISM: Homo sapiens

<400> SEQUENCE: 10

| | |
|---|---|
| gtccccgcgc cagagacgca gccgcgctcc caccacccac acccaccgcg ccctcgttcg | 60 |
| cctcttctcc gggagccagt ccgcgccacc gccgccgccc aggccatcgc caccctccgc | 120 |
| agccatgtcc accaggtccg tgtcctcgtc ctcctaccgc aggatgttcg gcggcccggg | 180 |
| caccgcgagc cggccgagct ccagccggag ctacgtgact acgtccaccc gcacctacag | 240 |
| cctgggcagc gcgctgcgcc ccagcaccag ccgcagcctc tacgcctcgt ccccgggcgg | 300 |
| cgtgtatgcc acgcgctcct ctgccgtgcg cctgcggagc agcgtgcccg ggtgcggct | 360 |

-continued

```
cctgcaggac tcggtggact tctcgctggc cgacgccatc aacaccgagt tcaagaacac      420
ccgcaccaac gagaaggtgg agctgcagga gctgaatgac cgcttcgcca actacatcga      480
caaggtgcgc ttcctggagc agcagaataa gatcctgctg gccgagctcg agcagctcaa      540
gggccaaggc aagtcgcgcc tgggggacct ctacgaggag gagatgcggg agctgcgccg      600
gcaggtggac cagctaacca cgacaaagcc ccgcgtcgag gtggagcgcg acaacctggc      660
cgaggacatc atgcgcctcc gggagaaatt gcaggaggag atgcttcaga gagaggaagc      720
cgaaaacacc ctgcaatctt tcagacagga tgttgacaat gcgtctctgg cacgtcttga      780
ccttgaacgc aaagtggaat ctttgcaaga agagattgcc ttttgaaga aactccacga      840 agaggaaatc caggagctgc aggctcagat tcaggaacag catgtccaaa tcgatgtgga      900
tgtttccaag cctgacctca cggctgccct cgtgacgta cgtcagcaat atgaaagtgt      960
ggctgccaag aacctgcagg aggcagaaga atggtacaaa tccaagtttg ctgacctctc     1020
tgaggctgcc aaccggaaca atgacgccct gcgccaggca aagcaggagt ccactgagta     1080
ccggagacag gtgcagtccc tcacctgtga agtggatgcc cttaaaggaa ccaatgagtc     1140
cctggaacgc cagatgcgtg aaatggaaga gaactttgcc gttgaagctg ctaactacca     1200
agacactatt ggccgcctgc aggatgagat tcagaatatg aaggaggaaa tggctcgtca     1260
ccttcgtgaa taccaagacc tgctcaatgt taagatggcc cttgacattg agattgccac     1320
ctacaggaag ctgctggaag gcgaggagag caggatttct ctgcctcttc caaacttttc     1380
ctccctgaac ctgagggaaa ctaatctgga ttcactccct ctggttgata cccactcaaa     1440
aaggacactt ctgattaaga cggttgaaac tagagatgga caggttatca acgaaacttc     1500
tcagcatcac gatgaccttg aataaaaatt gcacacactc agtgcagcaa tatattacca     1560
gcaagaataa aaagaaatc catatcttaa agaaacagct ttcaagtgcc tttctgcagt     1620
ttttcaggag cgcaagatag atttggaata ggaataagct ctagttctta acaaccgaca     1680
ctcctacaag atttagaaaa aagtttacaa cataatctag tttacagaaa aatcttgtgc     1740
tagaatactt tttaaaaggt attttgaata ccattaaaac tgcttttttt tttccagcaa     1800
gtatccaacc aacttggttc tgcttcaata aatctttgga aaaactc                   1847
```

<210> SEQ ID NO 11
<211> LENGTH: 2301
<212> TYPE: DNA
<213> ORGANISM: Homo sapiens

<400> SEQUENCE: 11

```
tcgacagctc tctcgcccag cccagttctg gaagggataa aaggggggca tcaccgttcc       60
tgggtaacag agccaccttc tgcgtcctgc tgagctctgt tctctccagc acctcccaac      120
ccactagtgc ctggttctct tgctccacca ggaacaagcc accatgtctc gccagtcaag      180
tgtgtccttc cggagcgggg gcagtcgtag cttcagcacc gcctctgcca tcaccccgtc      240
tgtctcccgc accagcttca cctccgtgtc ccggtccggg gtggcggtg gtggtggctt      300 cggcagggtc agccttgcgg gtgcttgtgg agtgggtggc tatggcagcc ggagcctcta      360
caacctgggg ggctccaaga ggatatccat cagcactaga ggaggcagct tcaggaaccg      420
gtttggtgct ggtgctggag gcggctatgg ctttggaggt ggtgccggta gtggatttgg      480
tttcggcggt ggagctggtg gtggctttgg gctcggtggc ggagctggct ttggaggtgg      540
cttcggtggc cctggctttc ctgtctgcc tcctggaggt atccaagagg tcactgtcaa      600
ccagagtctc ctgactcccc tcaacctgca aatcgacccc agcatccaga gggtgaggac      660
```

| | |
|---|---|
| cgaggagcgc gagcagatca agaccctcaa caataagttt gcctccttca tcgacaaggt | 720 |
| gcggttcctg gagcagcaga acaaggttct ggacaccaag tggaccctgc tgcaggagca | 780 |
| gggcaccaag actgtgaggc agaacctgga gccgttgttc gagcagtaca tcaacaacct | 840 |
| caggaggcag ctggacagca tcgtggggga acggggccgc ctggactcag agctgagaaa | 900 |
| catgcaggac ctggtggaag acttcaagaa caagtatgag gatgaaatca acaagcgtac | 960 |
| cactgctgag aatgagtttg tgatgctgaa gaaggatgta gatgctgcct acatgaacaa | 1020 |
| ggtggagctg gaggccaagg ttgatgcact gatggatgag attaacttca tgaagatgtt | 1080 |
| ctttgatgcg gagctgtccc agatgcagac gcatgtctct gacacctcag tggtcctctc | 1140 |
| catggacaac aaccgcaacc tggacctgga tagcatcatc gctgaggtca aggcccagta | 1200 |
| tgaggagatt gccaaccgca gccgacagaa agccgagtcc tggtatcaga ccaagtatga | 1260 |
| ggagctgcag cagacagctg gccggcatgg cgatgacctc cgcaacacca agcatgagat | 1320 |
| cacagagatg aaccggatga tccagaggct gagagccgag attgacaatg tcaagaaaca | 1380 |
| gtgcgccaat ctgcagaacg ccattgcgga tgccgagcag cgtggggagc tggccctcaa | 1440 |
| ggatgccagg aacaagctgg ccgagctgga ggaggccctg cagaaggcca gcaggacat | 1500 |
| ggcccggctg ctgcgtgagt accaggagct catgaacacc aagctggccc tggacgtgga | 1560 |
| gatcgccact taccgcaagc tgctggaggg cgaggaatgc agactcagtg agaaggagt | 1620 |
| tggaccagtc aacatctctg ttgtcacaag cagtgtttcc tctggatatg gcagtggcag | 1680 |
| tggctatggc ggtggcctcg gtggaggtct tggcggcggc ctcggtggag gtcttgccgg | 1740 |
| aggtagcagt ggaagctact actccagcag cagtgggggt gtcggcctag gtggtgggct | 1800 |
| cagtgtgggg ggctctggct tcagtgcaag cagtggccga gggctggggg tgggctttgg | 1860 |
| cagtggcggg ggtagcagct ccagcgtcaa atttgtctcc accacctcct cctcccggaa | 1920 |
| gagcttcaag agctaagaac ctgctgcaag tcactgcctt ccaagtgcag caacccagcc | 1980 |
| catggagatt gcctcttcta ggcagttgct caagccatgt tttatccttt tctggagagt | 2040 |
| agtctagacc aagccaattg cagaaccaca ttctttggtt cccaggagag ccccattccc | 2100 |
| agccctggt ctcccgtgcc gcagttctat attctgcttc aaatcagcct tcaggtttcc | 2160 |
| cacagcatgg cccctgctga cacgagaacc caagttttc ccaaatctaa atcatcaaaa | 2220 |
| cagaatcccc accccaatcc caatttttgt tttggttcta actacctcca gaatgtgttc | 2280 |
| aataaaatgc tttttataata t | 2301 |

<210> SEQ ID NO 12
<211> LENGTH: 1512
<212> TYPE: DNA
<213> ORGANISM: Homo sapiens

<400> SEQUENCE: 12

| | |
|---|---|
| ctcctctcca gcccttctcc tgtgtgcctg cctcctgccg ccgccaccat gaccacctcc | 60 |
| atccgccagt tcacctcctc cagctccatc aagggctcct ccggcctggg gggcggctcg | 120 |
| tcccgcacct cctgccggct gtctggcggc ctgggtgccg gctcctgcag gctgggatct | 180 |
| gctggcggcc tggcagcac cctcgggggt agcagctact ccagctgcta cagctttggc | 240 |
| tctggtggtg gctatggcag cagctttggg ggtgttgatg ggctgctggc tggaggtgag | 300 |
| aaggccacca tgcagaacct caatgaccgc ctggcctcct acctggacaa ggtgcgtgcc | 360 |
| ctggaggagg ccaacactga gctggaggtg aagatccgtg actggtacca gaggcaggcc | 420 |
| ccgggggcccg cccgtgacta cagccagtac tacaggacaa ttgaggagct gcagaacaag | 480 |

| | |
|---|---|
| atcctcacag ccaccgtgga caatgccaac atcctgctac agattgacaa tgcccgtctg | 540 |
| gctgctgatg acttccgcac caagtttgag acagagcagg ccctgcgcct gagtgtggag | 600 |
| gccgacatca atggcctgcg cagggtgctg gatgagctga ccctggccag agccgacctg | 660 |
| gagatgcaga ttgagaacct caaggaggag ctggcctacc tgaagaagaa ccacgaggag | 720 |
| gagatgaacg ccctgcgagg ccaggtgggt ggtgagatca atgtggagat ggacgctgcc | 780 |
| ccaggcgtgg acctgagccg catcctcaac gagatgcgtg accagtatga aagatggca | 840 |
| gagaagaacc gcaaggatgc cgaggattgg ttcttcagca agacagagga actgaaccgc | 900 |
| gaggtggcca ccaacagtga gctggtgcag agtggcaaga gtgagatctc ggagctccgg | 960 |
| cgcaccatgc aggccttgga gatagagctg cagtcccagc tcagcatgaa agcatccctg | 1020 |
| gagggcaacc tggcggagac agagaaccgc tactgcgtgc agctgtccca gatccagggg | 1080 |
| ctgattggca gcgtggagga gcagctggcc cagcttcgct gcgagatgga gcagcagaac | 1140 |
| caggaataca aaatcctgct ggatgtgaag acgcggctgg agcaggagat tgccacctac | 1200 |
| cgccgcctgc tggagggaga ggatgcccac ctgactcagt acaagaaaga accggtgacc | 1260 |
| acccgtcagg tgcgtaccat tgtggaagag gtccaggatg gcaaggtcat ctcctcccgc | 1320 |
| gagcaggtcc accagaccac ccgctgagga ctcagctacc ccggccggcc acccaggagg | 1380 |
| cagggagcag ccgcccatc tgccccacag tctccggcct ctccagcctc agccctgc | 1440 |
| ttcagtccct tccccatgct tccttgcctg atgacaataa agcttgttga ctcagctaaa | 1500 |
| aaaaaaaaaa aa | 1512 |

<210> SEQ ID NO 13
<211> LENGTH: 1788
<212> TYPE: DNA
<213> ORGANISM: Homo sapiens

<400> SEQUENCE: 13

| | |
|---|---|
| attcctgaga gctctcctca ccaagaagca gcttctccgc tccttctagg atctccgcct | 60 |
| ggttcggccc gcctgcctcc actcctgcct ctaccatgtc catcagggtg acccagaagt | 120 |
| cctacaaggt gtccacctct ggcccccggg ccttcagcag ccgctcctac acgagtgggc | 180 |
| ccggttcccg catcagctcc tcgagcttct cccgagtggg cagcagcaac tttcgcggtg | 240 |
| gcctgggcgg cggctatggt ggggccagcg gcatggaggg catcaccgca gttacggtca | 300 |
| accagagcct gctgagcccc cttgtcctgg aggtggaccc caacatccag gccgtgcgca | 360 |
| cccaggagaa ggagcagatc aagaccctca acaacaagtt tgcctccttc atagacaagg | 420 |
| tacggttcct ggagcagcag aacaagatgc tggagaccaa gtggagcctc ctgcagcagc | 480 |
| agaagacggc tcgaagcaac atggacaaca tgttcgagag ctacatcaac aaccttaggc | 540 |
| ggcagctgga gactctgggc caggagaagc tgaagctgga ggcggagctt ggcaacatgc | 600 |
| aggggctggt ggaggacttc aagaacaagt atgaggatga gatcaataag cgtacagaga | 660 |
| tggagaacga atttgtcctc atcaagaagg atgtggatga agcttacatg aacaaggtag | 720 |
| agctggagtc tcgcctggaa gggctgaccg acgagatcaa cttcctcagg cagctatatg | 780 |
| aagaggagat ccgggagctg cagtcccaga tctcggacac atctgtggtg ctgtccatgg | 840 |
| acaacagccg ctccctggac atggacagca tcattgctga ggtcaaggca cagtacgagg | 900 |
| atattgccaa ccgcagccgg gctgaggctg agagcatgta ccagatcaag tatgaggagc | 960 |
| tgcagagcct ggctgggaag cacggggatg acctgcggcg cacaaagact gagatctctg | 1020 |
| agatgaaccg gaacatcagc cggctccagg ctgagattga gggcctcaaa ggccagaggg | 1080 |

-continued

| | | |
|---|---|---|
| cttccctgga ggccgccatt gcagatgccg agcagcgtgg agagctggcc attaaggatg | 1140 | |
| ccaacgccaa gttgtccgag ctggaggccg ccctgcagcg ggccaagcag acatggcgc | 1200 | |
| ggcagctgcg tgagtaccag gagctgatga acgtcaagct ggccctggac atcgagatcg | 1260 | |
| ccacctacag gaagctgctg gagggcgagg agagccggct ggagtctggg atgcagaaca | 1320 | |
| tgagtattca tacgaagacc accagcggct atgcaggtgg tctgagctcg gcctatgggg | 1380 | |
| gcctcacaag ccccggcctc agctacagcc tgggctccag cttttggctct ggcgcgggct | 1440 | |
| ccagctcctt cagccgcacc agctcctcca gggccgtggt tgtgaagaag atcgagacac | 1500 | |
| gtgatgggaa gctggtgtct gagtcctctg acgtcctgcc caagtgaaca gctgcggcag | 1560 | |
| cccctcccag cctaccctc ctgcgctgcc ccagagcctg ggaaggaggc cgctatgcag | 1620 | |
| ggtagcactg gaacaggag acccacctga ggctcagccc tagccctcag cccacctggg | 1680 | |
| gagtttacta cctggggacc ccccttgccc atgcctccag ctacaaaaca attcaattgc | 1740 | |
| ttttttttt tggtccaaaa taaaacctca gctagctctg ccaatgtc | 1788 | |

<210> SEQ ID NO 14
<211> LENGTH: 1439
<212> TYPE: DNA
<213> ORGANISM: Homo sapiens

<400> SEQUENCE: 14

| | | |
|---|---|---|
| gcagcctcga gggccaacaa cacctgctgt ccgtgtccat gcccggttgg ccaccccgtt | 60 | |
| tctgggggca tgagcttcac cactcgctcc accttctcca ccaactaccg gtccctgggc | 120 | |
| tctgtccagg cgcccagcta cggcgcccgg ccggtcagca gcgcggccag cgtctatgca | 180 | |
| ggcgctgggg gctctggttc ccggatctcc gtgtcccgct ccaccagctt caggggcggc | 240 | |
| atgggggtccg ggggcctggc caccgggata gccggggggtc tggcaggaat gggaggcatc | 300 | |
| cagaacgaga aggagaccat gcaaagcctg aacgaccgcc tggcctctta cctggacaga | 360 | |
| gtgaggagcc tggagaccga gaaccggagg ctggagagca aaatccggga gcacttggag | 420 | |
| aagaagggac cccaggtcag agactggagc cattacttca gatcatcga ggacctgagg | 480 | |
| gctcagatct tcgcaaatac tgtggacaat gcccgcatcg ttctgcagat tgacaatgcc | 540 | |
| cgtcttgctg ctgatgactt tagagtcaag tatgagacag agctggccat cgccagtct | 600 | |
| gtggagaacg acatccatgg gctccgcaag gtcattgatg acaccaatat cacacgactg | 660 | |
| cagctggaga cagagatcga ggctctcaag gaggagctgc tcttcatgaa gaagaaccac | 720 | |
| gaagaggaag taaaaggcct acaagcccag attgccagct ctgggttgac cgtggaggta | 780 | |
| gatgccccca atctcaggga cctcgccaag atcatggcag acatccgggc ccaatatgac | 840 | |
| gagctggctc ggaagaaccg agaggagcta gacaagtact ggtctcagca gattgaggag | 900 | |
| agcaccacag tggtcaccac acagtctgct gaggttggag ctgctgagac gacgctcaca | 960 | |
| gagctgagac gtacagtcca gtccttggag atcgacctgg actccatgag aaatctgaag | 1020 | |
| gccagcttgg agaacagcct gagggaggtg gaggcccgct acgccctaca gatggagcag | 1080 | |
| ctcaacggga tcctgctgca ccttgagtca gagctggcac agaccgggc agagggacag | 1140 | |
| cgccaggccc aggagtatga ggccctgctg aacatcaagg tcaagctgga ggctgagatc | 1200 | |
| gccacctacc gccgcctgct ggaagatggc gaggacttta tcttggtga tgccttggac | 1260 | |
| agcagcaact ccatgcaaac catccaaaag accaccaccc gccggatagt ggatggcaaa | 1320 | |
| gtggtgtctg agaccaatga caccaaagtt ctgaggcatt aagccagcag aagcagggta | 1380 | |
| cccctttgggg agcaggaggc caataaaaag ttcagagttc aaaaaaaaaa aaaaaaaa | 1439 | |

<210> SEQ ID NO 15
<211> LENGTH: 2420
<212> TYPE: DNA
<213> ORGANISM: Homo sapiens

<400> SEQUENCE: 15

| | | | | | |
|---|---|---|---|---|---|
| tccgggcgg | ccccggcag | ccagcgcgac | gttccaaaat | cgaacctcag | tggcggcgct | 60 |
| cggaagcgga | actctgccgg | ggccgcgccg | gctacattgt | ttcctccccc | cgactccctc | 120 |
| ccgccccctt | ccccgcctt | tcttccctcc | gcgacccggg | ccgtgcgtcc | gtcccctgc | 180 |
| ctctgcctgg | cggtccctcc | tccctctcc | ttgcacccat | acctctttgt | accgcacccc | 240 |
| ctggggaccc | ctgcgcccct | cccctccccc | ctgaccgcat | ggaccgtccc | gcaggccgct | 300 |
| gatgccgccc | gcggcgaggt | ggcccggacc | gcagtgcccc | aagagagctc | taatggtacc | 360 |
| aagtgacagg | ttggctttac | tgtgactcgg | ggacgccaga | gctcctgaga | agatgtcagc | 420 |
| aatacaggcc | gcctggccat | ccggtacaga | atgtattgcc | aagtacaact | tccacggcac | 480 |
| tgccgagcag | gacctgccct | tctgcaaagg | agacgtgctc | accattgtgg | ccgtcaccaa | 540 |
| ggaccccaac | tggtacaaag | ccaaaaacaa | ggtgggccgt | gagggcatca | tcccagccaa | 600 |
| ctacgtccaa | aagcgggagg | gcgtgaaggc | gggtaccaaa | ctcagcctca | tgccttggtt | 660 |
| ccacggcaag | atcacacggg | agcaggctga | gcggcttctg | tacccgccgg | agacaggcct | 720 |
| gttcctggtg | cgggagagca | ccaactaccc | cggagactac | acgctgtgcg | tgagctgcga | 780 |
| cggcaaggtg | gagcactacc | gcatcatgta | ccatgccagc | aagctcagca | tcgacgagga | 840 |
| ggtgtacttt | gagaacctca | tgcagctggt | ggagcactac | acctcagacg | cagatggact | 900 |
| ctgtacgcgc | ctcattaaac | caaaggtcat | ggagggcaca | gtggcggccc | aggatgagtt | 960 |
| ctaccgcagc | ggctgggccc | tgaacatgaa | ggagctgaag | ctgctgcaga | ccatcgggaa | 1020 |
| gggggagttc | ggagacgtga | tgctgggcga | ttaccgaggg | aacaaagtcg | ccgtcaagtg | 1080 |
| cattaagaac | gacgccactg | cccaggcctt | cctggctgaa | gcctcagtca | tgacgcaact | 1140 |
| gcggcatagc | aacctggtgc | agctcctggg | cgtgatcgtg | gaggagaagg | gcgggctcta | 1200 |
| catcgtcact | gagtacatgg | ccaagggag | ccttgtggac | tacctgcggt | ctaggggtcg | 1260 |
| gtcagtgctg | ggcggagact | gtctcctcaa | gttctcgcta | gatgtctgcg | aggccatgga | 1320 |
| atacctggag | ggcaacaatt | tcgtgcatcg | agacctggct | gcccgcaatg | tgctggtgtc | 1380 |
| tgaggacaac | gtggccaagg | tcagcgactt | tggtctcacc | aaggaggcgt | ccagcaccca | 1440 |
| ggacacgggc | aagctgccag | tcaagtggac | agccctgag | gccctgagag | agaagaaatt | 1500 |
| ctccactaag | tctgacgtgt | ggagtttcgg | aatccttctc | tgggaaatct | actcctttgg | 1560 |
| gcgagtgcct | tatccaagaa | ttcccctgaa | ggacgtcgtc | cctcgggtgg | agaagggcta | 1620 |
| caagatggat | gcccccgacg | gctgcccgcc | cgcagtctat | gaagtcatga | agaactgctg | 1680 |
| gcacctggac | gccgccatgc | ggccctcctt | cctacagctc | cgagagcagc | ttgagcacat | 1740 |
| caaaacccac | gagctgcacc | tgtgacggct | ggcctccgcc | tgggtcatgg | gcctgtgggg | 1800 |
| actgaacctg | gaagatcatg | gacctggtgc | cctgctcac | tgggcccgag | cctgaactga | 1860 |
| gccccagcgg | gctggcgggc | ctttttcctg | cgtcccagcc | tgcaccctc | cggccccgtc | 1920 |
| tctcttggac | ccaccgtggg | ggcctgggga | gccactgag | gggccaggga | ggaaggaggc | 1980 |
| cacggagcgg | gcggcagcgc | cccaccacgt | cgggcttccc | tggcctcccg | ccactcgcct | 2040 |
| tcttagagtt | ttattccttt | cctttttgga | gatttttttt | ccgtgtgttt | atttttatt | 2100 |
| attttttcaag | ataaggagaa | agaaagtacc | cagcaaatgg | gcattttaca | agaagtacga | 2160 |
| atcttatttt | tcctgtcctg | cccgtgaggt | ggggggggacc | gggcccctct | ctagggaccc | 2220 |

| | |
|---|---:|
| ctcgccccag cctcattccc cattctgtgt cccatgtccc gtgtctcctc ggtcgcccccg | 2280 |
| tgtttgcgct tgaccatgtt gcactgtttg catgcgcccg aggcagacgt ctgtcagggg | 2340 |
| cttggatttc gtgtgccgct gccacccgcc cacccgcctt gtgagatgga atcgtaataa | 2400 |
| accacgccat gaggaaaaaa | 2420 |

<210> SEQ ID NO 16
<211> LENGTH: 5527
<212> TYPE: DNA
<213> ORGANISM: Homo sapiens

<400> SEQUENCE: 16

| | |
|---|---:|
| cgcggccgcc ctgggcgggc gcgggcggcg ggcggcggtg agggcggcct gcggggcggc | 60 |
| gcccggggc cggccgagc cgggcctgag ccgggcccgg accgagctgg gagagggggct | 120 |
| ccggcccgat cgttcgcttg gcgcaaaatg ttggagatct gcctgaagct ggtgggctgc | 180 |
| aaatccaaga gggggctgtc ctcgtcctcc agctgttatc tggaagaagc ccttcagcgg | 240 |
| ccagtagcat ctgactttga gcctcagggt ctgagtgaag ccgctcgttg gaactccaag | 300 |
| gaaaaccttc tcgctggacc cagtgaaaat gaccccaacc ttttcgttgc actgtatgat | 360 |
| tttgtggcca gtgagataaa cactctaagc ataactaaag gtgaaaagct ccgggtctta | 420 |
| ggctataatc acaatgggga atggtgtgaa gcccaaacca aaaatggcca aggctgggtc | 480 |
| ccaagcaact acatcacgcc agtcaacagt ctggagaaac actcctggta ccatgggcct | 540 |
| gtgtcccgca atgccgctga gtatctgctg agcagcggga tcaatggcag cttcttggtg | 600 |
| cgtgagagtg agagcagtcc tggccagagg tccatctcgc tgagatacga agggagggtg | 660 |
| taccattaca ggatcaacac tgcttctgat ggcaagctct acgtctcctc cgagagccgc | 720 |
| ttcaacaccc tggccgagtt ggttcatcat cattcaacgg tggccgacgg gctcatcacc | 780 |
| acgctccatt atccagcccc aaagcgcaac aagcccactg tctatggtgt gtcccccaac | 840 |
| tacgacaagt gggagatgga acgcacggac atcaccatga gcacaagct gggcgggggc | 900 |
| cagtacgggg aggtgtacga gggcgtgtgg aagaaataca gcctgacggt ggccgtgaag | 960 |
| accttgaagg aggacaccat ggaggtggaa gagttcttga agaagctgc agtcatgaaa | 1020 |
| gagatcaaac accctaacct ggtgcagctc ctggggtct gcaccccggga gccccgttc | 1080 |
| tatatcatca ctgagttcat gacctacggg aacctcctgg actacctgag ggagtgcaac | 1140 |
| cggcaggagg tgaacgccgt ggtgctgctg tacatggcca ctcagatctc gtcagccatg | 1200 |
| gagtacctga gaagaaaaa cttcatccac agagatcttg ctgcccgaaa ctgcctggta | 1260 |
| ggggagaacc acttggtgaa ggtagctgat tttggcctga gcaggttgat gacaggggac | 1320 |
| acctacacag cccatgctgg agccaagttc cccatcaaat ggactgcacc cgagagcctg | 1380 |
| gcctacaaca agttctccat caagtccgac gtctgggcat ttggagtatt gctttgggaa | 1440 |
| attgctacct atggcatgtc cccttacccg ggaattgacc tgtcccaggt gtatgagctg | 1500 |
| ctagagaagg actaccgcat ggagcgccca gaaggctgcc cagagaaggt ctatgaactc | 1560 |
| atgcgagcat gttggcagtg gaatcctct gaccggccct cctttgctga aatccaccaa | 1620 |
| gcctttgaaa caatgttcca ggaatccagt atctcagacg aagtggaaaa ggagctgggg | 1680 |
| aaacaaggcg tccgtgggc tgtgagtacc ttgctgcagg cccagaagct gcccaccaag | 1740 |
| acgaggacct ccaggagagc tgcagagcac agagacacca ctgacgtgcc tgagatgcct | 1800 |
| cactccaagg gccagggaga gagcgatcct ctggaccatg agcctgccgt gtctccattg | 1860 |
| ctccctcgaa aagagcgagg tcccccggag ggcggcctga atgaagatga gcgccttctc | 1920 |

```
cccaaagaca aaaagaccaa cttgttcagc gccttgatca agaagaagaa gaagacagcc   1980
ccaacccctc ccaaacgcag cagctccttc cgggagatgg acggccagcc ggagcgcaga   2040
ggggccggcg aggaagaggg ccgagacatc agcaacgggg cactggcttt cacccccttg   2100
gacacagctg acccagccaa gtccccaaag cccagcaatg gggctggggt ccccaatgga   2160
gccctccggg agtccggggg ctcaggcttc cggtctcccc acctgtggaa gaagtccagc   2220
acgctgacca gcagccgcct agccaccggc gaggaggagg gcggtggcag ctccagcaag   2280
cgcttcctgc gctcttgctc cgcctcctgc gttccccatg gggccaagga cacggagtgg   2340
aggtcagtca cgctgcctcg ggacttgcag tccacgggaa gacagtttga ctcgtccaca   2400
tttggagggc acaaaagtga agccggct ctgcctcgga gagggcagg ggagaacagg   2460 tctgaccagg tgacccgagg cacagtaacg cctcccccca ggctggtgaa aaagaatgag   2520
gaagctgctg atgaggtctt caaagacatc atggagtcca gcccgggctc cagcccgccc   2580
aacctgactc caaacccct ccggcggcag gtcaccgtgg ccctgcctc gggcctcccc   2640 cacaaggaag aagctgaaaa gggcagtgcc ttagggaccc ctgctgcagc tgagccagtg   2700 accccccacca gcaaagcagg ctcaggtgca ccagggggca ccagcaaggg ccccgccgag   2760
gagtccagag tgaggaggca caagcactcc tctgagtcgc cagggaggga caaggggaaa   2820
ttgtccaggc tcaaacctgc cccgccgccc ccaccagcag cctctgcagg gaaggctgga   2880
ggaaagccct cgcagagccc gagccaggag gcggccgggg aggcagtcct gggcgcaaag   2940
acaaaagcca cgagtctggt tgatgctgtg aacagtgacg ctgccaagcc cagccagccg   3000
ggagagggcc tcaaaaagcc cgtgctcccg gccactccaa agccacagtc cgccaagccg   3060
tcggggaccc ccatcagccc agccccgtt ccctccacgt tgccatcagc atcctcggcc   3120
ctggcagggg accagccgtc ttccactgcc ttcatccctc tcatatcaac ccgagtgtct   3180
cttcggaaaa cccgccagcc tccagagcgg atcgccagcg cgccatcac caagggcgtg   3240 gtcctggaca gcaccgaggc gctgtgcctc gccatctcta ggaactccga gcagatggcc   3300
agccacagcg cagtgctgga ggccggcaaa aacctctaca cgttctgcgt gagctatgtg   3360
gattccatcc agcaaatgag gaacaagttt gccttccgag aggccatcaa caaactggag   3420
aataatctcc gggagcttca gatctgcccg gcgacagcag gcagtggtcc ggcggccact   3480
caggacttca gcaagctcct cagttcggtg aaggaaatca gtgacatagt gcagaggtag   3540
cagcagtcag gggtcaggtg tcaggcccgt cggagctgcc tgcagcacat gcgggctcgc   3600
ccatacccat gacagtggct gacaaggac tagtgagtca gccttggc ccaggagctc   3660 tgcgccaggc agagctgagg gccctgtgga gtccagctct actacctacg tttgcaccgc   3720
ctgccctccc gcaccttcct cctccccgct ccgtctctgt cctcgaattt tatctgtgga   3780
gttcctgctc cgtggactgc agtcggcatg ccaggacccg ccagccccgc tcccacctag   3840
tgccccagac tgagctctcc aggccaggtg gaacggctg atgtggactg tcttttcat   3900 tttttctct ctggagcccc tcctccccg gctgggcctc cttcttccac ttctccaaga   3960
atggaagcct gaactgaggc cttgtgtgtc aggccctctg cctgcactcc ctggccttgc   4020
ccgtcgtgtg ctgaagacat gtttcaagaa ccgccatttc gggaagggca tgcacgggcc   4080
atgcacacgg ctggtcactc tgccctctgc tgctgcccgg ggtggggtgc actcgccatt   4140
tcctcacgtg caggacagct cttgatttgg gtgaaaaaca gggtgctaaa gccaaccagc   4200 cttttgggtcc tgggcaggtg ggagctgaaa aggatcgagg catggggcat gtcctttcca   4260
tctgtccaca tccccagagc ccagctcttg ctctcttgtg acgtgcactg tgaatcctgg   4320
```

```
caagaaagct tgagtctcaa gggtggcagg tcactgtcac tgccgacatc cctcccccag    4380
cagaatggag gcaggggaca agggaggcag tggctagtgg ggtgaacagc tggtgccaaa    4440
tagccccaga ctgggcccag gcaggtctgc aagggcccag agtgaaccgt cctttcacac    4500
atctgggtgc cctgaaggc ccttcccctc ccccactcct ctaagacaaa gtagattctt    4560
acaaggccct ttcctttgga acaagacagc cttcactttt ctgagttctt gaagcatttc    4620
aaagccctgc ctctgtgtag ccgccctgag agagaataga gctgccactg ggcacctcgc    4680
gacaggtggg aggaaagggc ctgcgcagtc ctggtcctgg ctgcactctt gaactgggcg    4740
aatgtcttat ttaattaccg tgagtgacat agcctcatgt tctgtggggg tcatcaggga    4800
gggttaggaa aaccacaaac ggagcccctg aaagcctcac gtatttcaca gagcacgcct    4860
gccatcttct ccccgaggct gccccaggcc ggagcccaga taccggcggg ctgtgactct    4920
gggcagggac ccggggtctc ctggaccttg acagagcagc taactccgag agcagtgggc    4980
aggtggccgc ccctgaggct tcacgccgga gaagccacct tcccgcccct tcataccgcc    5040
tcgtgccagc agcctcgcac aggccctagc tttacgctca tcacctaaac ttgtacttta    5100
tttttctgat agaaatggtt tcctctggat cgttttatgc ggttcttaca gcacatcacc    5160
tctttccccc cgacggctgt gacgcagcgg agaggcacta gtcaccgaca gcggccttga    5220
agacagagca aagcccccac ccaggtcccc cgactgcctg tctccatgag gtactggtcc    5280
cttccttttg ttaacgtgat gtgccactat attttacacg tatctcttgg tatgcatctt    5340
ttatagacgc tcttttctaa gtggcgtgtg catagcgtcc tgccctgccc tcggggggcct    5400 gtggtggctc cccctctgct tctcggggtc cagtgcattt tgtttctgta tatgattctc    5460
tgtggttttt tttgaatcca aatctgtcct ctgtagtatt ttttaaataa atcagtgttt    5520
acattag                                                               5527
```

MOESIN, CAVEOLIN 1 AND YES ASSOCIATED PROTEIN 1 AS PREDICTIVE MARKERS OF RESPONSE TO DASATINIB IN BREAST CANCERS

CROSS-REFERENCE TO RELATED APPLICATIONS

This application is the National Stage of International Application No. PCT/US2006/060776, filed Nov. 10, 2006, which claims the benefit of U.S. Provisional Application No. 60/735,475, filed Nov. 10, 2005, the disclosures of which are incorporated herein by reference in their entireties.

FIELD OF THE INVENTION

The invention described herein relates to methods and compositions useful in the diagnosis, treatment and management of cancers that express particular genes.

BACKGROUND OF THE INVENTION

Cancer is the second leading cause of human death next to coronary disease. Worldwide, millions of people die from cancer every year. In the United States alone, cancer causes the death of well over a half-million people annually, with some 1.4 million new cases diagnosed per year. While deaths from heart disease have been declining significantly, those resulting from cancer generally are on the rise.

Worldwide, several cancers stand out as the leading killers. In particular, carcinomas of the breast, lung, prostate, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered and many cancer patients experience a recurrence.

Breast cancer affects over one million women worldwide every year (see, e.g., Jemal A et al., 2002. CA Cancer J. Clin. 2002 January-February; 52(1):23-47; Jensen O M, et al., Eur. J. Cancer. 1990; 26(11-12):1167-256; and National Cancer Institute of Canada: Canadian Cancer Statistics 1996. Toronto, Canada. 1996; 21-23). Breast cancer is also one of the leading causes of death among women, with the cumulative lifetime risk of a woman developing breast cancer estimated to be 1 in 9. Understanding the origins and subtypes of these malignancies as well as models for the identification of new diagnostic and therapeutic modalities is of significant interest to health care professionals. Most women that die from breast cancer succumb not to the original primary disease, which is usually amenable to various therapies, but rather from metastatic spread of the breast cancer to distant sites. This fact underscores the need to develop both additional diagnostic methods as well as novel anticancer agents or more aggressive forms of therapy directed specifically against breast tumor subtypes.

Advances in the understanding of the biology of this disease, however, have led to improved patient survival with incorporation of new anti-hormonal agents in the treatment of hormone receptor positive disease and the addition of HER2 directed therapies for the 25% of women with HER2 amplification (see, e.g., Fossati R, et al., J. Clin. Oncol. 1998 October; 16(10):3439-60 and Slamon D J, et al., N Engl J. Med. 2001 Mar. 15; 344(11):783-92).

There remains however, a subset of women for whom these approaches are not an effective option and chemotherapy offers only limited benefits. This group has been described as "triple negative" (i.e. estrogen receptor negative (SEQ ID NO: 7), progesterone receptor negative (SEQ ID NO: 8), and HER2 negative (SEQ ID NO: 9)) and represents a distinct clinical and molecular subgroup of the disease.

Recent studies using gene expression profiling have identified this group as expressing unique cytokeratins that differentiate it from other types of breast cancer and as having a similar poor prognosis to the HER-2 positive group prior to the introduction of trastuzumab (see, e.g., Sorlie T et al., Proc Natl Acad Sci USA. 2001 Sep. 11; 98: 10869-74; Sotiriou C, et al., Proc Natl Acad Sci USA. 2003 September 2; 100(18): 10393-8; and Perou C M, et al., Nature. 2000 Aug. 17; 406 (6796):747-52). The profiling data have subgrouped the disease into "luminal", expressing specific cytokeratins (CK8, CK18) associated with the luminal layer in the normal breast epithelium, or the "basal" group based on the expression of cytokeratins (CK5, CK17) found in the basal layer of the breast epithelium. ER+ and HER2 amplified disease may occur in both subtypes, whereas the "triple negative" breast cancers are generally of the basal subtype (see, e.g., Sorlie T et al., Proc Natl Acad Sci USA. 2001 Sep. 11; 98: 10869-74; Sotiriou C, et al., Proc Natl Acad Sci USA. 2003 Sep. 2; 100(18): 10393-8; Perou C M, et al., Nature. 2000 Aug. 17; 406(6796):747-52; and Wilson Ca et al., Breast Cancer Res. 2004; 6(5):192-200). In addition, there exists a subset of "triple negative" breast cancers that also express vimentin. This group is felt to represent a group of breast cancers that has undergone an epithelial-to-mesenchymal transition (EMT) and has been associated with clinical disease that is more invasive, has a higher mitotic index, and also has a worse clinical outcome (see, e.g., Thomas P A, et al., Clin Cancer Res. 1999 October; 5(10):2698-703 and Laakso M, et al., Clin Cancer Res. 2006 Jul. 15; 12(14 Pt 1):4185-91). Taken together, these data demonstrate that the identification of new therapies with activity in the basal subtype of breast cancer is a clinical priority.

SUMMARY OF THE INVENTION

The present inventors have discovered that certain genes are differentially expressed in breast cancer subtypes that are sensitive to therapy with src kinase inhibitors. In particular, the present inventors have discovered that the moesin, caveolin 1, and yes-associated protein 1 genes are differentially expressed in breast cancer subtypes that are sensitive to therapy with N-(2-chloro-6-methylphenyl)-2-(6-(4-(2-hydroxyethyl)piperazin-1-yl)-2-methylpyrimidin-4-ylamino) thiazole-5-carboxamide.

As is known in the art, N-(2-chloro-6-methylphenyl)-2-[[6-[4-(2-hydroxyethyl)-1-piperazinyl]-2-methyl-4-pyrimidinyl]amino]-5-thiazolecarboxamide refers to a compound having the following structure (I):

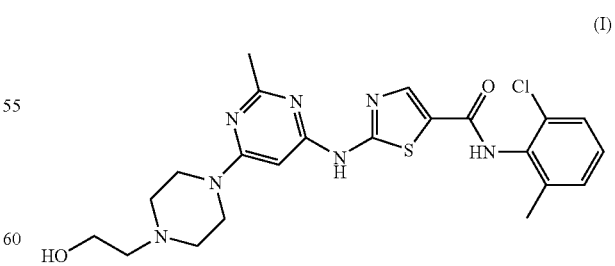

(I)

Compound (I) can also be referred to as N-(2-chloro-6-methylphenyl)-2-((6-(4-(2-hydroxyethyl)-1-piperazinyl)-2-methyl-4-pyrimidinyl)amino)-1,3-thiazole-5-carboxamide in accordance with IUPAC nomenclature. Use of the term encompasses (unless otherwise indicated) solvates (including hydrates) and polymorphic forms of the compound (I) or its salts (such as the monohydrate form of (I) described in U.S. Ser. No. 11/051,208, filed Feb. 4, 2005, incorporated herein by reference in its entirety and for all purposes. Pharmaceutical compositions of N-(2-chloro-6-methylphenyl)-2-[[6-[4-(2-hydroxyethyl)-1-piperazinyl]-2-methyl-4-pyrimidinyl]amino]-5-thiazolecarboxamide include all pharmaceutically acceptable compositions comprising N-(2-chloro-6-methylphenyl)-2-[[6-[4-(2-hydroxyethyl)-1-piperazinyl]-2-methyl-4-pyrimidinyl]amino]-5-thiazolecarboxamide and one or more diluents, vehicles and/or excipients, such as those compositions described in U.S. Ser. No. 11/402,502, filed Apr. 12, 2006, incorporated herein by reference in its entirety and for all purposes. One example of a pharmaceutical composition comprising N-(2-chloro-6-methylphenyl)-2-[[6-[4-(2-hydroxyethyl)-1-piperazinyl]-2-methyl-4-pyrimidinyl]amino]-5-thiazolecarboxamide is SPRYCEL™ (Bristol-Myers Squibb Company). SPRYCEL™ comprises N-(2-chloro-6-methylphenyl)-2-[[6-[4-(2-hydroxyethyl)-1-piperazinyl]-2-methyl-4-pyrimidinyl]amino]-5-thiazolecarboxamide as the active ingredient, also referred to as dasatinib, and as inactive ingredients or excipients, lactose monohydrate, microcrystalline cellulose, croscarmellose sodium, hydroxypropyl cellulose, and magnesium stearate in a tablet comprising hypromellose, titanium dioxide, and polyethylene glycol.

N-(2-chloro-6-methylphenyl)-2-[[6-[4-(2-hydroxyethyl)-1-piperazinyl]-2-methyl-4-pyrimidinyl]amino]-5-thiazolecarboxamide also known as dasatinib (BMS-354825) is a highly potent, oral multi-targeted kinase inhibitor that targets BCR-ABL and SRC kinases with IC50s for the isolated kinases of 0.55 and 3.0 nM, respectively. Dasatinib is an orally active small molecule kinase inhibitor of both the src and abl proteins. It is a thiazole- and pyrimidine-based SFK/Abl kinase inhibitor (see, e.g., Nam, Sangkil et al., Cancer Research 65, 9185-9189, Oct. 15, 2005; Lombardo L J et al., J Med Chem, 2004 Dec. 30; 47(27): 6658-61; and NDA 21-986, ODAC briefing document). Dasatinib also inhibits other oncogenic kinases such as c KIT, platelet-derived growth factor receptor, and ephrin A receptor kinases). In contrast to imatinib, which binds only to the inactive conformation, dasatinib binds to both the active or "opened" conformation and the inactive or "closed" conformation of the ABL kinase domain of BCR-ABL.

The structure and use of N-(2-chloro-6-methylphenyl)-2-[[6-[4-(2-hydroxyethyl)-1-piperazinyl]-2-methyl-4-pyrimidinyl]amino]-5-thiazolecarboxamide as an anticancer agent is described in Lombardo, L. J., et al., *J. Med. Chem.,* 47:6658-6661 (2004) and is described in the following U.S. patents and pending applications: U.S. Pat. No. 6,596,746, granted Jul. 22, 2003; U.S. Ser. No. 10/395,503, filed Mar. 24, 2003, all of which are incorporated by reference herein in their entirety.

The moesin, caveolin 1, and yes-associated protein 1 genes are herein referred to as the MCY gene set. MCY is a term used herein to refer to moesin, caveolin 1 or yes-associated protein 1 or any combination thereof. MCY polynucleotides refer to moesin, caveolin 1 or yes-associated protein 1 polynucleotides or any combination thereof (i.e., moesin polynucleotides; caveolin-1 polynucleotides; yes-associated protein 1 polynucleotides; moesin and caveolin-1 polynucleotides; moesin and yes-associated protein 1 polynucleotides; caveolin-1 and yes-associated protein 1 polynucleotides; and moesin, caveolin-1, and yes-associated protein 1 polynucleotides) and MCY polypeptides refer to moesin, caveolin 1 or yes-associated protein 1 polypeptides or any combination thereof (i.e., moesin polypeptides; caveolin-1 polypeptides; yes-associated protein 1 polypeptides; moesin and caveolin-1 polypeptides; moesin and yes-associated protein 1 polypeptides; caveolin-1 and yes-associated protein 1 polypeptides; and moesin, caveolin-1, and yes-associated protein 1 polypeptides).

It has been discovered that the majority of breast cancer cell lines sensitive to the chemotherapeutic molecule dasatinib represent the "non-luminal" subtype of breast cancer ("basal" and "mesenchymal"). Methods for examining the expression of the gene sets provided herein can be used to predict the response to agents such as N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt, solvate, or hydrate thereof in human breast cancer cells.

The present invention provides methods of identifying cells and individuals that are likely to respond or are responsive to therapy with N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof, or to therapy with another src kinase inhibitor, as well as methods of treating such individuals by tailoring their treatment regimen depending on whether or not they are responders to therapy with N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof.

Methods for identifying a cell that is likely to respond or is responsive to therapy with N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof are provided herein. These methods can comprise determining the level of expression of at least one gene selected from moesin, caveolin-1, or yes-associated protein 1 wherein the level of expression is indicative of whether the cell is sensitive to therapy with N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof. The methods include determining the level of expression of two genes selected from moesin, caveolin-1, or yes-associated protein 1 (i.e., moesin and caveolin-1, moesin and yes-associated protein 1, and caveolin-1 and yes-associated protein) and determining the level of expression of all three genes. In certain preferred embodiments, elevated levels of MCY polypeptides and/or polynucleotides are indicative of sensitivity to therapy with N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof.

The invention provides methods for detecting the expression of at least one gene, at least two genes, or all three genes in the MCY gene set. The methods include the detection of expression of the polynucleotides and proteins encoded by the polynucleotides in various biological samples (e.g. breast cancer biopsies), as well as methods for identifying cells that express at least one gene, at least two genes, or all three genes in the MCY gene set.

Methods for determining the level of MCY polypeptides or polynucleotides in a tissue sample having or suspected of having some form of growth disregutation such as that found in various breast cancers, for example the basal subtypes as described in Sorlie et al., PNAS (2001), 98(19): 10869-10874, which is incorporated herein by reference, are provided herein. Such methods can be used to predict sensitivity to N-(2-chloro-6-methylphenyl)-2-[[6-[4-(2-hydroxyethyl)-

1-piperazinyl]-2-methyl-4-pyrimidinyl]amino]-5-thiazole-carboxamide, or a pharmaceutically acceptable salt or hydrate thereof.

Also provided herein are methods of examining a test biological sample comprising a human breast cell for evidence of gene expression indicative of sensitivity to treatment with N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof by determining the levels of moesin, caveolin 1 and/or yes-associated protein 1 polynucleotides (MCY polynucleotides) that encode the MCY polypeptides, in the biological sample, wherein the levels of at least one of the MCY polynucleotides in the test sample is indicative of sensitivity to the treatment. In certain embodiments, the levels the MCY polynucleotides in the cell are determined by contacting the sample with a complementary polynucleotide that hybridizes to a nucleotide sequence shown in Table 1 (or a nucleotide sequence having substantial identity to a sequence shown in Table 1), or a complement thereof, and evaluating the presence of a hybridization complex formed by the hybridization of the MCY Polynucleotide with the complementary polynucleotide in the test biological sample. The levels of one of, two of, or all three of the MCY polynucleotides can be determined in this manner. In certain embodiments of the invention, the breast cancer is of a non-luminal subtype. In certain aspects, the breast cancer is of the mesenchymal or basal subtype. In certain preferred embodiments, elevated levels of MCY polynucleotides are indicative of sensitivity to therapy with N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof.

A related embodiment is a method of examining a human breast cell for evidence of gene expression indicative of sensitivity to treatment with N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof by determining the levels of a moesin and/or caveolin 1 and/or yes-associated protein 1 (including any combination thereof) polynucleotide that encodes a MCY polypeptide (e.g., such a polypeptide shown in Table 1) in the human breast cell, wherein expression of a MCY polynucleotide in the test sample is indicative of sensitivity to the treatment. In certain embodiments, the expression of a MCY polynucleotide in the human breast cell is determined by contacting at least one of the endogenous MCY polynucleotide sequences in the human breast cell with a complementary polynucleotide (e.g. a probe labeled with a detectable marker or a PCR primer) which specifically hybridizes to a MCY nucleotide sequence (e.g., a nucleotide sequence shown in Table 1 or having substantial identity to a nucleotide sequence in Table 1) and evaluating the presence of a hybridization complex formed by the hybridization of the MCY complementary polynucleotide with the MCY polynucleotide in the sample (e.g. via Northern analysis or PCR) so that evidence of sensitivity to N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof is examined. The levels of one of, two of, or all three of the MCY polynucleotides can be determined in this manner. Certain embodiments of the invention further include the step of examining the expression of other genes such as examining the levels of the polynucleotides provided in Tables 5a-h, Her-2 (SEQ ID NO: 9), estrogen receptor (SEQ ID NO: 7), progesterone receptor (SEQ ID NO: 8), BRCA1 and/or BRCA2 or the like in the test biological sample.

A related embodiment of the invention is a method of examining a human breast cell (e.g. from a biopsy) for evidence of gene expression indicative of sensitivity to N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof, the method comprising determining the levels of a moesin, and/or caveolin 1 and/or yes-associated protein 1 (including any combination thereof) polypeptide (e.g., a polypeptide having a sequence shown in Table 1 or substantial identity to a sequence as shown in Table 1) in the breast cell, wherein the level of the MCY polypeptide in the human breast cell provides evidence of sensitivity. In certain embodiments, the levels of the MCY polypeptide in the cell are determined by contacting the sample with an antibody (e.g. one labelled with a detectable marker) that immunospecifically binds to a MCY polypeptide sequence (e.g., a sequence shown in Table 1 or having substantial identity to a sequence shown in Table 1) and evaluating the presence of a complex formed by the binding of the antibody with the MCY polypeptide in the sample. The levels of one of, two of, or all three of the MCY polypeptides can be determined in this manner. In certain aspects, the presence of a complex is evaluated by a method selected from the group consisting of ELISA analysis, Western analysis and immunohistochemistry. In certain embodiments of the invention, the breast cancer is of a non-luminal subtype. In certain aspects, the breast cancer is of the mesenchymal or basal subtype. Certain embodiments of the invention further include the step of examining the expression and/or sequences of other polypeptides such as one or more polypeptides identified in Table 5a-h, Her-2, estrogen receptor, progesterone receptor, BRCA1 and/or BRCA2 or the like in the test biological sample. In certain preferred embodiments, elevated levels of MCY polypeptides are indicative of sensitivity to therapy with N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof.

Methods for determining the responsiveness of an individual with cancer to therapy with N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof are also provided herein. These methods can comprise determining the level of MCY polynucleotides or polypeptides wherein the level is indicative of whether the individual is sensitive to the therapy. These methods include determining the level of one MCY polynucleotide and/or polypeptide (i.e., determining the level of moesin polypeptides or moesin polynucleotides), determining the level of two MCY polynucleotides and/or polypeptides (i.e., determining the level of moesin and caveolin-1 polynucleotides and/or polypeptides; moesin and yes-associated protein 1 polynucleotides and/or polypeptides; and/or caveolin-1 and yes-associated protein polynucleotides and/or polypeptides) and/or determining the level of all three MCY polynucleotides and/or polypeptides. In certain preferred embodiments, elevated levels of MCY polypeptides and/or polynucleotides are indicative of the individual being a responder to therapy with N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof.

The present invention provides methods for screening a biological sample, for example, a biological sample comprising cells that do not respond, or that have stopped responding, or that have a diminished response, to therapy with N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof or alternative cancer therapies. For example, the present invention provides a method of screening cells from an individual suffering from cancer who is being treated with N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof or another therapy and whose cells do not respond or have stopped responding or have a diminished response to either of the drugs, for the level of MCY polynucleotides and/or polypeptides. These methods include determining the level of one MCY polynucleotide and/or polypeptide (i.e., determining the level of moesin polypeptides or moesin polynucleotides), determining the level of two MCY polynucleotides and/or polypeptides ((i.e., determining the level of moesin and caveolin-1 polynucleotides and/or polypeptides; moesin and yes-associated protein 1 polynucleotides and/or polypeptides; and/or caveolin-1 and yes-associated protein polynucleotides and/or polypeptides) and/or determining the level of all three MCY polynucleotides and/or polypeptides.

The present invention also provides methods of establishing a treatment regimen for an individual having cancer, and breast cancer, in particular. The treatment regimen can comprise the administration of N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof at different doses depending on the level of MCY polypeptides and/or polynucleotides in a biological sample obtained from the individual. These methods include determining the level of one MCY polynucleotide and/or polypeptide (i.e., determining the level of moesin polypeptides or moesin polynucleotides), determining the level of two MCY polynucleotides and/or polypeptides (i.e., determining the level of moesin and caveolin-1 polynucleotides and/or polypeptides; moesin and yes-associated protein 1 polynucleotides and/or polypeptides; and/or caveolin-1 and yes-associated protein polynucleotides and/or polypeptides) and/or determining the level of all three MCY polynucleotides and/or polypeptides.

The present invention also provides methods of treating an individual suffering from cancer (for example, breast cancer, including breast cancer of any type described herein) comprising detecting the level of MCY-polynucleotides and/or polypeptides in a biological sample obtained from the individual and administering N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof if the polypeptides and/or polynucleotides are present in the biological sample at an increased level as compared to a control sample. These methods can include the step of determining the level of one MCY polynucleotide and/or polypeptide (i.e., determining the level of moesin polypeptides or moesin polynucleotides), determining the level of two MCY polynucleotides and/or polypeptides ((i.e., determining the level of moesin and caveolin-1 polynucleotides and/or polypeptides; moesin and yes-associated protein 1 polynucleotides and/or polypeptides; and/or caveolin-1 and yes-associated protein polynucleotides and/or polypeptides) and/or determining the level of all three MCY polynucleotides and/or polypeptides.

The present invention also provides method for identifying an individual that has a cancer that is particularly aggressive and can be characterized as triple negative or of the basal subtype. The method comprises obtaining a biological sample from said individual and determining the level of expression of at least one, two, or three genes selected from moesin, caveolin-1, or yes-associated protein 1 in the biological sample. An increased level of expression of the at least one, two, or three genes is indicative of the cancer being particularly aggressive, triple negative and/or of the basal subtype. The level of expression of any combination of the three genes can be determined. In certain embodiments, if the individual is identified as having the particularly aggressive cancer, (i.e., triple negative cancer, cancer of the basal subtype), the method can further comprise the step of administering N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof to the individual.

The present invention also provides kits for characterizing mammalian cells and determining an individual's responsiveness to therapy with N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof. The kit can comprise a container, a label on said container, and a composition contained within said container; wherein the composition includes MCY polypeptide (and/or one or more polynucleotides identified in Tables a-h) specific antibodies and/or polynucleotides that hybridize to a complement of a MCY polynucleotide (e.g., a polynucleotide shown in Table 1) under stringent conditions or binds to a MCY polypeptide encoded by the MCY polynucleotide (e.g., such as shown in Table 1). In certain aspects, the label on said container will indicate that the composition can be used to determine the level of MCY protein, RNA or DNA in at least one type of mammalian cell, and instructions for using the MCY gene set antibody and/or polynucleotide for evaluating the presence of MCY protein, RNA or DNA in at least one type of mammalian cell.

While the MCY gene set is provided as an illustrative example of a set of genes whose expression can be correlated with sensitivity to drugs such as N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof, those of skill in the art will appreciate that the data provided herein relating to other genes, for example the genes having expression products as identified in Tables 5(a-h), is provided to demonstrate that this disclosure is to be used to select other groups of genes whose expression is also correlated with sensitivity to drugs such as N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof. Consequently, the discussions herein relating to the use of MCY set are simply provided as a typical example and this disclosure is further applicable to the data provided that relates to additional polynucleotides and polypeptides (for example those identified Tables 5(a-h) that can be examined to predict sensitivity to drugs such as N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof.

DETAILED DESCRIPTION OF ILLUSTRATIVE EMBODIMENTS

I. Introduction

Figure 1:
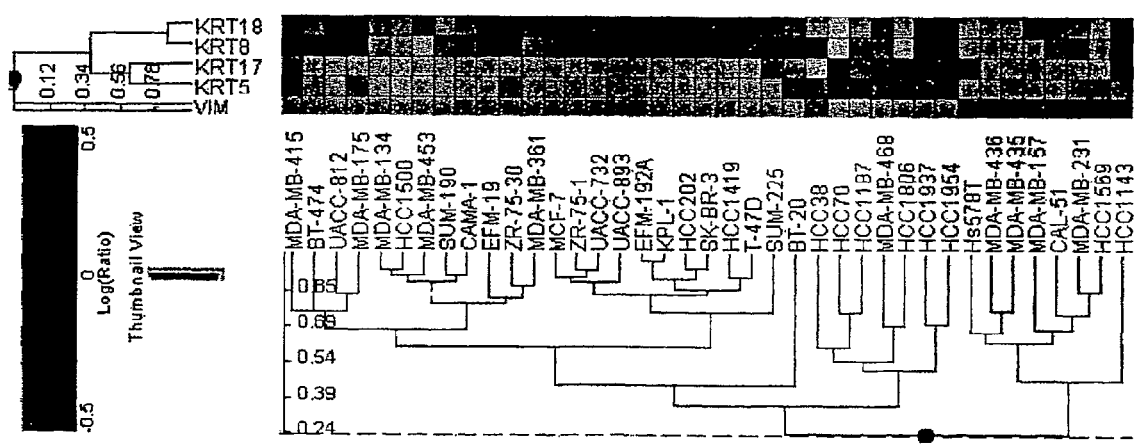
FIG. 1 provides a cluster diagram of relative gene expression of luminal and basal markers including cytokeratins (KRT) 5, 17 and 8, 18, respectively, as well as vimentin (VIM).

The present inventors have discovered certain genes that are differentially expressed in cancerous cells that are sensitive to therapy with N-(2-chloro-6-methylphenyl)-2-[[6-[4-(2-hydroxyethyl)-1-piperazinyl]-2-methyl-4-pyrimidinyl]amino]-5-thiazolecarboxamide. The present invention thus provides, inter alia, methods of using the expression products of the genes to identify cancerous cells that will respond to therapy with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof as well as methods of identifying subjects having cancer that will be positive responders to therapy with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof. The inventors have found, in particular that elevated levels of the expression products of the genes are indicative of sensitivity to therapy with N-(2-chloro-6-methylphenyl)-2-[[6-[4-(2-hydroxyethyl)-1-piperazinyl]-2-methyl-4-pyrimidinyl]amino]-5-thiazolecarboxamide.

A biomarker is an organic biomolecule which is differentially present in a sample taken from a subject of one phenotypic status (e.g., having a disease sensitive to dasatinib therapy) as compared with another phenotypic status (e.g., having a disease resistant to dasatinib therapy). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, can provide measures of relative risk that a subject belongs to one phenotypic status or another. Therefore, they are useful as markers for disease (diagnostics), therapeutic effectiveness of a drug (theranostics) and drug toxicity. The polynucleotide and polypeptides described herein can be used as biomarkers for certain cancers described herein. In particular, the present inventors have identified three genes, moesin ("MSN"), caveolin 1 ("CAV1") and yes-associated-protein 1 ("YAP1") that are differentially expressed in cancerous cells that are sensitive to therapy with N-(2-chloro-6-methylphenyl)-2-[[6-[4-(2-hydroxyethyl)-1-piperazinyl]-2-methyl-4-pyrimidinyl]amino]-5-thiazolecarboxamide. In certain embodiments, these three genes are differentially expressed in basal type/"triple negative" breast cancer cell lines.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Ausubel et al., eds., 1995, Current Protocols in Molecular Biology, Wiley and Sons). As appropriate, procedures involving the use of commercially available kits and reagents are generally carried out in accordance with manufacturer defined protocols and/or parameters unless otherwise noted.

It is to be understood that this invention is not limited to particular methods, reagents, compounds, compositions, or biological systems, which can, of course, vary. It is also to be understood that the terminology used herein is for the purpose of describing particular aspects only, and is not intended to be limiting. As used in this specification and the appended claims, the singular forms "a", "an", and "the" include plural referents unless the content clearly dictates otherwise. Thus, for example, reference to "a peptide" includes a combination of two or more peptides, and the like.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "polynucleotide" means a polymeric form of nucleotides of at least about 10 bases or base pairs in length, either ribonucleotides or deoxynucleotides or a modified form of either type of nucleotide, and is meant to include single and double stranded forms of DNA.

As used herein, the terms "polypeptide," "peptide" and "protein" are used interchangeably herein to refer to a polymer of a polymer of at least about 6 amino acids. Throughout the specification, standard three letter or single letter designations for amino acids are used. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A wild-type moesin gene refers to a naturally occurring moesin gene. A wild-type moesin polypeptide refers to a naturally occurring moesin polypeptide, i.e., a moesin polypeptide having the same amino acid sequence as can be found in nature. A wild-type moesin polynucleotide refers to a naturally occurring moesin polynucleotide, i.e., a moesin polynucleotide having the same nucleic acid sequence as can be found in nature. The term specifically encompasses, for example, naturally-occurring truncated forms of moesin, naturally-occurring variant forms (e.g., alternatively spliced forms), and naturally-occurring allelic variants. Moesin is known to be a linking protein of the submembraneous cytoskeleton that plays a key role in the control of cell morphology, adhesion, and motility (Kobayashi et al., Clinical Cancer Research, 10, 572-580, 2004, incorporated herein by reference in its entirety and for all purposes).

A wild-type caveolin-1 gene refers to a naturally occurring caveolin-1 gene. A wild-type caveolin-1 polypeptide refers to a naturally occurring caveolin-1 polypeptide, i.e., a caveolin-1 polypeptide having the same amino acid sequence as can be found in nature. A wild-type caveolin-1 polynucleotide refers to a naturally occurring caveolin-1 polynucleotide, i.e., a caveolin-1 polynucleotide having the same nucleic acid sequence as can be found in nature. The term specifically encompasses, for example, naturally-occurring truncated forms of caveolin-1, naturally-occurring variant forms (e.g., alternatively spliced forms), and naturally-occurring allelic variants. Caveolin-1 is known to be an essential structural constituent of caveolae that has been implicated in miogenic signaling (Fiucci et al., Oncogene, 2002, 4; 21(15) 2365-2375, incorporated herein by reference in its entirety and for all purposes).

A wild-type yes-associated protein 1 gene refers to a naturally occurring yes-associated protein 1 gene. A wild-type yes-associated protein 1 polypeptide refers to a naturally occurring yes-associated protein 1 polypeptide, i.e., a yes-associated protein 1 polypeptide having the same amino acid sequence as can be found in nature. A wild-type yes-associated protein 1 polynucleotide refers to a naturally occurring yes-associated protein 1 polynucleotide, i.e., a yes-associated protein 1 polynucleotide having the same nucleic acid sequence as can be found in nature. The term specifically encompasses, for example, naturally-occurring truncated forms of caveolin-1, naturally-occurring variant forms (e.g., alternatively spliced forms), and naturally-occurring allelic variants. Yes-associated protein 1 is known to be praline-rich phosphoprotein that binds to the SH3 domain of the Yes proto-oncogene product (Sudol, Oncogene, 1994, 9(8) 2145-2152, incorporated herein by reference in its entirety and for all purposes)

The phrase "specifically binds to" refers to a binding reaction which is determinative of the presence of a target in the presence of a heterogeneous population of other biologics. Thus, under designated assay conditions, the specified binding region bind preferentially to a particular target and do not bind in a significant amount to other components present in a test sample. Specific binding to a target under such conditions can require a binding moiety that is selected for its specificity for a particular target. A variety of assay formats can be used to select binding regions that are specifically reactive with a particular analyte. Typically a specific or selective reaction will be at least twice background signal or noise and more typically more than 10 times background. For purposes of the present invention, compounds, for example small molecules, can be considered for their ability to specifically bind to mutants described herein.

As used herein "cancer" refers to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. The term cancer includes, but is not limited to, cancers of the female reproductive organs including, but not limited to, ovarian cancer, cervical cancer and uterine cancer; lung cancer; breast cancer; renal cell carcinoma; Hodgkin's lymphoma; Non-Hodgkin's lymphoma; cancers of the genitourinary system including, but not limited to, kidney cancer, prostate cancer, bladder cancer, and urethral cancer; cancers of the head and neck; liver cancer; cancers of the gastrointestinal system including, but not limited to, stomach cancer, esophageal cancer, small bowel cancer or colon cancer; cancers of the biliary tree; pancreatic cancer; cancers of the male reproductive system including, but not limited to, testicular cancer; Gestational trophoblastic disease; cancers of the endocrine system including, but not limited to, thyroid cancer, parathyroid cancer, adrenal gland cancer, carcinoid tumors, insulinomas and PNET tumors; sarcomas, including but not limited to, Ewing's sarcoma, osteosarcoma, liposarcoma, leiomyosarcoma, and rhabdomyosarcoma; mesotheliomas; cancers of the skin; melanomas; cancers of the central nervous system; pediatric cancers; and cancers of the hematopoietic system including, but not limited to all forms of leukemia, myelodysplastic syndromes, myeloproliferative disorders and multiple myeloma. A triple negative cancer is one that has reduced expression or no expression of the estrogen receptor, progesterone receptor, and HER2.

As used herein, the terms "hybridize", "hybridizing", "hybridizes" and the like, used in the context of polynucleotides, are meant to refer to conventional hybridization conditions, preferably such as hybridization in 50% formamide/6×SSC/0.1% SDS/100 µg/ml ssDNA, in which temperatures for hybridization are above 37° C. and temperatures for washing in 0.1×SSC/0.1% SDS are above 55° C., and most preferably to stringent hybridization conditions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent condition" or "high stringency conditions" as defined herein, can be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as form amide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

"Moderately stringent conditions" can be identified as described by Sambrook et al., 1989, Molecular Cloning: A Laboratory Manual, New York: Cold Spring Harbor Press, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

As used herein "substantial identity" to a specified sequence refers to 80% identity or greater, i.e., 81%, 82%, 83%, 84%, 85%, 86%, 87%, 88%, 89%, 90%, 91%, 91%, 93%, 94%, 95%, 96%, 97%, 98%, 99%, 99.5% or 99.9% identity to the specified sequence.

In the context of amino acid sequence comparisons, the term "identity" is used to express the percentage of amino acid residues at the same relative positions that are the same. Also in this context, the term "homology" is used to express the percentage of amino acid residues at the same relative positions that are either identical or are similar, using the conserved amino acid criteria of BLAST analysis, as is generally understood in the art. For example, % identity values can be generated by WU-BLAST-2 (Altschul et al., 1996, Methods in Enzymology 266:460-480; blast.wustl/edu/blast/README.html). Further details regarding amino acid substitutions, which are considered conservative under such criteria, are provided below.

The term "cDNAs" refers to complementary DNA that are mRNA molecules present in a cell or organism made into cDNA with an enzyme such as reverse transcriptase. A "cDNA library" is a collection of all of the mRNA molecules present in a cell or organism, all turned into cDNA molecules with the enzyme reverse transcriptase or an equivalent, then inserted into "vectors" (other DNA molecules that can continue to replicate after addition of foreign DNA). Exemplary vectors for libraries include bacteriophage (also known as "phage"), viruses that infect bacteria, for example, lambda phage. The library can then be probed for the specific cDNA (and thus mRNA) of interest.

As used herein, "expression" refers to the process by which polynucleotides are transcribed into mRNA and/or the process by which the transcribed mRNA is subsequently being translated into polypeptides. If the polynucleotide is derived from genomic DNA, expression may include splicing of the mRNA in a eukaryotic cell. "Differentially expressed" as applied to a gene, refers to the differential production of the mRNA transcribed and/or translated from the gene or the protein product encoded by the gene. A differentially expressed gene can be overexpressed or underexpressed as compared to the expression level of a normal or control cell. In one aspect, it refers to a differential that is 1.2, 1.3, 1.4, 1.5 times, 2 times, 2.5 times, 3 times, 4 times, 5 times, or even 10 times higher or lower than the expression level detected in a control sample. The term "differentially expressed" also refers to nucleotide sequences in a cell or tissue which are expressed where silent in a control cell or not expressed where expressed in a control cell. The level of expression of a MCY gene can be determined, for example, by determining the level of MCY polynucleotides and/or polypeptides.

The phrase "determining the level" or "detecting the level" or "evaluating the level" means detecting the presence or absence of an analyte in a sample or quantifying the amount in relative or absolute terms. A relative amount could be, for example, high, medium or low. An absolute amount could reflect the measured strength of a signal or the translation of this signal strength into another quantitative format, such as micrograms/ml.

Additional definitions are provided throughout the subsections that follow.

The following sections describe methods and materials useful in the practice of various embodiments of the invention disclosed herein. The figures and tables provided herein include disclosure that allows the further characterization of the significance of genes such as the gene in the MCY gene set in breast cancer subtypes. The MCY gene set is provided merely as one illustrative example of a set of genes whose expression can be correlated with sensitivity to drugs such as N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof. Those of skill in the art will appreciate that the data provided herein relating to expression of other genes, in particular the expression products and associated disclosure that is provided in Tables 5(a-h), demonstrates that this disclosure is to be used to select other groups of genes whose expression is also correlated with sensitivity to drugs such as N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof. Consequently, one of skill in the art understands that other groups of genes can be identified using this disclosure and examined as is the MCY gene set that is provided as one illustrative example. See also Wilson et al., Breast Cancer Res. 2004; 6(5):192-200 (2004) which is incorporated herein by reference in its entirety and for all purposes.

II. MCY Polynucleotides

One aspect of the invention provides polynucleotides corresponding or complementary to all or part of the moesin, caveolin 1, or yes associated protein 1 (MCY) genes, mRNAs, and/or coding sequences, preferably in isolated form, including polynucleotides encoding MCY protein and fragments thereof, DNA, RNA, DNA/RNA hybrid, and related molecules, polynucleotides or oligonucleotides complementary to the MCY gene or mRNA sequence or a part thereof, and polynucleotides or oligonucleotides that hybridize to MCY gene, mRNA, or to a MCY encoding polynucleotide (collectively, "MCY gene set polynucleotides" or "MCY polynucleotides"). As used herein, the MCY gene set polynucleotide and protein is meant to include the MCY polynucleotides and proteins specifically described herein, moesin, caveolin 1, and yes-associated protein 1, (see, e.g., SEQ ID NO: 1, SEQ ID NO: 2, SEQ ID NO: 3, SEQ ID NO: 4, SEQ ID NO: 5, and SEQ ID NO: 6) and the polynucleotides and proteins corresponding to other MCY polynucleotides and proteins and structurally similar variants of the foregoing. Such other MCY polynucleotides and variants will generally have coding sequences that are highly homologous (i.e., substantially identical) to the MCY gene set coding sequences provided herein, and such other MCY polypeptides and variants will preferably have substantial identity to the MCY polypeptides provided herein, i.e., will share at least about 80% amino acid identity and at least about 90% amino acid homology (using BLAST criteria), more preferably sharing 95% or greater homology (using BLAST criteria).

In certain embodiments, a MCY polynucleotide is MCY polynucleotide having the sequence shown in TABLE 1. A MCY polynucleotide can comprise, for example, a polynucleotide having the nucleotide sequence of human MCY polynucleotide as shown in TABLE 1, wherein T can also be U; a polynucleotide that encodes all or part of the MCY protein; a sequence complementary to the foregoing; or a polynucleotide fragment of any of the foregoing. In certain embodiments, a MCY polynucleotide is a polynucleotide that is capable of hybridizing under stringent hybridization conditions to a human MCY cDNA shown in TABLE 1 or to a polynucleotide fragment thereof.

MCY polynucleotides containing specific portions of the MCY mRNA sequence (and those which are complementary to such sequences) such as those that encode the protein and fragments thereof are provided herein. For example, representative embodiments of the invention disclosed herein include: polynucleotides encoding about amino acid 1 to about amino acid 10 of the MCY proteins shown in TABLE 1, polynucleotides encoding about amino acid 20 to about amino acid 30 of the MCY proteins shown in TABLE 1, polynucleotides encoding about amino acid 30 to about amino acid 40 of the MCY proteins shown in TABLE 1, polynucleotides encoding about amino acid 40 to about amino acid 50 of the MCY t proteins shown in TABLE 1, polynucleotides encoding about amino acid 50 to about amino acid 60 of the MCY proteins shown in TABLE 1, polynucleotides encoding about amino acid 60 to about amino acid 70 of the MCY proteins shown in TABLE 1, polynucleotides encoding about amino acid 70 to about amino acid 80 of the MCY proteins shown in TABLE 1, polynucleotides encoding about amino acid 80 to about amino acid 90 of the MCY proteins shown in TABLE 1 and polynucleotides encoding about amino acid 90 to about amino acid 100 of the MCY proteins shown in TABLE 1, etc. Following this scheme, polynucleotides encoding at least 10 amino acids of the MCY proteins are typical embodiments of the invention. Polynucleotides encoding larger portions of the MCY proteins are also contemplated. For example polynucleotides encoding from about amino acid 1 (or 20 or 30 or 40 etc.) to about amino acid 20, (or 30, or 40 or 50 etc.) of the MCY proteins shown in TABLE 1 can be generated by a variety of techniques well known in the art.

Additional illustrative embodiments of MCY polynucleotides include embodiments consisting of a polynucleotide having the sequence as shown in TABLE 1 from about nucleotide residue number 1 through about nucleotide residue number 500, from about nucleotide residue number 500 through about nucleotide residue number 1000, from about nucleotide residue number 1000 through about nucleotide residue number 1500, from about nucleotide residue number 1500 through about nucleotide residue number 2000, from about nucleotide residue number 2000 through about nucleotide residue number 2500 and from about nucleotide residue number 2500 through about nucleotide residue number 3000 etc. These polynucleotide fragments can include any portion of the MCY sequences as shown in TABLE 1, for example a polynucleotide having at least 10 nucleotides of the sequences as shown in TABLE 1. MCY polynucleotides also include polynucleotides having substantial identity to the sequences shown in Table 1.

Alternatively, as the genes in the MCY gene set are shown to be expressed in a specific subtype of breast cancers, in particular the basal subtype, the polynucleotides disclosed herein can be used in methods assessing the status of MCY gene set to characterize breast cancer subtypes. Typically, polynucleotides encoding specific regions of the MCY protein can be used to assess the levels of MCY mRNA in a cell as well as the presence of perturbations (such as deletions, insertions, point mutations etc.) in specific regions of the MCY gene products. Exemplary assays include both RT-PCR assays as well as single-strand conformation polymorphism (SSCP) analysis (see, e.g., Marrogi et al., 1999, J. Cutan. Pathol. 26(8): 369-378, incorporated herein by reference in its entirety and for all purposes), both of which utilize polynucleotides encoding specific regions of a protein to examine these regions within the protein.

Also provided herein are genomic DNA, cDNAs, ribozymes, and antisense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using, for example, the MCY polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., MCY polynucleotides. See for example, Jack Cohen, 1988, OLIGODEOXYNUCLEOTIDES, Antisense Inhibitors of Gene Expression, CRC Press; and Synthesis 1:1-5 (1988), incorporated herein by reference in its entirety and for all purposes. The MCY polynucleotide antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See Iyer, R. P. et al, 1990, J. Org. Chem. 55:4693-4698; and Iyer, R. P. et al., 1990, J. Am. Chem. Soc. 112: 1253-1254, the disclosures of which are fully incorporated by reference herein. Additional MCY polynucleotide antisense oligonucleotides of the present invention include morpholino antisense oligonucleotides known in the art (see e.g. Partridge et al., 1996, Antisense & Nucleic Acid Drug Development 6: 169-175).

The MCY polynucleotide antisense oligonucleotides of the present invention can be, for example, RNA or DNA that is complementary to and stably hybridizes with the first 100 N-terminal codons or last 100 C-terminal codons of the MCY genomic sequence or the corresponding mRNA. While absolute complementarity is not required, high degrees of complementarity are desirable. Use of an oligonucleotide complementary to this region allows for the selective hybridization to MCY mRNA and not to mRNA specifying other regulatory subunits of protein kinase. Preferably, the MCY polynucleotide antisense oligonucleotides of the present invention are a 15 to 30-mer fragment of the antisense DNA molecule having a sequence that hybridizes to MCY gene set mRNA. Optionally, a MCY polynucleotide antisense oligonucleotide is a 30-mer oligonucleotide that is complementary to a region in the first 10 N-terminal codons and last 10 C-terminal codons of MCY polynucleotides. Alternatively, the antisense molecules can be modified to employ ribozymes in the inhibition of MCY gene expression (L. A. Couture & D. T. Stinchcomb, 1996, Trends Genet. 12: 510-515).

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers can be used to detect the presence of a MCY polynucleotide in a sample and as a means for detecting a cell expressing a MCY protein.

Examples of such probes include polynucleotides comprising all or part of the human MCY cDNA sequences shown in TABLE 1. Examples of primer pairs capable of specifically amplifying MCY mRNAs are easily made by those of skill in the art. As will be understood by the skilled artisan, a great many different primers and probes can be prepared based on the sequences provided herein and used effectively to amplify and/or detect a MCY mRNA.

As used herein, a polynucleotide is said to be "isolated" when it is substantially separated from contaminant polynucleotides that correspond or are complementary to polynucleotides other than the MCY polynucleotides or that encode polypeptides other than MCY polypeptides, including fragments thereof. A skilled artisan can readily employ nucleic acid isolation procedures to obtain an isolated MCY polynucleotide.

The MCY polynucleotides of the invention are useful for a variety of purposes, including but not limited to their use as probes and primers for the amplification and/or detection of the MCY gene(s), mRNA(s), or fragments thereof; as reagents for the diagnosis and/or prognosis of breast cancer (e.g. specific breast cancer subtypes) and other cancers; as coding sequences capable of directing the expression of MCY polypeptides; as tools for modulating or inhibiting the expression of the MCY gene(s) and/or translation of the MCY transcript(s); and as therapeutic agents.

III. Isolation of MCY Nucleic Acid Molecules

The MCY cDNA sequences described herein enable the isolation of other polynucleotides encoding MCY gene product(s), as well as the isolation of polynucleotides encoding MCY gene product homologs, alternatively spliced isoforms, allelic variants, and mutant forms of the MCY gene set gene product. Various molecular cloning methods that can be employed to isolate fill length cDNAs encoding a MCY protein are well known (See, e.g., Sambrook, J. et al., 1989, Molecular Cloning: A Laboratory Manual, 2d ed., Cold Spring Harbor Press, New York; Ausubel et al., eds., 1995, Current Protocols in Molecular Biology, Wiley and Sons). For example, lambda phage cloning methodologies can be conveniently employed, using commercially available cloning systems (e.g., Lambda ZAP Express, Stratagene). Phage clones containing MCY cDNAs can be identified by probing with a labeled MCY cDNA or a fragment thereof. For example, in certain embodiments, the MCY cDNA (TABLE 1) or a portion thereof can be synthesized and used as a probe to retrieve overlapping and full length cDNAs corresponding to a MCY polynucleotide. The MCY members can be isolated, for example, by screening genomic DNA libraries, bacterial artificial chromosome libraries (BACs), yeast artificial chromosome libraries (YACs), and the like, with MCY DNA probes or primers.

IV. Recombinant DNA Molecules and Host-Vector Systems

The invention also provides recombinant DNA or RNA molecules comprising a MCY polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, e.g., Sambrook et al, 1989, supra).

The invention further provides a host-vector system comprising a recombinant DNA molecule containing a MCY polynucleotide within a suitable prokaryotic or eukaryotic host cell. Examples of suitable eukaryotic host cells include, for example, a yeast cell, a plant cell, or an animal cell, such as a mammalian cell or an insect cell (e.g., a baculovirus-infectible cell such as an Sf9 or HighFive cell). Examples of suitable mammalian cells include, for example, various breast cancer cell lines such as MDA 231, MCF-7, other transfectable or transducible breast cancer cell lines, as well as a number of mammalian cells routinely used for the expression of recombinant proteins (e.g., COS, CHO, MCF-7 cells). More particularly, a polynucleotide comprising the coding sequence of a MCY gene can be used to generate MCY proteins or fragments thereof using any number of host-vector systems routinely used and widely known in the art.

A wide range of host-vector systems suitable for the expression of a MCY proteins or fragments thereof are available (see, e.g., Sambrook et al., 1989, supra; Current Protocols in Molecular Biology, 1995, supra). Common vectors for mammalian expression include but are not limited to pcDNA 3.1 myc-His-tag (Invitrogen) and the retroviral vector pSRαt-kneo (Muller et al., 1991, MCB 11:1785). Using these expression vectors, MCY gene set may be preferably expressed in several breast cancer and non-breast cell lines, including for example, MCF-7, rat-1, NIH 3T3 and TsuPr1. The host-vector systems of the invention are useful for the production of a MCY protein or fragment thereof. Such host-vector systems can be employed to study the functional properties of MCY gene set and MCY gene set mutations.

Recombinant human MCY protein can be produced by mammalian cells transfected with a construct encoding MCY gene set. In an illustrative embodiment, MCF-7 cells can be transfected with an expression plasmid encoding MCY protein, the MCY protein is expressed in the MCF-7 cells, and the recombinant MCY protein can be isolated using standard purification methods (e.g., affinity purification using anti-MCY gene set antibodies). In another embodiment, the MCY coding sequence is subcloned into the retroviral vector pSRαMSVtkneo and used to infect various mammalian cell lines, such as NIH 3T3, MCF-7 and rat-1 in order to establish MCY gene set expressing cell lines. Various other expression systems well known in the art can also be employed. Expression-constructs encoding a leader peptide joined in frame to the MCY coding sequence can be used for the generation of a secreted form of recombinant MCY protein.

Proteins encoded by the MCY genes, or by fragments thereof, have a variety of uses, including, for example, generating antibodies and in methods for identifying ligands and other agents and cellular constituents that bind to a MCY gene set gene product. Antibodies raised against a MCY protein or fragment thereof are in diagnostic and prognostic assays, and imaging methodologies in the management of human cancers characterized by expression of MCY g protein, including, for example, cancers of the breast. Such antibodies can be expressed intracellularly and used in methods of treating patients with such cancers. Various immunological assays useful for the detection of MCY proteins are contemplated, including but not limited to various types of radioimmunoassays, enzyme-linked immunosorbent assays (ELISA), enzyme-linked immunofluorescent assays (ELIFA), immunocytochemical methods, and the like. Such antibodies can be labeled and used as immunological imaging reagents capable of detecting MCY gene set expressing cells (e.g., in radioscintigraphic imaging methods). MCY proteins are also particularly useful in generating cancer vaccines, as further described below.

V. MCY Polypeptides

MCY proteins and polypeptide fragments thereof are provided herein. MCY proteins of the invention include those specifically identified herein, as well as allelic variants, conservative substitution variants and homologs that can be isolated/generated and characterized without undue experimentation following methods known in the art and methods outlined below. Fusion proteins that combine parts of different MCY proteins or fragments thereof, as well as fusion proteins of a MCY protein and a heterologous polypeptide are also included in the present invention. Such MCY proteins will be collectively referred to as the MCY proteins MCY polypeptides, the proteins of the invention, or MCY gene set proteins.

Specific embodiments of MCY proteins comprise a polypeptide having the amino acid sequence of human MCY polypeptides as shown in TABLE 1. Alternatively, embodiments of MCY proteins comprise variant polypeptides having alterations in the amino acid sequence of human MCY polypeptides as shown in TABLE 1, including polypeptides having sequences with substantial identity to those provided in TABLE 1.

In general, naturally occurring allelic variants of human MCY proteins will share a high degree of structural identity and homology (e.g., 90% or more identity). Typically, allelic variants of the MCY proteins will contain conservative amino acid substitutions within the MCY sequences described herein or will contain a substitution of an amino acid from a corresponding position in a MCY homologue. One class of MCY protein allelic variants will be proteins that share a high degree of homology with at least a small region of a particular MCY amino acid sequence, but will further contain a radical departure from the sequence, such as a non-conservative substitution, truncation, insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Embodiments of the invention disclosed herein include a wide variety of art accepted variants of MCY proteins such as polypeptides having amino acid insertions, deletions and substitutions. MCY protein variants can be made using methods known in the art such as site-directed mutagenesis, alanine scanning, and PCR mutagenesis. Site-directed mutagenesis (Carter et al., 1986, Nucl. Acids Res. 13:4331; Zoller et al., 1987, Nucl. Acids Res. 10:6487), cassette mutagenesis (Wells et al., 1985, Gene 34:315), restriction selection mutagenesis (Wells et al., 1986, Philos. Trans. R. Soc. London Ser. A, 317:415) or other known techniques can be performed on the cloned DNA to produce the MCY gene set variant DNA. Scanning amino acid analysis can also be employed to identify one or more amino acids along a contiguous sequence. Among the common scanning amino acids are relatively small, neutral amino acids. Such amino acids include alanine, glycine, serine, and cysteine. Alanine is typically a common scanning amino acid among this group because it climinates the side-chain beyond the beta-carbon and is less likely to alter the main-chain conformation of the variant. Alanine is also typically used because it is the most common amino acid. Further, it is frequently found in both buried and exposed positions (Creighton, The Proteins, (W.H. Freeman & Co., N.Y.); Chothia, 1976, J. Mol. Biol., 150:1). If alanine substitution does not yield adequate amounts of variant, an isosteric amino acid can be used.

Embodiments of the claimed invention include polypeptides containing less than the complete amino acid sequence of the MCY protein shown in TABLE 1 (and the polynucleotides encoding such polypeptides). For example, representative embodiments of the invention disclosed herein include polypeptides consisting of about amino acid 1 to about amino acid 10 of the MCY protein shown in TABLE 1, polypeptides consisting of about amino acid 20 to about amino acid 30 of the MCY protein shown in TABLE 1, polypeptides consisting of about amino acid 30 to about amino acid 40 of the MCY protein shown in TABLE 1, polypeptides consisting of about amino acid 40 to about amino acid 50 of the MCY t protein shown in TABLE 1, polypeptides consisting of about amino acid 50 to about amino acid 60 of the MCY protein shown in TABLE 1, polypeptides consisting of about amino acid 60 to about amino acid 70 of the MCY protein shown in TABLE 1, polypeptides consisting of about amino acid 70 to about amino acid 80 of the MCY protein shown in TABLE 1, polypeptides consisting of about amino acid 80 to about amino acid 90 of the MCY protein shown in TABLE 1 and polypeptides consisting of about amino acid 90 to about amino acid 100 of the MCY protein shown in TABLE 1, etc. Polypeptides consisting of larger portions of the MCY protein are also contemplated. For example polypeptides consisting of about amino acid 1 (or 20 or 30 or 40 etc.) to about amino acid 20, (or 30, or 40 or 50 etc.) of the MCY protein shown in TABLE 1 can be generated by a variety of techniques well known in the art.

The polypeptides of the preceding paragraphs have a number of different specific uses. These polypeptides can be used in methods of assessing the status of MCY gene products in normal versus cancerous tissues and elucidating the malignant phenotype. Typically, polynucleotides encoding specific regions of the MCY protein can be used to assess the presence of perturbations (such as deletions, insertions, point mutations etc.) in specific regions of the MCY gene products. Exemplary assays can utilize antibodies targeting a MCY polypeptide containing the amino acid residues of one or more of the biological motifs contained within the MCY polypeptide sequence in order to evaluate the characteristics of this region in normal versus cancerous tissues. Alternatively, MCY polypeptides containing the amino acid residues of one or more of the biological motifs contained within the MCY polypeptide sequence can be used to screen for factors that interact with that region of MCY polypeptides.

Redundancy in the genetic code permits variation in MCY sequences. In particular, one skilled in the art will recognize specific codon preferences by a specific host species and can adapt the disclosed sequence as preferred for a desired host. For example, certain codon sequences typically have rare codons (i.e., codons having a usage frequency of less than about 20% in known sequences of the desired host) replaced with higher frequency codons. Codon preferences for a specific organism can be calculated, for example, by utilizing codon usage tables available on the Internet at the following address: www.dna.affrc.go.jp/~nakamura/codon.html. Nucleotide sequences that have been optimized for a particular host species by replacing any codons having a usage frequency of less than about 20% are referred to herein as "codon optimized sequences."

Additional sequence modifications are known to enhance protein expression in a cellular host. These include elimination of sequences encoding spurious polyadenylation signals, exon/intron splice site signals, transposon-like repeats, and/or other such well-characterized sequences that may be deleterious to gene expression. The GC content of the sequence can be adjusted to levels average for a given cellular host, as calculated by reference to known genes expressed in the host cell. Where possible, the sequence can also be modified to avoid predicted hairpin secondary mRNA structures. Other useful modifications include the addition of a translational initiation consensus sequence at the start of the open reading frame, as described in Kozak, 1989, Mol. Cell. Biol., 9:5073-5080. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequence."

MCY proteins can be embodied in many forms, preferably in isolated form. As used herein, a protein is said to be "isolated" when physical, mechanical or chemical methods are employed to remove the MCY protein from cellular constituents that are normally associated with the protein. A skilled artisan can readily employ standard purification methods to obtain an isolated MCY protein. A purified MCY protein molecule will be substantially free of other proteins or molecules that impair the binding of MCY protein to antibody or other ligand. The nature and degree of isolation and purification will depend on the intended use. Embodiments of a MCY protein include, for example, a purified MCY protein and a functional, soluble MCY protein. In one form, such functional, soluble MCY proteins or fragments thereof retain the ability to bind antibody or other ligand.

The invention also provides MCY polypeptides comprising biologically active fragments of the MCY amino acid sequence, such as a polypeptide corresponding to part of the amino acid sequence for MCY as shown in TABLE 1. Such polypeptides of the invention exhibit properties of the MCY protein, such as the ability to elicit the generation of antibodies that specifically bind an epitope associated with the MCY protein.

MCY polypeptides can be generated using standard peptide synthesis technology or using chemical cleavage methods well known in the art based on the amino acid sequences of the human MCY proteins disclosed herein. Alternatively, recombinant methods can be used to generate nucleic acid molecules that encode a polypeptide fragment of a MCY protein. In this regard, the MCY protein-encoding nucleic acid molecules described herein provide means for generating defined fragments of MCY proteins. MCY polypeptides are particularly useful in generating and characterizing domain specific antibodies (e.g., antibodies recognizing an extracellular or intracellular epitope of a MCY gene set protein), in identifying agents or cellular factors that bind to MCY proteins or a particular structural domain thereof, and in various therapeutic contexts, including but not limited to cancer vaccines.

MCY polypeptides containing particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments containing such structures are particularly useful in generating subunit specific anti-MCY antibodies or in identifying cellular factors that bind to MCY polypeptide.

In certain embodiments, the MCY polypeptides can be conveniently expressed in cells (such as MCF-7 cells) transfected with a commercially available expression vector such as a CMV-driven expression vector encoding MCY protein with a C-terminal 6×His and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted MCY gene set protein in transfected cells. The secreted HIS-tagged MCY protein in the culture media can be purified using a nickel column using standard techniques.

The MCY polypeptides of the present invention can also be modified in a way to form a chimeric molecule comprising MCY polypeptides fused to another, heterologous polypeptide or amino acid sequence. In one embodiment, such a chimeric molecule comprises a fusion of a MCY polypeptide with a polyhistidine epitope tag, which provides an epitope to which immobilized nickel can selectively bind. The epitope tag is generally placed at the amino- or carboxyl-terminus of the MCY gene set. In an alternative embodiment, the chimeric molecule can comprise a fusion of a MCY polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a MCY polypeptide in place of at least one variable region within an Ig molecule. In particular embodiments, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

VI. MCY Antibodies

The term "antibody" is used in the broadest sense and specifically covers single anti-MCY protein monoclonal antibodies (including agonist, antagonist and neutralizing antibodies) and anti-MCY protein antibody compositions with polyepitopic specificity. It also includes, for example, polyclonal antibodies, bispecific antibodies, diabodies, chimeric, single-chain, and humanized antibodies, as well as antibody fragments (e.g., Fab, $F(ab')_2$, and Fv), so long as they exhibit the desired biological activity.

The term "monoclonal antibody" (mAb) as used herein refers to an antibody obtained from a population of substantially homogeneous antibodies, i.e. the antibodies comprising the individual population are identical except for possible naturally-occurring mutations that may be present in minor amounts.

Another aspect of the invention provides antibodies that bind to MCY polypeptides. The most common antibodies will specifically bind to a MCY protein and will not bind (or will bind weakly) to non-MCY proteins. Anti-MCY antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule that binds to its target, i.e., the antigen binding region.

MCY antibodies of the invention are particularly useful in breast cancer diagnostic and prognostic assays, and imaging methodologies. Intracellularly expressed antibodies (e.g., single chain antibodies) can be therapeutically useful in treating cancers in which the expression of MCY gene set is involved, such as for example advanced and metastatic breast cancers. Such antibodies can be useful in the treatment, diagnosis, and/or prognosis of other cancers, to the extent MCY gene set is also expressed or overexpressed in other types of cancers such as breast cancers.

The invention also provides various immunological assays useful for the detection and quantification of MCY proteins and polypeptides including mutant MCY proteins and polypeptides. Such assays can comprise one or more MCY gone set antibodies capable of recognizing and binding a MCY protein including a mutant MCY protein, as appropriate, and can be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting breast cancer and other cancers expressing MCY proteins are also provided by the invention, including but limited to radioscintigraphic imaging methods using labeled MCY gene set antibodies. Such assays can be clinically useful in the detection, monitoring, and prognosis of MCY gene set expressing cancers such as breast cancer.

MCY antibodies can also be used in methods for purifying MCY proteins including mutant MCY proteins s and for isolating MCY homologues and related molecules. For example, in certain embodiments, the method of purifying a MCY protein comprises incubating a MCY antibody, which has been coupled to a solid matrix, with a lysate or other solution containing MCY gene set under conditions that permit the MCY antibody to bind to MCY protein; washing the solid matrix to eliminate impurities; and eluting the MCY protein from the coupled antibody. Other uses of the MCY antibodies of the invention include generating anti-idiotypic antibodies that mimic the MCY protein.

Various methods for the preparation of antibodies are well known in the art. For example, antibodies can be prepared by immunizing a suitable mammalian host using a MCY protein, peptide, or fragment, in isolated or immunoconjugated form (Harlow, and Lane, eds., 1988, Antibodies: A Laboratory Manual, CSH Press; Harlow, 1989, Antibodies, Cold Spring Harbor Press, NY). In addition, fusion proteins of MCY can also be used, such as a MCY GST-fusion protein. In a particular embodiment, a GST fusion protein comprising all or most of the open reading frame amino acid sequence of TABLE 1 can be produced and used as an immunogen to generate appropriate antibodies. In another embodiment, a MCY peptide can be synthesized and used as an immunogen.

In addition, naked DNA immunization techniques known in the art can be used (with or without purified MCY protein or MCY expressing cells) to generate an immune response to the encoded immunogen (for review, see Donnelly et al., 1997, Ann. Rev. Immunol. 15:617-648).

The amino acid sequence of the MCY protein as shown in TABLE 1 can be used to select specific regions of the MCY protein for generating antibodies. For example, hydrophobicity and hydrophilicity analyses of the MCY amino acid sequence can be used to identify hydrophilic regions in the MCY gene set structure. Regions of the MCY protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents can be used; in other instances linking reagents such as those supplied by Pierce Chemical Co., Rockford, Ill., can be effective. Administration of a MCY gene set immunogen can be conducted by injection over a suitable time period and with use of a suitable adjuvant, as is generally understood in the art. During the immunization schedule, titers of antibodies can be taken to determine adequacy of antibody formation.

MCY monoclonal antibodies can be produced by various means well known in the art. For example, immortalized cell lines that secrete a desired monoclonal antibody can be prepared using the standard hybridoma technology of Kohler and Milstein or modifications that immortalize producing B cells, as is generally known. The immortalized cell lines secreting the desired antibodies are screened by immunoassay in which the antigen is the MCY protein or a MCY fragment. When the appropriate immortalized cell culture secreting the desired antibody is identified, the cells can be expanded and antibodies produced either from in vitro cultures or from ascites fluid.

The antibodies or fragments can also be produced, using current technology, by recombinant means. Regions that bind specifically to the desired regions of the MCY protein can also be produced in the context of chimeric or CDR grafted antibodies of multiple species origin. Humanized or human MCY antibodies can also be produced for use in therapeutic contexts. Methods for humanizing murine and other non-human antibodies by substituting one or more of the non-human antibody CDRs for corresponding human antibody sequences are well known (see for example, Jones et al., 1986, Nature 321:522-525; Riechmann et al., 1988, Nature 332:323-327; Verhoeyen et al., 1988, Science 239:1534-1536). See also, Carter et al., 1993, Proc. Natl. Acad. Sci. USA 89:4285 and Sims et al., 1993, J. Immunol. 151:2296. Methods for producing fully human monoclonal antibodies include phage display and transgenic methods (for review, see Vaughan et al., 1998, Nature Biotechnology 16:535-539).

Fully human MCY gene set monoclonal antibodies can be generated using cloning technologies employing large human Ig gene combinatorial libraries (i.e., phage display) (Griffiths and, Hoogenboom, Building an in vitro immune system: human antibodies from phage display libraries. In: Clark, M., ed., 1993, Protein Engineering of Antibody Molecules for Prophylactic and Therapeutic Applications in Man, Nottingham Academic, pp 45-64; Burton and Barbas, Human Antibodies from combinatorial libraries. Id., pp. 65-82). Fully human MCY monoclonal antibodies can also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4):607-614). This method avoids the in vitro manipulation required with phage display technology and efficiently produces high affinity authentic human antibodies.

Reactivity of MCY antibodies with a MCY protein can be established by a number of well known means, including western blot, immunoprecipitation, ELISA, and FACS analyses using, as appropriate, MCY proteins, peptides, MCY-expressing cells or extracts thereof.

A MCY antibody or fragment thereof of the invention can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. A second molecule for conjugation to the MCY gene set antibody can be selected in accordance with the intended use. For example, for therapeutic use, the second molecule can be a toxin or therapeutic agent. Further, bi-specific antibodies specific for two or more MCY epitopes can be generated using methods generally known in the art. Homodimeric antibodies may also be generated by cross-linking techniques known in the art (e.g., Wolff et al., 1993, Cancer Res. 53: 2560-2565).

VII. Transgenic Animals

Nucleic acids that encode a MCY polypeptide or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In certain embodiments, cDNA encoding MCY polypeptides can be used to clone genomic DNA encoding MCY polypeptides in accordance with established techniques and the genomic sequences used to generate transgenic animals that contain cells that express DNA encoding MCY polypeptides. Methods for generating transgenic animals, particularly animals such as mice or rats, have become conventional in the art and are described, for example, in U.S. Pat. Nos. 4,736,866 and 4,870,009, incorporated herein by reference in their entirety and for all purposes. Typically, particular cells would be targeted for MCY transgene incorporation with tissue-specific enhancers. Transgenic animals that include a copy of a transgene encoding MCY polypeptides introduced into the germ line of the animal at an embryonic stage can be used to examine the effect of increased expression of DNA encoding MCY polypeptides. Such animals can be used as tester animals for reagents thought to confer protection from, for example, pathological conditions associated with its overexpression. In accordance with certain embodiments of the invention, an animal is treated with the reagent and a reduced incidence of the pathological condition, compared to untreated animals bearing the transgene, would indicate a potential therapeutic intervention for the pathological condition.

Alternatively, non-human homologues of MCY polynucleotides can be used to construct a MCY gene set "knock out" animal that has a defective or altered gene as a result of homologous recombination between the endogenous gene and altered genomic DNA introduced into an embryonic cell of the animal. For example, cDNA can be used to clone genomic DNA in accordance with established techniques. A portion of the genomic DNA e can be deleted or replaced with another gene, such as a gene encoding a selectable marker that can be used to monitor integration. Typically, several kilobases of unaltered flanking DNA (both at the 5' and 3' ends) are included in the vector (see e.g., Thomas and Capecchi, 1987, Cell 51:503) for a description of homologous recombination vectors]. The vector is introduced into an embryonic stem cell line (e.g., by electroporation) and cells in which the introduced DNA has homologously recombined with the endogenous DNA are selected (see e.g., Li et al., 1992, Cell 69:915). The selected cells are then injected into a blastocyst of an animal (e.g., a mouse or rat) to form aggregation chimeras (see e.g., Bradley, in Robertson, ed., 1987, Teratocarcinomas and Embryonic Stem Cells: A Practical Approach, (IRL, Oxford), pp. 113-152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the MCY polypeptide.

VIII. Methods for the Detection of MCY Polynucleotides or Polypeptides

Another aspect of the present invention relates to methods for detecting MCY polynucleotides and MCY proteins including variants thereof, as well as methods for identifying a cell that expresses MCY polynucleotides and polypeptides. The expression profile of a MCY gene set makes it a diagnostic marker for breast cancer and breast cancer subtype. In this context, the status of MCY polynucleotides and proteins provides information useful for predicting a variety of factors including susceptibility to advanced stage disease, rate of progression, and/or tumor aggressiveness. As discussed in detail below, the status of MCY polynucleotides and proteins in patient samples can be analyzed by a variety protocols that are well known in the art including immunohistochemical analysis, the variety of Northern blotting techniques including in situ hybridization, RT-PCR analysis (for example on laser capture micro-dissected samples), western blot analysis and tissue array analysis.

More particularly, the invention provides assays for the detection of MCY polynucleotides in a biological sample, such as a breast biopsy and the like. Detectable MCY polynucleotides include, for example, a MCY gene or fragments thereof, MCY mRNA, alternative splice variant MCY mRNAs, and recombinant DNA or RNA molecules containing a MCY polynucleotide. A number of methods for amplifying and/or detecting the presence of MCY polynucleotides are well known in the art and can be employed in the practice of this aspect of the invention.

In certain aspects, methods for detecting MCY mRNA in a biological sample comprises producing cDNA from the sample by reverse transcription. In certain embodiments, the cDNA is amplified using MCY polynucleotides as sense and antisense primers to amplify MCY cDNAs therein and the presence of the amplified MCY cDNA is detected. In certain embodiments, the sequence of the amplified MCY cDNA is determined. In certain other embodiments, methods of detecting a MCY gene in a biological sample comprises first isolating genomic DNA from the sample; amplifying the isolated genomic DNA using MCY polynucleotides as sense and antisense primers to amplify the MCY gene therein; and detecting the presence of the amplified MCY gene. Any number of appropriate sense and antisense probe combinations can be designed from the nucleotide sequences provided for the MCY polynucleotides (TABLE 1) and used for this purpose.

The invention also provides assays for detecting the presence of a MCY protein in a tissue of other biological sample such as breast cell preparations, and the like. Methods for detecting a MCY protein are also well known and include, for example, immunoprecipitation, immunohistochemical analysis, Western Blot analysis, molecular binding assays, ELISA, ELIFA and the like. For example, in certain embodiments, methods of detecting the presence of a MCY protein in a biological sample comprises first contacting the sample with a MCY antibody, a MCY-reactive fragment thereof, or a recombinant protein containing an antigen binding region of a MCY antibody; and then detecting the binding of MCY protein in the sample thereto.

In some embodiments of the invention, the expression of MCY proteins in a sample is examined using immunohistochemical staining protocols. Immunohistochemical staining of tissue sections has been shown to be a reliable method of assessing alteration of proteins in a heterogeneous tissue.

Immunohistochemistry (IHC) techniques utilize an antibody to probe and visualize cellular antigens in situ, generally by chromogenic or fluorescent methods. This technique excels because it avoids the unwanted effects of disaggregation and allows for evaluation of individual cells in the context of morphology. In addition, the target protein is not altered by the freezing process.

Certain protocols that examine the expression of MCY proteins in a sample typically involve the preparation of a tissue sample followed by immunohistochemistry. Illustrative protocols are provided below. For sample preparation, any tissue sample from a subject can be used. Examples of tissue samples that can be used include, for example, breast tissue. The tissue sample can be obtained by a variety of procedures including, for example, to surgical excision, aspiration or biopsy. The tissue can be fresh or frozen. In one embodiment, the tissue sample is fixed and embedded in paraffin or the like. The tissue sample can be fixed (i.e. preserved) by conventional methodology (See e.g., "Manual of Histological Staining Method of the Armed Forces Institute of Pathology," 3$^{rd}$ edition (1960) Lee G. Luna, HT (ASCP) Editor, The Blakston Division McGraw-Hill Book Company, New York; *The Armed Forces Institute of Pathology Advanced Laboratory Methods in Histology and Pathology* (1994) Ulreka V. Mikel, Editor, Armed Forces Institute of Pathology, American Registry of Pathology, Washington, D.C.). One of skill in the art will appreciate that the choice of a fixative is determined by the purpose for which the tissue is to be histologically stained or otherwise analyzed. One of skill in the art will also appreciate that the length of fixation depends upon the size of the tissue sample and the fixative used. By way of example, neutral buffered formalin, Bouin's or paraformaldehyde, can be used to fix a tissue sample.

Generally, the tissue sample is first fixed and is then dehydrated through an ascending series of alcohols, infiltrated and embedded with paraffin or other sectioning media so that the tissue sample can be sectioned. Alternatively, one can section the tissue and fix the sections obtained. By way of example, the tissue sample can be embedded and processed in paraffin by conventional methodology (See e.g., "Manual of Histological Staining Method of the Armed Forces Institute of Pathology", supra). Examples of paraffin that can be used include, but are not limited to, Paraplast, Broloid, and Tissuemay. Once the tissue sample is embedded, the sample can be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections can be attached to slides by several standard methods. Examples of slide adhesives include, but are not limited to, silane, gelatin, poly-L-lysine and the like. By way of example, the paraffin embedded sections can be attached to positively charged slides and/or slides coated with poly-L-lysine.

If paraffin has been used as the embedding material, the tissue sections are generally deparaffinized and rehydrated to water. The tissue sections can be deparaffinized by several conventional standard methodologies. For example, xylenes and a gradually descending series of alcohols can be used (See e.g., "Manual of Histological Staining Method of the Armed Forces Institute of Pathology", supra). Alternatively, commercially available deparaffinizing non-organic agents such as Hemo-De7 (CMS, Houston, Tex.) can be used.

Subsequent to tissue preparation, a tissue section can be subjected to immunohistochemistry (IHC). IHC can be performed in combination with additional techniques such as morphological staining and/or fluorescence in-situ hybridization. Two general methods of IHC are available; direct and indirect assays. According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate can be added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:

(a) Radioisotopes, such as $^{35}$S, $^{14}$C, $^{125}$I, $^{3}$H, and $^{131}$I. The antibody can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting.

(b) Colloidal gold particles.

(c) Fluorescent labels including, for example, rare earth chelates (europium chelates), Texas Red, rhodamine, fluorescein, dansyl, Lissamine, umbelliferone, phycocrytherin, phycocyanin, or commercially available fluorophores such SPECTRUM ORANGE7 and SPECTRUM GREEN7 and/or derivatives of any one or more of the above. The fluorescent labels can be conjugated to the antibody using the techniques disclosed in *Current Protocols in Immunology*, supra, for example. Fluorescence can be quantified using a fluorimeter.

(d) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme can catalyze a color change in a substrate, which can be measured spectrophotometrically. Alternatively, the enzyme can alter the fluorescence or chemiluminescence of the substrate. Techniques for quantifying a change in fluorescence are described above. The chemiluminescent substrate becomes electronically excited by a chemical reaction and can then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al, Methods for the Preparation of Enzyme-Antibody Conjugates for use in Enzyme Immunoassay, in *Methods in Enzym.* (ed. J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase).

Numerous other enzyme-substrate combinations are available to those skilled in the art. For a general review of these, see U.S. Pat. Nos. 4,275,149 and 4,318,980, incorporated herein by reference in their entirety and for all purposes. Sometimes, the label is indirectly conjugated with the antibody. The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten and one of the different types of labels mentioned above is conjugated with an anti-hapten antibody. Thus, indirect conjugation of the label with the antibody can be achieved.

Aside from the sample preparation procedures discussed above, further treatment of the tissue section prior to, during or following IHC may be desired, For example, epitope retrieval methods, such as heating the tissue sample in citrate buffer may be carried out (see, e.g., Leong et al. *Appl. Immunohistochem.* 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. Preferably, the label is an enzymatic label (e.g. HRPO) which catalyzes a chemical alteration of the chromogenic substrate such as 3,3'-diaminobenzidine chromogen. Preferably the enzymatic label is conjugated to antibody which binds specifically to the primary antibody (e.g. the primary antibody is rabbit polygonal antibody and secondary antibody is goat anti-rabbit antibody).

Specimens thus prepared may be mounted and coverslipped. Slide evaluation is then determined, e.g. using a microscope.

While not being bound by the following parameters. protein staining intensity criteria can be evaluated as illustrated by the following chart:

IX. Protein Staining Intensity Criteria

| Staining Pattern | Score |
| --- | --- |
| No staining is observed in tumor cells. | 0 |
| A faint/barely perceptible staining is detected in tumor cells. | 1+ |
| A weak to moderate complete staining is observed in tumor cells. | 2+ |
| A moderate to strong complete staining is observed in tumor cells. | 3+ |
| A strong to very strong complete staining is observed in tumor cells. | 4+ |

In certain embodiments, the level of expression of the MCY polypeptides is measured by an immunoassay. Those skilled in the art are aware that, an "immunoassay" typically comprises incubating a test sample with one or more immunointeractive molecules specific for a target for a time and under conditions sufficient for binding thereto and detecting said binding. As used herein, the term "target" refers to the analyte which a probe is designed to bind. In certain embodiments, the immunointeractive molecule will be an antibody. Conditions for incubating an antibody with a test sample vary, depending upon the format employed in the assay, the detection methods employed and the type and nature of the antibody molecule used in the assay. Those skilled in the art will recognize that any one of the commonly available immunological assay formats, for example radioimmunoassays, enzyme-linked immunosorbent assays (ELISA), diffusion-based Ouchterlony, rocket gel immunoelectrophoresis or in situ immunoassays can be readily adapted to the present purpose.

Immunoassays are useful in the quantification of a polypeptide in a test sample, in particular to determine whether the level of a MCY polypeptide is altered compared to normal levels detectable in non-diseased individuals or individuals having a different type of disease or even different type of breast cancer. The immunoassay can have other uses as well, such as, for example, use in the monitoring of disease progression or monitoring of response to therapeutic interventions. The invention described herein extends to all such uses of immunointeractive molecules and diagnostic assays which require said immunoassays for their performance.

By way of example only, in certain embodiments, an antibody raised against a MCY polypeptide is immobilised onto a solid substrate to form a first complex and a biological test sample from a patient is brought into contact with the bound molecule. After a suitable period of incubation, for a period of time sufficient to allow formation of an antibody-secondary complex, a second antibody labeled with a reporter molecule capable of producing a detectable signal is then added and incubated, allowing sufficient time for the formation of a tertiary complex. Any unreacted material is washed away, and the presence of the tertiary complex is determined by observation of a signal produced by the reporter molecule. The results can either be qualitative, by simple observation of the visible signal or can be quantitated by comparison with a control sample containing known amounts of hapten. Variations of this assay include a simultaneous assay, in which both sample and labeled antibody are added simultaneously to the bound antibody, or a reverse assay in which the labeled antibody and sample to be tested are first combined, incubated and then added simultaneously to the bound antibody. These techniques are well known to those skilled in the art, and the possibility of variations will be readily apparent.

By "reporter molecule", as used in the present specification, is meant a molecule which, by its chemical nature, produces an analytically identifiable signal which allows the detection of antigen-bound antibody. Detection can be either qualitative or quantitative. The most commonly used reporter molecule in this type of assay are either enzymes, fluorophores or radionuclide containing molecules (i.e. radioisotopes)

The solid substrate is typically glass or a polymer, the most commonly used polymers being cellulose, polyacrylamide, nylon, polystyrene, polyvinyl chloride or polypropylene. The solid supports can be in the form of tubes, beads, discs or microplates, or any other surface suitable for conducting an immunoassay. The binding processes are well-known in the art and generally consist of cross-linking covalently binding or physically adsorbing the molecule to the insoluble carrier.

A variety of immunoassay formats, including, for example, competitive and non-competitive immunoassay formats, antigen capture assays and two-antibody sandwich assays can be used in the methods of the invention (Self and Cook, *Curr. Opin. Biotechnol.* 7:60-65 (1996)). In an antigen capture assay, antibody is bound to a solid phase, and sample is added such that a MCY polypeptide antigen is bound by the antibody. After unbound proteins are removed by washing, the amount of bound antigen can be quantitated, if desired, using, for example, a radioassay (Harlow and Lane, *Antibodies A Laboratory Manual* Cold Spring Harbor Laboratory: New York, 1988)). Immunoassays can be performed under conditions of antibody excess, or as antigen competitions, to quantitate the amount of antigen and, thus, determine a level of expression of a MCY gene set polypeptide.

Enzyme-linked immunosorbent assays (ELISAs) can be useful in certain methods of the invention. In the case of an enzyme immunoassay, an enzyme is conjugated to the second antibody, generally by means of glutaraldehyde or periodate. As will be readily recognised, however, a wide variety of different conjugation techniques exist which are readily available to one skilled in the art. Commonly used enzymes include, for example, horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable color change. It is also possible to employ fluorogenic substrates, for example, which yield a fluorescent product. An enzyme such as horseradish peroxidase (HRP), alkaline phosphatase (AP), β-galactosidase or urease can be linked, for example, to an anti-adiponectin receptor C terminal fragment or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which can be used, for example, with the chromogenic substrate p-nitrophenyl phosphate to yield a soluble product readily detectable at 405 nm. Similarly, a β-galactosidase detection system can be used with, for example, the chromogenic substrate o-nitrophenyl-β-D-galactopyranoside (ONPG) to yield a soluble product detectable at 410 nm, or a urease detection system can be used with, for example, a substrate such as urea-bromocresol purple (Sigma Immunochemicals, St. Louis, Mo.). Useful enzyme-linked primary and secondary antibodies can be obtained from a number of commercial sources such as Jackson Immuno-Research (West Grove, Pa.).

In certain embodiments, a MCY polypeptide can be detected and measured using chemiluminescent detection. For example, in certain embodiments, MCY polypeptide specific antibodies are used to capture the polypeptides present in the biological sample and a antibody specific for the specific antibodies and labeled with an chemiluminescent label is used to detect the polypeptides present in the sample. Any chemiluminescent label and detection system can be used in the present methods. Chemiluminescent secondary antibodies can be obtained commercially from various sources such as Amersham. Methods of detecting chemiluminescent secondary antibodies are known in the art and are not discussed herein in detail.

Fluorescent detection also can be useful for detecting the adiponectin receptor fragments in certain methods of the invention. Useful fluorochromes include, for example, DAPI, fluorescein, lanthanide metals, Hoechst 33258, R-phycocyanin, B-phycoerythrin, R-phycoerythrin, rhodamine, Texas red and lissamine. Fluorescein or rhodamine labeled α2-MG-, HA-, TIMP-1- or YKL-40-specific binding agents such as anti-α2-MG, anti-HA, anti-TIMP-1, or anti-YKL-40 antibodies, or fluorescein- or rhodamine-labeled secondary antibodies can be useful in the invention. Useful fluorescent antibodies can be obtained commercially, for example, from Tago Immunologicals (Burlingame, Calif.) as described further below. Fluorescent compounds, can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope.

Radioimmunoassays (RIAs) also can be useful in certain methods of the invention. Such assays are well known in the art. Radioimmunoassays can be performed, for example, with $^{125}$I-labeled primary or secondary antibody (Harlow and Lane, supra, 1988).

A signal from a detectable reagent can be analyzed, for example, using a spectrophotometer to detect color from a chromogenic substrate; a radiation counter to detect radiation, such as a gamma counter for detection of $^{125}$I; or a fluorometer to detect fluorescence in the presence of light of a certain wavelength. Where an enzyme-linked assay is used, quantitative analysis of the amount of soluble adiponectin receptor fragments can be performed using a spectrophotometer such as an EMAX Microplate Reader (Molecular Devices; Menlo Park, Calif.) in accordance with the manufacturer's instructions. The assays of the invention can be automated or performed robotically, if desired, and that the signal from multiple samples can be detected simultaneously.

The methods of the invention also encompass the use of capillary electrophoresis based immunoassays (CEIA), which can be automated, if desired. Immunoassays also can be used in conjunction with laser-induced fluorescence as described, for example, in Schmalzing and Nashabeh, *Electrophoresis* 18:2184-93 (1997), and Bao, *J. Chromatogr. B. Biomed. Sci.* 699:463-80 (1997). Liposome immunoassays, such as flow-injection liposome immunoassays and liposome immunosensors, also can be used to detect a MCY gene set polypeptides or to determine a level of a MCY gene set polypeptide according to certain methods of the invention (Rongen et al., *J. Immunol. Methods* 204:105-133 (1997)).

Sandwich enzyme immunoassays also can be useful in certain methods of the invention. In a two-antibody sandwich assay, a first antibody is bound to a solid support, and the antigen is allowed to bind to the first antibody. The amount of a MCY gene set polypeptide can be quantitated by measuring the amount of a second antibody that binds to it.

Quantitative western blotting also can be used to determine a level of a MCY polypeptide in a method of the invention. Western blots can be quantitated by well known methods such as scanning densitometry. As an example, protein samples are electrophoresed on 10% SDS-PAGE Laemmli gels. Primary murine monoclonal antibodies are reacted with the blot, and antibody binding confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.* 28:669-675 (1998).

Levels of a MCY polypeptide can also be determined using protein microarrays. Methods of producing protein microarrays that can be adapted for detecting levels of protein in a clinical sample are described in the art (see for example of Xiao et al. (2005) Mol Cell Endocrinol.; 230(1-2):95-10; Protein Microarrays (2004) Mark Schena (Ed) Jones & Bartlett Publishers, Inc.). U.S. patent Pub. 2003/0153013 describes methods of detecting proteins, e.g. antigens or antibodies, by immobilizing antibodies in a protein microarray on a membrane and contacting the microarray with detection proteins which can bind to the proteins to form protein complexes. Similarly, U.S. patent Pub. 2004/0038428 describes methods of constructing protein microarrays.

In certain preferred embodiments, a biological sample, i.e., tumor cell, is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

Protein biochips are biochips adapted for the capture of peptides. Many protein biochips are described in the art. These include, for example, protein biochips produced by Ciphergen Biosystems, Inc. (Fremont, Calif.), Packard BioScience Company (Meriden CT), Zyomyx (Hayward, Calif.), Phylos (Lexington, Mass.) and Biacore (Uppsala, Sweden). Examples of such protein biochips are described in the following patents or published patent applications: U.S. Pat. No. 6,225,047; PCT International Publication No. WO 99/51773; U.S. Pat. No. 6,329,209, PCT International Publication No. WO 00/56934 and U.S. Pat. No. 5,242,828, incorporated herein by reference in their entirety and for all purposes.

For use herein, the assay methods can involve capturing MCY polypeptides onto a solid substrate. Typically they will be captured using a biospecific capture reagent such as an antibody and, in particular, an antibody used in an immunoassay. Biospecific capture reagents include those molecules that bind a target analyte with an affinity of at least $10^{-9}$ M, $10^{-10}$ M, $10^{-11}$ M or $10^{-12}$ M. These molecules also can be captured with non-specific methods, such as chromatographic materials.

In certain embodiments of the present invention, a MCY polypeptide can be detected by mass spectrometry. Examples of mass spectrometers are time-of-flight, magnetic sector, quadrupole filter, ion trap, ion cyclotron resonance, electrostatic sector analyzer and hybrids of these.

Other methods for identifying a cell that expresses MCY polypeptides or polynucleotides are also available to the skilled artisan. In certain embodiments, an assay for identifying a cell that expresses a MCY gene comprises detecting the presence of MCY mRNA in the cell. Methods for the detection of particular mRNAs in cells are well known and include, for example, hybridization assays using complementary DNA probes (such as in situ hybridization using labeled MCY gene set riboprobes, Northern blot and related techniques) and various nucleic acid amplification assays (such as RT-PCR using complementary primers specific for the MCY gene set, and other amplification type detection methods, such as, for example, branched DNA, SISBA, TMA and the like). Alternatively, an assay for identifying a cell that expresses a MCY gene comprises detecting the presence of MCY gene set protein in the cell or secreted by the cell.

Various methods for the detection of proteins are well known in the art and can be employed for the detection of MCY gene set proteins and MCY gene set-expressing cells.

MCY gene set expression analysis can also be useful as a tool for identifying and evaluating agents that modulate MCY gene expression. For example, MCY gene set expression is significantly upregulated in breast cancer, is also aberrantly expressed in other cancers. Identification of a molecule or biological agent that could inhibit MCY gene set expression or over-expression in cancer cells can be of therapeutic value. Such an agent can be identified by, for example, using a screen that quantifies MCY gene set expression by RT-PCR, nucleic acid hybridization or antibody binding.

X. Monitoring the Expression of the MCY Gene Set

For certain of the methods described herein, the level of expression of at least one gene selected from moesin, caveolin 1 or yes-associated protein 1 or any combination thereof is determined in different patient samples for which either diagnosis or prognosis information is desired, to provide profiles (i.e., detecting the level of moesin polynucleotides; caveolin-1 polynucleotides; yes-associated protein 1 polynucleotides, moesin and caveolin-1 polynucleotides; moesin and yes-associated protein 1 polynucleotides; caveolin-1 and yes-associated protein 1 polynucleotides; or moesin, caveolin-1, and yes-associated protein 1 polynucleotides). A profile of a particular sample is essentially a "fingerprint" of the state of the sample. A normal state can be distinguished from a disease state, and within disease states, different types of disease, and different prognosis states (good or poor long term survival prospects, for example) can be determined. Diagnosis can be done or confirmed by comparing patient samples with the known profiles. By assessing the evolution of the expression different times during disease progression, the stage of disease can be determined as well as the likely prognosis.

A principle of diagnostic testing is the correlation of the results of a procedure with particular clinical parameters. The correlation necessarily involves a comparison between two or more groups distinguished by the clinical parameter. A clinical parameter could be, for example, presence or absence of disease, risk of disease, stage of disease, severity of disease, class of disease or response to treatment of disease. Accordingly, the diagnostician uses this correlation to qualify the status of a subject with respect to the clinical parameter. That is, the diagnostician uses the results of a procedure on a subject to classify or diagnose a subject status with respect to a clinical parameter, the confidence of the diagnosis/classification being related to the classifying or splitting power of the signs or symptoms used in the test.

The methods described herein for qualifying or quantifying the expression of MCY polypeptides and polynucleotides provide information which can be correlated with pathological conditions, predisposition to disease, therapeutic monitoring, risk stratification, among others.

The present methods are particularly useful for diagnosing conditions, evaluating whether certain drugs will have a desired effect, i.e., determining responsiveness to a drug, and determining prognoses. The present methods can be used for early detection of diseases as well as for the optimization of treatment protocols.

For use herein, "diagnosing a condition" refers to determining whether or not a subject has an increased likelihood of having a specified condition. Tests that are used to diagnose a condition, such as the assays described herein, in certain instances, may not be able to diagnose a condition on their own but are used in combination with other tests to diagnose a condition. Accordingly "diagnosing a condition" is meant to include any methods that also aids in the diagnosis of a condition. The present invention can be used, for example, to determine whether a subject has an increased likelihood of having a certain type of cancer and/or a certain type of breast cancer, i.e., triple negative breast cancer or basal subtype breast cancer.

Certain embodiments of the invention provide methods for examining MCY gene expression to predict the breast cancer's sensitivity to N-(2-chloro-6-methylphenyl)-2-[[6-[4-(2-hydroxyethyl)-1-piperazinyl]-2-methyl-4-pyrimidinyl] amino]-5-thiazolecarboxamide or a pharmaceutically acceptable salt, solvate, or hydrate thereof. A typical embodiment of this invention provides methods for examining MCY gene expression in various breast cancers, for example the basal subtype of breast cancer, where expression of this gene set in the cancer cell is correlated to that cell's sensitivity to N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof. As noted herein, this disclosure provides a pharmocogenomic approach that identifies a specific cancer phenotype (characterized by expression of the MCY gene set) that responds to N-(2-chloro-6-methylphenyl)-2-[[6-[4-(2-hydroxyethyl)-1-piperazinyl]-2-methyl-4-pyrimidinyl] amino]-5-thiazolecarboxamide or a pharmaceutically acceptable salt, solvate, or hydrate thereof. Those of skill in the art will note that this phenotype is also likely to respond to dasatinib analogues, i.e. those compounds related to dasatinib via structure and/or by modulating the function of the same biological target (BCR-ABL and SRC kinases) of this molecule.

Assays that evaluate the status of MCY polynucleotides and polypeptides in an individual can provide information on the growth or oncogenic potential of a biological sample from this individual. For example, because MCY mRNA is so highly expressed in certain breast cancer cells as compared to normal breast tissue, assays that evaluate the relative levels of MCY mRNA transcripts or proteins in a biological sample can be used to diagnose a disease associated with MCY gene set disregulation such as cancer and can provide prognostic information that can for example be useful in defining appropriate therapeutic options. Similarly, assays that evaluate the integrity of MCY nucleotide and amino acid sequences in a biological sample, can also be used in this context.

The finding that MCY mRNA is so highly expressed in certain breast cancer subtypes provides evidence that this gene is associated with disregulated cell growth and therefore identifies this gene and its products as targets that the skilled artisan can use to evaluate biological samples from individuals suspected of having a disease associated with MCY disregulation. In this context, the evaluation of the status of MCY polynucleotides and/or polypeptides can be used to gain information on the disease potential of a tissue sample.

The term "status" in this context is used according to its art accepted meaning and refers to the condition a gene and its products including, but not limited to the integrity and/or methylation of a gene including its regulatory sequences, the location of expressed gene products (including the location of MCY gene set expressing cells), the presence, level, and biological activity of expressed gene products (such as MCY mRNA polynucleotides and polypeptides), the presence or absence of transcriptional and translational modifications to expressed gene products as well as associations of expressed gene products with other biological molecules such as protein binding partners. Alterations in the status of the MCY gene set can be evaluated by a wide variety of methodologies well known in the art, typically those discussed below. Typically an alteration in the status of the MCY gene set comprises a change in the location of MCY gene set expressing cells, an increase in MCY mRNA and/or protein expression and/or the association or dissociation of the MCY polypeptide with a binding partner.

The expression profile of the MCY gene set makes it a diagnostic marker for local and/or metastasized breast cancer disease. In particular, the status of the MCY gene set provides information useful for predicting susceptibility to particular disease stage or subtype, progression, and/or tumor aggressiveness. The invention provides methods and assays for determining MCY gene set status and characterizing cancers that express the MCY gene set, such as cancers of the breast. MCY gene set status in patient samples can be analyzed by a number of means well known in the art, including without limitation, immunohistochemical analysis, in situ hybridization, RT-PCR analysis on laser capture micro-dissected samples, western blot analysis of clinical samples and cell lines, and tissue array analysis. Typical protocols for evaluating the status of the MCY gene set gene and gene products can be found, for example in Ausubul et al. eds., 1995, Current Protocols In Molecular Biology, Units 2 [Northern Blotting], 4 [Southern Blotting], 15 [Immunoblotting] and 18 [PCR Analysis].

As described above, the status of the MCY gene set in a biological sample can be examined by a number of well known procedures in the art. For example, the status of the MCY gene set in a biological sample taken from a specific location in the body can be examined by determining the level of MCY gene set expressing cells (e.g. those that express MCY polynucleotides (e.g., mRNA or proteins). This examination can provide evidence of disregulated cellular growth for example, when MCY gene set expressing breast cells are found in a biological sample that does not normally contain such cells (such as a lymph node, bone or spleen) or contains them but a different level. Such alterations in the status of the MCY gene set in a biological sample are often associated with disregulated cellular growth. Specifically, one indicator of disregulated cellular growth is the metastases of cancer cells from an organ of origin (such as the breast gland) to a different area of the body (such as a lymph node). In this context, evidence of disregulated cellular growth is important for example because occult lymph node metastases can be detected in a substantial proportion of patients with breast cancer, and such metastases are associated with known predictors of disease progression (see, e.g. Gipponni et al., J Surg Oncol. 2004 Mar. 1; 85(3):102-111).

In certain aspects, the invention provides methods for monitoring MCY gene products by determining the status of MCY polynucleotides and/or polypeptides expressed by cells in a test tissue sample from an individual suspected of having a disease associated with disregulated cell growth (such as hyperplasia or cancer) and then comparing the status so determined to the status of MCY polynucleotides and/or polypeptides in a corresponding normal sample, the presence of aberrant MCY polynucleotides and/or polypeptides in the test sample relative to the normal sample providing an indication of the presence of disregulated cell growth within the cells of the individual.

In another aspect, the invention provides assays useful in determining the presence of cancer in an individual, comprising detecting a significant increase in MCY mRNA or protein expression in a test cell or tissue sample relative to expression levels in the corresponding normal cell or tissue. The presence of MCY mRNA can, for example, be evaluated in tissue samples including but not limited to breast cancer subtypes such as basal and BRCA 1 breast cancer subtypes (see, e.g.

Sorlie et al., PNAS (2001), 98(19): 10869-10874), etc. The presence of significant MCY gene set expression in any of these tissues is useful to indicate the emergence, presence and/or severity of these cancers, since the corresponding normal tissues do not express MCY mRNA or express it at lower levels.

In a related embodiment, MCY gene set status can be determined at the protein level rather than at the nucleic acid level. For example, such a method or assay can comprise determining the level of MCY protein expressed by cells in a test tissue sample and comparing the level so determined to the level of MCY protein expression in a control sample, i.e., a corresponding normal sample. In one embodiment, the presence of MCY protein is evaluated, for example, using immunohistochemical methods. MCY antibodies or binding partners capable of detecting MCY protein expression can be used in a variety of assay formats well known in the art for this purpose.

In other related embodiments, one can evaluate the integrity of MCY nucleotide and amino acid sequences in a biological sample in order to identify perturbations in the structure of these molecules such as insertions, deletions, substitutions and the like. Such embodiments are useful because perturbations in the nucleotide and amino acid sequences are observed in a large number of proteins associated with a growth disregulated phenotype (see, e.g., Marrogi et al., 1999, J. Cutan. Pathol. 26(8):369-378). In this context, a wide variety of assays for observing perturbations in nucleotide and amino acid sequences are well known in the art. For example, the size and structure of nucleic acid or amino acid sequences of MCY gene products can be observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. Nos. 5,382,510 and 5,952,170).

In certain other embodiments one can examine the methylation status of the MCY gene in a biological sample. Aberrant demethylation and/or hypermethylation of CpG islands in gene 5' regulatory regions frequently occurs in immortalized and transformed cells and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985-1992 (1999)). In addition, this alteration is present in at least 70% of cases of high-grade prostatic intraepithelial neoplasia (PIN) (Brooks et al, Cancer Epidemiol. Biomarkers Prev., 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., Int. J. Cancer 76(6): 903-908 (1998)). In this context, a variety of assays for examining methylation status of a gene are well known in the art. For example, one can utilize in Southern hybridization approaches methylation-sensitive restriction enzymes which can not cleave sequences that contain methylated CpG sites in order to assess the overall methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in *Current Protocols* In Molecular Biology, Units 12, Frederick M. Ausubul et al. eds., 1995.

In addition to the tissues discussed above, peripheral blood can be conveniently assayed for the presence of cancer cells, including but not limited to breast cancers, using for example, Northern or RT-PCR analysis to detect MCY gene set expression. The presence of RT-PCR amplifiable MCY mRNA provides an indication of the presence of the cancer. RT-PCR detection assays for tumor cells in peripheral blood are currently being evaluated for use in the diagnosis and management of a number of human solid tumors.

A related aspect of the invention is directed to predicting susceptibility to developing cancer in an individual. In one embodiment, a method for predicting susceptibility to cancer comprises detecting MCY mRNA or MCY protein in a tissue sample, its presence indicating susceptibility to cancer, wherein the degree of MCY mRNA expression present is proportional to the degree of susceptibility. In a specific embodiment, the presence of the MCY polynucleotides and/or polypeptides in breast tissue is examined, with the presence of the MCY polynucleotides and/or polypeptides in the sample providing an indication of that breast cancer's susceptibility to N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof (or the emergence or existence of a breast tumor and/or the emergence or existence of a specific breast tumor subtype).

Yet another related aspect of the invention is directed to methods for evaluating tumor aggressiveness. In one embodiment, a method for evaluating aggressiveness of a tumor comprises determining the level of MCY polynucleotides, e.g., RNA, or MCY protein expressed by cells in a sample of the tumor, comparing the level so determined to the level of MCY polynucleotides, e.g., mRNA or MCY gene set protein expressed in a control, i.e., corresponding normal tissue taken from the same individual or a normal tissue reference sample, wherein the degree of MCY mRNA or MCY protein expression in the tumor sample relative to the normal sample indicates the degree of aggressiveness. In a specific embodiment, aggressiveness of a tumor is evaluated by determining the extent to which the MCY gene set is expressed in the tumor cells, with higher expression levels indicating more aggressive tumors. In a closely related embodiment, one can evaluate the integrity of MCY nucleotide and amino acid sequences in a biological sample in order to identify perturbations in the structure of these molecules such as insertions, deletions, substitutions and the like, with the presence of one or more perturbations indicating more aggressive tumors.

Methods for detecting and quantifying the expression of MCY polynucleotides, e.g., mRNA, or protein are described herein and use of standard nucleic acid and protein detection and quantification technologies is well known in the art. Standard methods for the detection and quantification of MCY mRNA include in situ hybridization using labeled MCY gene set riboprobes, Northern blot and related techniques using MCY polynucleotide probes, RT-PCR analysis using primers specific for the MCY gene set, and other amplification type detection methods, such as, for example, branched DNA, SISBA, TMA and the like. In a specific embodiment, RT-PCR can be used to detect and quantify MCY mRNA expression as described in the Examples. Any number of primers capable of amplifying MCY mRNA can be used for this purpose. Standard methods for the detection and quantification of protein can be used for this purpose. In a specific embodiment, polyclonal or monoclonal antibodies specifically reactive with the wild-type MCY protein can be used in an immunohistochemical assay of biopsied tissue.

The present invention provides methods of examining a test biological sample comprising a human breast cell for evidence of gene expression indicative of sensitivity to therapy with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof by evaluating the levels of at least one of a MCY polynucleotide (including any combination thereof e.g., moesin polynucleotides; caveolin-1 polynucleotides; yes-associated protein 1 polynucleotides; moesin and caveolin-1 polynucleotides; moesin and yes-associated protein 1 polynucleotides; caveolin-1 and yes-associated protein 1 polynucleotides and moesin, caveolin-1, and yes-associated protein 1 polynucleotides), wherein the level of expression of at least one of the MCY polynucleotides in the test sample is indicative of a breast cancer that is sensitive to therapy with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof. In certain embodiments, the levels of the MCY polynucleotides in the cell are evaluated by contacting the sample with a MCY complementary polynucleotide that hybridizes to a MCY nucleotide sequence shown in Table 1, or a complement thereof, and evaluating the presence of a hybridization complex formed by the hybridization of the MCY—complementary polynucleotide with the MCY polynucleotides in the test biological sample. In certain preferred embodiments, elevated levels of least one of, at least two of, or all three of the MCY polynucleotides in the test sample is indicative of a breast cancer that is sensitive to the therapy.

A related embodiment is a method of examining a human breast cell for evidence of gene expression indicative of sensitivity to therapy with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof by evaluating the levels of moesin (e.g., SEQ ID NO: 1 or a sequence having substantial identity to SEQ ID NO: 1), caveolin 1 (SEQ TD NO: 2 or a sequence having substantial identity to SEQ TD NO: 2) and/or yes-associated protein 1 (SEQ ID NO: 3 or a sequence having substantial identity to SEQ ID NO: 3) (MCY gene set) polynucleotides that encode the MCY gene set polypeptide shown in Table 1 in the human breast cell, wherein expression of the MCY gene set polynucleotides (e.g. mRNAs and genomic sequences) in the human breast cell provides evidence of sensitivity to N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof. In certain embodiments, the levels of the MCY polynucleotides in the human breast cell are evaluated by contacting the endogenous MCY polynucleotide sequences in the human breast cell with a MCY complementary polynucleotide the MCY complementary polynucleotide (e.g. a probe labelled with a detectable marker or a PCR primer) and which specifically hybridizes to a MCY nucleotide sequence shown in Table 1 and evaluating the presence of a hybridization complex formed by the hybridization of the MCY complementary polynucleotide with the MCY polynucleotides in the sample (e.g. via Northern analysis or PCR) so that evidence of altered cell growth that is associated with or provides evidence of a breast cancer is examined.

In some embodiments of the invention, the increase in the levels of the MCY polynucleotides and/or polypeptides in the human breast cell relative to a normal human breast cell is quantified. A normalized standard that can be used as a comparative reference of MCY gene set expression can for example be obtained from normal breast tissue taken from the same individual, or a normal tissue reference sample taken from a healthy individual. Alternatively, a normalized standard can be a numerical range of normal MCY gene set expression that is obtained from a statistical sampling of normal cells from a population of individuals. In certain embodiments of the invention, the normalized standard is derived by comparing MCY gene set expression to a control gene that is expressed in the same cellular environment at relatively stable levels (e.g. a housekeeping gene such as an actin).

In certain embodiments of the invention, the breast cancer is of the basal subtype. As is known in the art, cancers of the breast can be group into a number of distinct subtypes, including a basal subtype (see, e.g. see, e.g. Sorlie et al., PNAS (2001), 98(19): 10869-10874, incorporated herein by reference in its entirety and for all purposes). In particular, mammary ducts are bilayered structures composed of a luminal layer and a myoepithelial layer that adhere to a basement membrane. The term basal subtype is an art accepted term that refers to certain cancers that arise from the basal layer of the stratified epithelia (see, e.g. FIG. 1 in Wilson et al. Breast Cancer Research Vol 6 No. 5: 192-200 (2004)). Breast carcinomas of the basal subtype reside in the basal layer of the ductal epithelium of the breast as opposed to the apical or luminal layers. Such cancers have distinct cytological features and gene expression profiles such as an intermediate filament profile (cytokeratins) first observed in the basal cells of the skin. In particular, basal cells in the skin are known to express certain cytokeratins (i.e. K5/6, K7, K17, K14) (see, e.g., SEQ ID NO: 10, SEQ ID NO: 11, SEQ ID NO: 12, SEQ ID NO: 13, and SEQ ID NO: 14) which are found in complex epithelia as opposed to K8, K18, K19 which are found in simple, or glandular epithelia.

In certain embodiments of the invention, the breast cancer is of the mesenchymal subtype. For discussions of this type of breast cancer, see, e.g. Tsuda et al., Cancer Sci. 2005 January; 96(1):48-53; Ulusoy et al, Breast J. 2005 September-October; 11(5):358-9; Reis-Filho J S, J Pathol. 2005 November; 207 (3):367-369; Korsching et al., J Pathol. 2005 August; 206(4): 451-7; and Strizzi et al., J Cell Physiol. 2004 November; 201(2):266-76, the contents of which are incorporated herein by reference in their entirety and for all purposes.

A subtype of breast cancer (e.g. one with basal cell properties) can be readily determined via pathology-IHC data and/or the Stanford breast tumor profiling data disclosed herein. For example, Wetzels et al, Am J Path. (1991) 138: p 751-63 which is incorporated herein by reference describe basal cell-specific and hyperproliferations-related keratins in human breast cancer. This study found that 15% (n=115) of invasive breast cancers were positive for basal cytokeratins 14 and 17. In addition, Bartek et al., Int J. Cancer (1985) 36:299-306 which is incorporated herein by reference also teach the characterization of breast cancer subtypes using patterns of expression of K19 in human breast tissues and tumors. Conversely, most medullary and poorly differentiated ductal carcinomas were negative for cytokeratin 19 while moderately and well-differentiated ductal, invasive lobular, tubular and most mucinous carcinomas were positive with both K19 Abs. In addition, P-Cadherin (CDH3) and Desmosomal Cadherins are expressed in Basal Layer of Breast Ducts and P-Cadherin mRNA is overexpressed in the basal and BRCA1 subtypes.

This provides confirmatory evidence that the Group 4 and BRCA1 tumor groups share many molecular properties associated with cell type origin.

Paredes et al., Pathol. Res. Pract. 2002: 198(12): 795-801 which is incorporated herein by reference also investigate the expression of P cadherin in breast carcinoma subtypes and correlate it with estrogen receptor (ER) (see, e.g., SEQ ID NO: 7) status. 73 ductal carcinomas in situ (DCIS) and 149 invasive carcinomas of the breast were selected and examined for the expression of P-cadherin as well as other biologic markers. P-cadherin expression showed a strong inverse correlation with estrogen receptor (ER) expression in both types of breast carcinoma (in situ and invasive). P-cadherin-positive and ER-negative tumors were related to a higher histologic grade, a high proliferation rate, and expression of c-erbB-2. This demonstrates that P-cadherin identifies a subgroup of breast carcinomas that lacks ER expression, and correlates with higher proliferation rates and other predictors of aggressive behavior. See also, Gamallo et al., Mod. Pathol. 2001: 14(7): 650-4; Kovacs et al., J Clin Pathol 2003 February; 56(2):139-41; and Peralta et al., Cancer 1999 Oct. 1; 86(7):1263-72 which are incorporated herein by reference.

In certain embodiments of the invention, the breast cancer is of the BRCA1 subtype. In particular, as is known in the art, cancers of the breast can be group into a number of distinct subtypes, including a BRCA1 subtype (see, e.g. see, e.g. Sortie et al., PNAS (2001), 98(19): 10869-10874). In this context, a breast cancer of the BRCA1 subtype is characterized as having a mutation in the BRCA1 gene. A variety of distinct BRCA1 mutations are known to occur in multiple tissues and include substitutions, deletions and missense mutations (see, e.g. Wagner et al., Int J Cancer. 1998 Jul. 29; 77(3):354-60; Chang et al., Breast Cancer Res Treat. 2001 September; 69(2):101-13; and Foulkes et al., Cancer Res. 2004 Feb. 1; 64(3):830-5; and Aghmesheh et al., Gynecol Oncol. 2005 April; 97(1):16-25 which are incorporated herein by reference). The Basal and BRCA1 cancers are related by cellular origin and molecular pathogenesis and the over-expression of MCY gene set is an important alteration involved in the pathogenesis of these two tumor groups.

The present invention also provides methods of examining a test biological sample comprising a human breast cell for evidence of gene expression indicative of sensitivity to therapy with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof, the method comprising evaluating the levels of at least one of a moesin (e.g., SEQ ID NO: 4 or a sequence having substantial identity to SEQ ID NO:4), caveolin 1 (e.g., SEQ ID NO: 5 or a sequence having substantial identity to SEQ ID NO:5), and yes-associated protein 1 (e.g., SEQ ID NO: 6 or a sequence having substantial identity to SEQ ID NO:6) (MCY gene set) polypeptide (e.g., having the sequence shown in Table 1 or having substantial identity to a sequence shown in Table 1) in the biological sample, wherein an increase in the levels of the MCY polypeptides in the test sample relative to a normal breast tissue sample provide evidence of sensitivity to therapy with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof. In certain embodiments, the levels of the MCY polypeptides in the cell are evaluated by contacting the sample with an antibody that immunospecifically binds to a MCY polypeptide sequence shown in Table 1 and evaluating the presence of a complex formed by the binding of the antibody with the MCY polypeptides in the sample.

A related embodiment of the invention is a method of examining a human breast cell (e.g. from a biopsy) for evidence of gene expression indicative of sensitivity to therapy with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof that is indicative of a breast cancer, the method comprising evaluating the levels of at least one of a moesin, caveolin 1 and yes-associated protein 1 (or any combination thereof) polypeptide (e.g., having the sequence shown in Table 1 or sequences having substantial identity to those shown in Table 1) in the breast cell, wherein the level of expression of the MCY polypeptides in the human breast cell provide evidence of sensitivity to therapy with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof. In certain embodiments, the levels of the MCY polypeptides in the cell are evaluated by contacting the sample with an antibody (e.g. one labelled with a detectable marker) that immunospecifically binds to a MCY polypeptide sequence shown in Table 1 and evaluating the presence of a complex formed by the binding of the antibody with the MCY gene set polypeptides in the sample. In certain embodiments, the presence of a complex is evaluated by a method selected from the group consisting of ELISA analysis, Western analysis and immunohistochemistry. Typically, the breast cancer is of the basal subtype.

XI. Treatment Regimens

The invention encompasses treatment methods based upon the demonstration that patients harboring different levels of expression of the moesin, caveolin 1 and/or yes associated protein 1 gene have varying degrees of resistance and/or sensitivity to therapy with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof. Thus the methods of the present invention can be used, for example, in determining whether or not to treat an individual with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof, whether or not to treat an individual with a more aggressive dosage regimen of N-(2-chloro-6-methylphenyl)-2-[[6-[4-(2-hydroxyethyl)-1-piperazinyl]-2-methyl-4-pyrimidinyl] amino]-5-thiazolecarboxamide or a pharmaceutically acceptable salt, solvate, or hydrate thereof; or whether or not to treat an individual with combination therapy, i.e., a combination of N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof with an additional anti-cancer therapy. The terms "treating", "treatment" and "therapy" as used herein refer to curative therapy, prophylactic therapy, preventative therapy, and mitigating disease therapy.

The actual dosage employed of N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof can be varied depending upon the requirements of the patient and the severity of the condition being treated. Determination of the proper dosage for a particular situation is within the skill of the art. The effective amount of N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof can be determined by one of ordinary skill in the art, and includes exemplary dosage amounts for an adult human of from about 0.05 to about 100 mg/kg of body weight of N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof, per day, which can be administered in a single dose or in the form of individual divided doses, such as from 1, 2, 3, or 4 times per day. It will be understood that the specific dose level and frequency of dosing for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

A treatment regimen is a course of therapy administered to an individual suffering from a disease described herein that can include treatment with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof and/or other anticancer therapies. When more than one therapy is administered, the therapies can be administered concurrently or consecutively. Administration of more than one therapy can be at different times (i.e., consecutively) and still be part of the same treatment regimen.

Accordingly, in one aspect of the invention, if at least one member, at least two members, or all three members of the MCY polynucleotide or polypeptide set are expressed in breast cancer cells as outlined herein, the treatment regimen may only require administration of N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof to either kill or inhibit the proliferation of said cancer. Such administration may include a pharmaceutically acceptable amount of N-(2-chloro-6-methylphenyl)-2-[[6-[4-(2-hydroxyethyl)-1-piperazinyl]-2-methyl-4-pyrimidinyl]amino]-5-thiazolecarboxamide or a salt, hydrate, or solvate thereof, a combination of N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, hydrate, or solvate thereof.

Alternatively, if at least one member, at least two members, or all three members of the MCY polynucleotide or polypeptide set are not expressed in breast cancer cells, or if less then optimal levels (e.g., levels that are high enough to predict sensitivity to dasatinib) of a MCY predictor polynucleotide set member expression is observed, the treatment regimen may require either increased dosing frequency or a higher dose of N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof, and/or a combination of N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof with another pharmaceutically acceptable agent including another anti-cancer agent such as a kinase inhibitor drug such as imatinib, AMN107, PD180970, GGP76030, AP23464, SKI 606, and/or AZDO530; a combination of N-(2-chloro-6-methylphenyl)-2-[[6-[4-(2-hydroxyethyl)-1-piperazinyl]-2-methyl-4-pyrimidinyl]amino]-5-thiazolecarboxamide and a tubulin stabilizing agent (e.g., pacitaxol, epothilone, taxane, and the like.); a combination of N-(2-chloro-6-methylphenyl)-2-[[6-[4-(2-hydroxyethyl)-1-piperazinyl]-2-methyl-4-pyrimidinyl]amino]-5-thiazolecarboxaimide and a farnysyl transferase inhibitor (including (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile, hydrochloride salt described in U.S. Pat. No. 6,011,029); and any other combination or dosing regimen comprising N-(2-chloro-6-methylphenyl)-2-[[6-[4-(2-hydroxyethyl)-1-piperazinyl]-2-methyl-4-pyrimidinyl]amino]-5-thiazolecarboxamide. In one aspect, an increased dose of N-(2-chloro-6-methylphenyl)-2-[[6-[4-(2-hydroxyethyl)-1-piperazinyl]-2-methyl-4-pyrimidinyl]amino]-5-thiazolecarboxamide would be about 10, 20, 30, 40, 50, 60, 70, 80, 90, or 95% more than the typical N-(2-chloro-6-methylphenyl)-2-[[6-[4-(2-hydroxyethyl)-1-piperazinyl]-2-methyl-4-pyrimidinyl]amino]-5-thiazolecarboxamide dose for a particular indication or for individual, or about 1.5×, 2×, 2.5×, 3×, 3.5×, 4×, 4.5×, 5×, 6×, 7×, 8×, 9×, or 10× more N-(2-chloro-6-methylphenyl)-2-[[6-[4-(2-hydroxyethyl)-1-piperazinyl]-2-methyl-4-pyrimidinyl]amino]-5-thiazolecarboxamide than the typical N-(2-chloro-6-methylphenyl)-2-[[6-[4-(2-hydroxyethyl)-1-piperazinyl]-2-methyl-4-pyrimidinyl]amino]-5-thiazolecarboxamide dose for a particular indication or for individual. In particular, N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, hydrate, or solvate thereof may typically be administered 2 times per day at 70 mg, however, it can be dosed at, other amounts, for example, 50, 70, 90, 100, 110, or 120 BID, or 100, 140, or 180 once daily, twice daily, or thrice daily.

In practicing the many aspects of the invention herein, biological samples can be selected from many sources such as tissue biopsy (including cell sample or cells cultured therefrom; biopsy of solid tissue, for example cells from a solid tumor), blood, blood cells (red blood cells or white blood cells), serum, plasma, lymph, ascetic fluid, cystic fluid, urine, sputum, stool, saliva, bronchial aspirate, CSF or hair Cells from a sample can be used, or a lysate of a cell sample can be used. In certain embodiments, the biological sample is a tissue biopsy cell sample or cells cultured therefrom, for example, cells removed from a solid tumor or a lysate of the cell sample. In certain embodiments, the biological sample comprises blood cells.

XII. Kits

For use in the diagnostic and therapeutic applications described or suggested above, kits are also provided by the invention. Such kits can comprise a carrier means being compartmentalized to receive in close confinement one or more container means such as vials, tubes, and the like, each of the container means comprising one of the separate elements to be used in the method. For example, one of the container means can comprise a probe that is or can be detectably labeled. Such probe can be an antibody or polynucleotide specific for a MCY protein (e.g., SEQ ID NO: 4, SEQ ID NO: 5, and SEQ ID NO: 6) or a MCY polynucleotide (e.g., SEQ ID NO: 1, SEQ ID NO: 2, and SEQ ID NO: 3), respectively. Where the kit utilizes nucleic acid hybridization to detect the target nucleic acid, the kit can also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

A typical embodiment of the invention is a kit comprising a container, a label on said container, and a composition contained within said container; wherein the composition includes a MCY gene set specific antibody and/or a polynucleotide that hybridizes to a complement of the MCY polynucleotide shown in Table 1 under stringent conditions (or binds to a MCY polypeptide encoded by the polynucleotide shown in Table 1). In certain aspects, the label on said container indicates that the composition can be used to evaluate the presence of MCY protein, RNA or DNA in at least one type of mammalian cell, and includes instructions for using the MCY antibody and/or polynucleotide for evaluating the presence of MCY protein, RNA or DNA in at least one type of mammalian cell.

The kit of the invention will typically comprise the container described above and one or more other containers comprising materials desirable from a commercial and user standpoint, including buffers, diluents, filters, needles, syringes, and package inserts with instructions for use. A label can be present on the container to indicate that the composition is used for a specific therapy or non-therapeutic application, and may also indicate directions for either in vivo or in vitro use, such as those described above.

EXAMPLES

Example 1

General Method for Identification of Predictive Markers for Response to Dasatinib Cells were cultured using standard techniques and specific medias Dose response curves were generated using direct cell counts. Approximately 10-20,000 cells per well were plated in 24-well dishes on day 0. On day 1 dasatinib was diluted across the plate in ½ dilutions, from 10 uM down. For each cell line, untreated controls were also used as controls. Cells were incubated for 7 days at which time the wells were rinsed with PBS, cells were trypsinized and counted using a Coulter counter. Dose response curves were generated as % inhibition of control. Microarray profiles were generated as described (Wilson C A et al., Breast Cancer Research 7 (suppl 2): 4.25) Cell lines were separated into resistant and sensitive based on their dose response curves. Data matrices were used to find discriminating genes for predicting sensitivity to dasatinib.

Example 2

Cell Lines, Cell Culture and Reagents

The effects of dasatinib on cell growth were studied in human breast cancer cell lines growing in vitro. The cell lines MDA-MB-415, MDA-MB-134, HCC-1500, ZR-75-30, HCC-202, HCC-1419, HCC-38, HCC-70, HCC-1187, HCC-1806, HCC-1937, HCC-1954, MDA-MB-436, HCC-1569, Hs578t, HCC-1143, MDA-MB-175, BT-474, SK-BR-3, MDA-MB-361, UAC-893, UACC-812, UACC-732, T-47D, MDA-MB-453, MDA-MB-468, CAMA-1, MDA-MB-157, MCF-7, MDA-MB-435, ZR-75-1, BT-20, and MDA-MB-231 were obtained from American Type Culture Collection (Rockville, Md.). The cell lines EFM-192A, KPL-1, EFM-19 and CAL-51 were obtained from the German Tissue Repository DSMZ (Braunschweig Germany), and the cell lines SUM-190 and SUM-225 were obtained from the University of Michigan (Ann Arbor, Mich.). MDA-MB-134, MDA-MB415, MDA-MB-436, MDA-MB-175, UACC-893, UACC-812, and MDA-MB-157 cells were cultured in L15 medium supplemented with 10% heat-inactivated fetal bovine serum (FBS), 2 nmol/L glutamine and 1% penicillin G-streptomycin-fungizone solution (PSF, Irvine Scientific, Santa Ana, Calif.). CAL-51, KPL-1, Hs578t cells were grown in DMEM supplemented with 10% heat-inactivated FBS and PSF, as above. SUM-190 and SUM-225 cells were cultured in HAM's F12 supplemented with 5% heat-inactivated FBS, PSF, 5 mg/ml insulin and 1 mg/ml hydrocortisone. The remaining cell lines were cultured in RPMI 1640 supplemented with 10% heat-inactivated FBS, 2 mmol/L glutamine, and PSF.

Example 3

Microarray Analysis of Cell Lines

Agilent microarray analyses were developed for each cell line (see, e.g., Wilson C A, et al., Breast Cancer Research. 2005, 7 Suppl 2:S 4.25). Briefly, cells were grown to log phase and then RNA was extracted using the RNeasy Kit (Qiagen). The purified RNA was eluted in 30-60 ul DEPC water and the quantity of RNA measured by spectral analysis using the Nanodrop Spectrophotometer. RNA quality was determined by separation of the RNA via capillary electrophoresis using the Agilent 2000 Bioanalyzer. Microarrays of breast cancer cell lines were then performed on the Agilent Human 1A V1 chip. Characterization of individual breast cancer cell lines by comparison to a breast cell line mixed reference pool was conducted on a single slide in which the mixed pool RNA was labeled with cyanine-3 and the individual cell lines with cyanine-5. The mixed reference pool consisted of equal amounts of cRNA from ten breast cancer cell lines that were selected to be representative of a range of the various known breast cancer subtypes based on their expression of specific molecular markers, e.g. ESR1, HER2, EGFR, as well as growth characteristics. The reference includes the following cell lines: 184B5, MDA-MB-468, MDA-MB-157, MDA-MB-231, MDA-MB-175, CAMA-1, MCF-7, MDA-MB-361, SK-BR-3, and DU4475. Microarray slides were read using an Agilent Scanner and the Agilent Feature Extraction software version 7.5 was used to calculate gene expression values. Extracted data was imported into Rosetta Resolver 5.1 to create expression profiles for each individual breast cell line experiment. Cluster analysis was performed in Resolver and cell line profiles were exported to Excel (Microsoft) for additional analysis of the distribution of gene expression changes across the various subtypes and the individual cell line response data.

Example 4

Proliferation Assays

Cells were seeded in duplicate at 5,000 to 10,000 cells per well in 24-well plates. The day after plating, dasatinib was added at a final concentration of 1 µM. Control wells without drug were seeded as well. Both the adherent and floating fractions of cells were counted on days 2, 5 and 7 for both treatment and control wells. After trypsinization cells were placed in Isotone solution and counted immediately using a Coulter Z2 particle counter (Beckman Coulter Inc, Fullerton, Calif.).

Growth inhibition was calculated [(1−experimental value/control value)×100] for each day adding both the values obtained for the floating cells and the adherent cells. Pearson-Chi-square analysis was performed to identify a correlation between subtype and sensitivity to dasatinib. Dasatinib was a gift from Frank Lee at Bristol-Meyers-Squibb.

Example 5

Statistical Methods

Pearson chi squared tests were performed using Statistica 7.1 (Statsoft Inc) to determine the relationship (if any) between subtype and dasatinib response. Genes potentially related to response were determined by analyzing the distribution of samples with significant expression changes across cell line groups defined by subtype and response for each gene. The threshold for up-regulation was set to log(ratio) >0.13 with a p-value <0.01 and down-regulation was defined as log(ratio)<−0.13 with a p-value <0.01. The p-values were determined according to the Agilent error model when the feature-extracted data was imported into Resolver. Gene ontology and pathway information was used to further constrain the set of candidate markers. Clustering was then used to visualize expression of candidate markers across all the cell lines tested for dasatinib response to develop a potentially sensitive and specific "response predictor marker set" of genes.

Example 6

Dasatinib Inhibits Growth of "Basal-type" Breast Cancer

A total of 39 breast cancer cell lines were categorized as representing luminal or basal breast cancer subtypes based on the relative gene expression of Cytokeratin (CK) 8/CK18 and CK5/CK17, respectively. In addition, several cell lines were classified as representing breast cancers that had undergone an epithelial-to-mesenchymal transition (post-EMT) based on their expression of vimentin and the loss of cytokeratins expression. A cluster diagram of the 39 breast cancer cell lines versus 5 subtype markers was developed. The cell lines that show mixed cytokeratin expression were classified as primarily basal on the lack of expression of several other well-characterized luminal additional markers: e.g. estrogen receptor, E-cadherin (CDH1), and GATA3. The relative expression of the above markers as well as estrogen receptor and HER-2 expression levels was used to assign the various cell lines into previously clinically defined subtypes (see, e.g., Sorlie T et al., Proc Natl Acad Sci USA. 2001 Sep. 11; 98: 10869-74; Sotiriou C, et al., Proc Natl Acad Sci USA. 2003 Sep. 2; 100(18): 10393-8; Perou C M, et al., Nature. 2000 Aug. 17; 406(6796):747-52). Response to dasatinib was then assigned to each cell line along with the subtype of breast cancer it represents as provided in Table 2 below.

TABLE 2

| Cell Line | Breast Cancer Subtype | ER Status | HER-2 Status | Response to Dasatinib in vitro |
|---|---|---|---|---|
| MDA-MB-453 | Luminal | Negative | Amplified | Resistant |
| SK-BR-3 | Luminal | Negative | Amplified | Resistant |
| SUM-190 | Luminal | Negative | Amplified | Resistant |
| SUM-225 | Luminal | Negative | Amplified | Resistant |
| UACC-893 | Luminal | Negative | Amplified | Resistant |
| EFM-192A | Luminal | Positive | Amplified | Resistant |
| HCC-202 | Luminal | Positive | Amplified | Resistant |
| UACC-732 | Luminal | Positive | Amplified | Resistant |
| UACC-812 | Luminal | Positive | Amplified | Resistant |
| ZR-75-30 | Luminal | Positive | Amplified | Resistant |
| HCC-1500 | Luminal | Positive | Normal | Resistant |
| KPL-1 | Luminal | Positive | Normal | Resistant |
| MDA-MB-134 | Luminal | Positive | Normal | Resistant |
| MDA-MB-175 | Luminal | Positive | Normal | Resistant |
| MDA-MB-415 | Luminal | Positive | Normal | Resistant |
| ZR-75-1 | Luminal | Positive | Normal | Resistant |
| CAMA-1 | Luminal | Positive | Normal | Resistant |
| BT-474 | Luminal | Positive | Amplified | Moderately Sensitive |
| HCC-1419 | Luminal | Positive | Amplified | Moderately Sensitive |
| MDA-MB-361 | Luminal | Positive | Amplified | Moderately Sensitive |
| EFM-19 | Luminal | Positive | Normal | Moderately Sensitive |
| MCF-7 | Luminal | Positive | Normal | Moderately Sensitive |
| T-47D | Luminal | Positive | Normal | Moderately Sensitive |
| BT-20 | Basal | Negative | Normal | Resistant |
| HCC 38 | Basal | Negative | Normal | Resistant |
| MDA-MB-468 | Basal | Negative | Normal | Resistant |
| HCC-1954 | Basal | Negative | Amplified | Moderately Sensitive |
| HCC-1143 | Basal | Negative | Normal | Moderately Sensitive |
| HCC-1187 | Basal | Negative | Normal | Moderately Sensitive |
| HCC-1937 | Basal | Negative | Normal | Moderately Sensitive |
| HCC-1806 | Basal | Negative | Normal | Highly Sensitive |
| HCC-70 | Basal | Negative | Normal | Highly Sensitive |
| CAL-51 | Post-EMT | Negative | Normal | Highly Sensitive |
| Hs578t | Post-EMT | Negative | Normal | Highly Sensitive |
| MDA-MB-157 | Post-EMT | Negative | Normal | Highly Sensitive |
| MDA-MB-231 | Post-EMT | Negative | Normal | Highly Sensitive |
| MDA-MB-435 | Post-EMT | Negative | Normal | Highly Sensitive |
| MDA-MB-436 | Post-EMT | Negative | Normal | Highly Sensitive |
| HCC-1569 | Post-EMT | Negative | Amplified | Resistant |

Proliferation responses were based on the level of inhibition at 1 µM of dasatinib with those cell lines having greater than 60% inhibition being assigned to the highly sensitive group, those with 40-59% inhibition being assigned to the moderately sensitive group, and those with <40% inhibition at 1 µM assigned to the resistant group. The moderately sensitive and highly sensitive cell lines were grouped as "Sensitive" in the chi-square test and demonstrate a highly significant relationship between sensitivity to dasatinib and the basal subtype of breast cancer cell lines with $\chi^2=9.66$ and P=0.008 (See Table 2).

TABLE 3

|  | Luminal breast cancer | Basal breast Cancer | Post EMT breast cancer | Total |
|---|---|---|---|---|
| Resistant to Dasatinib | 17 | 3 | 1 | 21 |
| Sensitive to Dasatinib | 6 | 6 | 6 | 18 |
| Total | 23 | 9 | 7 | 39 |

Example 7

Figure 2:
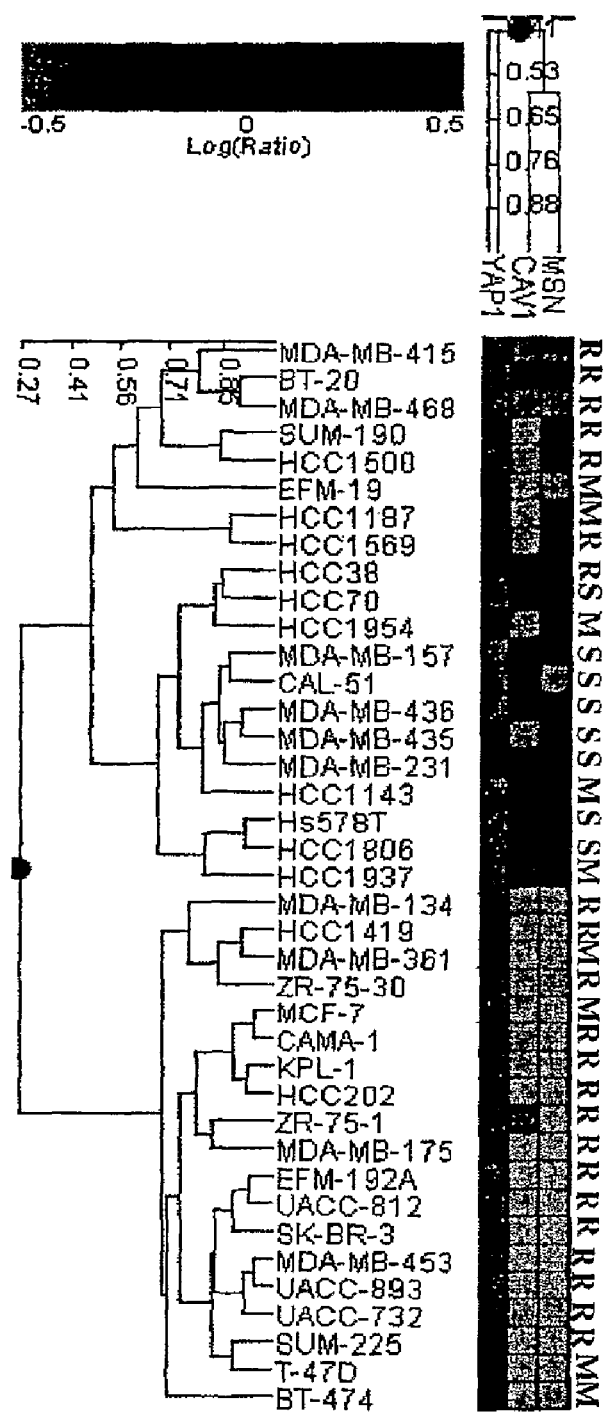
FIG. 2 shows 39 breast cancer cell lines with relative expression of moesin (MSN), caveolin 1 (CAV1), and yes-associated protein-1 (YAP1) based on baseline Agilent expression profiles. Each cell line is assigned a response based on Table 2 (R=resistant, M=moderately sensitive, S=highly sensitive).

Expression of a Three Gene Subset Predicts Response to Dasatinib with a Specificity and Sensitivity of 88 and 86% Respectively Across Subtypes Some luminal cell lines demonstrated moderate sensitivity to dasatinib (Table 2). Data matrices of differentially expressed genes were developed in an attempt to identify potential predictive markers of dasatinib response. Initially genes were sought that differentiated the sensitive basal cell lines from resistant basal and luminal cell lines. This analysis yielded both moesin and caveolin 1 as potential discriminators. Next, using a similar technique, genes were identified that discriminated between the luminal cell lines that were sensitive (moderate) and resistant. Yes associated protein-1 (YAP-1) was identified based on its differential expression between the two groups and potential biologic significance since YAP-1 is a protein with relevance to src signaling. It is a 65 kD protein that binds to the gene product of the src-family kinase yes. The relative expression levels of these three genes in the cell line panel and their associated response to dasatinib in vitro was evident (FIG. 2). Detection of one of these three markers is predictive of an in vitro response to dasatinib with a sensitivity and specificity of 88 and 86% respectively (see Table 4).

TABLE 4

| Gene Expression [Log(ratio)] | Sensitive and moderate response to dasatinib | Resistant response to dasatinib |
|---|---|---|
| Moesin, caveolin 1, or yes-associated protein 1 > 0 P < 0.01 | (True positive) 15 | (False positive) 3 |
| Moesin, caveolin 1, or yes-associated protein 1 < 0 P < 0.01 | (False negative) 2 | (True negative) 19 |
| Total | 17 | 22 |

A large panel of human breast cancer cell lines was molecularly characterized using gene expression profiles in order to identify a subgroup of breast cancers that are more likely to respond to dasatinib treatment. Using such a large panel better encompasses the molecular heterogeneity of clinical breast cancers, including hormonally driven disease, HER2 amplified disease, and "triple-negative" breast cancers. This approach was then used to test the biologic effects of the multi-targeted kinase inhibitor dasatinib. Recent reports describe an additional approach to identify signatures of oncogenic pathways by using DNA microarrays of mammary epithelial cultures transfected with genes of interest, including src (see, e.g., Bild A H, et al., Nature. 2006 Jan. 19; 439(7074):353-7).

While aberrant activation and expression of src has been implicated in breast cancer, its critical role has not been associated with any distinct molecular phenotype. In this study a strong association between in vitro sensitivity to dasatinib and the basal ("triple negative") subtype of human breast cancer was found. Given the large amount of data surrounding the role of src in HER2 signaling, the initial hypothesis was that dasatinib might be most active in cell lines with HER2 amplification, however, most of these cell lines were relatively resistant to monotherapy with dasatinib (11 of 15). In addition, the majority of cell lines that are sensitive are steroid hormone receptor low or negative. These characteristics alone define, in part, the "triple negative" group of breast cancer.

Using the baseline expression arrays, "responsive" cell lines were further discriminated using the differential expression of three genes: moesin, caveolin, and yes-associated protein-1 with a high sensitivity and specificity (88 and 86%, respectively). While other genes can be derived from the analysis of large microarray datasets, the biologic relevance of these genes makes them predictive markers for defining a population of breast cancers that RE likely to respond to a src-targeted therapeutic like dasatinib. Caveolin1 interacts closely with the SFK, fyn, in linking integrins with ras-ERK signaling in the focal adhesion pathway as well as other SFKs (28-29) (see, e.g., Wary K K, et al., Cell. 1998 Sep. 4; 94(5): 625-34 and Williams T M, et al., Am J Cell Physiol. 2005 March; 288(3):C494-C506) and as stated above YAP-1 interacts with src and another SFK proto-oncogene yes, possibly in the tight junction and adherens pathways (see. e.g., Sudol M., Oncogene. 1994 August; 9(8):2145-52 and Playford M P, et al., Oncogene. 2004 Oct. 18; 23(48):7928-46).

c-src (see, e.g., SEQ ID NO: 15) is the cellular homolog of the viral oncogene v-src and is the prototypic member of a family of non-receptor tyrosine kinases that play a key role in many cellular signaling pathways that involve proliferation, differentiation, survival, motility, and angiogenesis. Aberrant expression and activation of src-family kinases (SFKs) have been implicated in a number of human malignancies but thus far they have not proven to be effective clinical targets (see, e.g., Irby R B et al., Oncogene. 2000 Nov. 20; 19(49):5636-42 and Ishizawar R et al., Cancer Cell. 2004 September; 6(3): 209-14). Despite this, molecular studies continue to show src to play a potential role in clinically important pathways in breast cancer including the steroid and peptide hormone signaling pathways (see, e.g., Bromann P A, et al., Oncogene. 2004 Oct. 18; 23(48):7957-68 and Shupnik M A et al., Oncogene. 2004 Oct. 18; 23(48):7979-89).

The src oncogene was the first transforming gene described, however until recently it was not pursued aggressively as a target in oncology. Unlike v-src, the human cellular homologue c-src was found to be only weakly tumorigenic and therefore was not felt to play a large role in the pathogenesis of human malignancies (see, e.g., Ishizawar R et al., Cancer Cell. 2004 September; 6(3):209-14). However, recently, aberrant activation and expression of c-src has been associated with human disease, including malignancies of the lung, skin, colon, ovary, endometrium, head and neck area and breast (see, e.g., Irby R B et al., Oncogene. 2000 Nov. 20; 19(49):5636-42). This has lead to the current hypothesis that c-src may facilitate the action of other signaling proteins, rather than being a dominant transforming agent. On its own, c-src interacts with a number of cellular factors including the cell surface receptors of the EGFR family, CSFR-1, PDGFR, and FGFR as well as integrins, cell-cell adhesion molecules, steroid hormone receptors, components of pathways regulated by G-protein coupled receptors, and focal adhesion kinases (fak), as well as adapter proteins such as shc and many others (see, e.g., Irby R B et al., Oncogene. 2000 Nov. 20; 19(49):5636-42). As a result of its role in these critical pathways c-src is likely to play a key role in the regulation of proliferation, differentiation, survival, motility, angiogenesis, and functions of differentiated cells (see, e.g., Irby R B et al., Oncogene. 2000 Nov. 20; 19(49):5636-42). It is known that alterations in several of these processes are characteristic of the malignant phenotype (see, e.g., Hanahan D, et al., Cell. 2000 Jan. 7; 100(1):57-70). The current data from our group as well as data independently generated by Clark et al. The data indicates some dependence on src signaling pathways in the basal subgroup of breast cancers in vitro (see, e.g., Clark E, et al., Proceedings of the Am Soc Clin Oncol Abstract 3010, 2005). Other recent research has supported the role of src inhibition with dasatinib in head and neck, pancreatic and lung cancer models as well (see, e.g., Johnson F M, et al., Clin Cancer Res. 2005 Oct. 1; 11(19 Pt1):6924-32; Trevino J G, et al., Am J Pathol. 2006 March; 168(3):962-72; and Song L, et al., Cancer Res 66 (11): 5542-8, 2006).

Mutations in the abl kinase (see, e.g., SEQ ID NO: 16) are the defining alteration in chronic myelogenous leukemia and have been the basis for molecular targeting of that disease initially with imatinib and now dasatinib. An alternative explanation for the current results could be based on new data implicating abl in breast cancer. Evaluation of abl activation in a panel of 8 breast cancer cell lines has shown constitutive activation of abl in "aggressive breast cancer cells" without increases in abl gene expression (see, e.g., Srinivasan D, et al., Cancer Res 2006 Jun. 1; 66(11):5648-55). These cell lines included many cell lines that were evaluated in the panel, including MDA-MB-468, MCF-7, BT-474, SK-BR-3, MDA-MB-231, MDA-MB-453, and UACC-893. Interestingly, these authors described significantly increased abl activity in MDA-MB-231 and MDA-MB-435 cells. These cell lines are among those listed as most highly sensitive to dasatinib and are classified as post-EMT due to their expression of high levels of vimentin. Also of interest is the observation that the basal cell line MDA-MB-468 was one of only 3 basal cell lines that we found to be resistant to dasatinib and in the study implicating abl this cell line had a low level of abl activation (see, e.g., Srinivasan D, et al., Cancer Res 2006 Jun. 1; 66(11): 5648-55). Therefore abl inhibition can be another potential mechanism of dasatinib activity in basal breast cancer cell lines.

Using an in vitro pharmocogenomic approach, this unique gene set has been identified that predicts response to dasatinib. The majority of these cell lines, also represent the "triple negative" (ER-, PR-, HER2-) (i.e., lacking, or having a reduced expression of, for example, ER (SEQ ID NO: 7), PR (SEQ ID NO: 8), and HER2 (SEQ ID NO: 9) subset of breast cancers, that currently lack effective treatment. This disclosure provides evidence that this gene set can be used as a predictor of response to dasatinib (as well as other related compounds). Importantly, these data provide scientific rationale for the clinical development of dasatinib in the treatment of women with "triple-negative" breast cancer, a subtype that is categorized as being aggressive and lacking effective treatments (i.e. hormonal manipulation or trastuzumab).

Throughout this application, various publications are referenced (e.g. within parentheses). The disclosures of these publications are hereby incorporated by reference herein in their entireties and for all purposes. Certain methods and materials in this application are analogous to those found in U.S. Pat. Nos. 6,767,541, 6,165,464, 5,772,997, 5,677,171, 5,770,195, 6,399,063, 5,725,856 and 5,720,954, the contents of which are incorporated herein by reference in their entirety and for all purposes.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE 1

TABLE 1A: MCY POLYNUCLEOTIDE SEQUENCES
Moesin (see, e.g. Accession No. NM_002444) (SEQ ID NO: 1)

```
CGACAGGGGCCGCTCTTTCCTGGGTGGGGTTTGTGAAGTCGTGGCCCGTTAGCAGGAAGCCTAACAGT
CGCCCCGACGCTAGTGAGGGACCCAATCTGAGTCCCCGGCCAGCCGAATCCAAGCCGTGTGTACTGCG
TGCTCAGCACTGCCCGACAGTCCTAGCTAAACTTCGCCAACTCCGCTGCCTTTGCCGCCACCATGCCCA
AAACGATCAGTGTGCGTGTGACCACCATGGATGCAGAGCTGGAGTTTGCCATCCAGCCCAACACCACC
GGGAAGCAGCTATTTGACCAGGTGGTGAAAACTATTGGCTTGAGGGAAGTTTGGTTCTTTGGTCTGCA
GTACCAGGACACTAAAGGTTTCTCCACCTGGCTGAAACTCAATAAGAAGGTGACTGCCCAGGATGTGC
GGAAGGAAAGCCCCCTGCTCTTTAAGTTCCGTGCCAAGTTCTACCCTGAGGATGTGTCCGAGGAATTG
ATTCAGGACATCACTCAGCGCCTGTTCTTTCTGCAAGTGAAAGAGGGCATTCTCAATGATGATATTTAC
TGCCCGCCTGAGACCGCTGTGCTGCTGGCCTCGTATGCTGTCCAGTCTAAGTATGGCGACTTCAATAAG
GAAGTGCATAAGTCTGGCTACCTGGCCGGAGACAAGTTGCTCCCGCAGAGAGTCCTGGAACAGCACA
AACTCAACAAGGACCAGTGGGAGGAGCGGATCCAGGTGTGGCATGAGGAACACCGTGGCATGCTCAG
GGAGGATGCTGTCCTGGAATATCTGAAGATTGCTCAAGATCTGGAGATGTATGGTGTGAACTACTTCA
GCATCAAGAACAAGAAAGGCTCAGAGCTGTGGCTGGGGGTGGATGCCCTGGGTCTCAACATCTATGA
GCAGAATGACAGACTAACTCCCAAGATAGGCTTCCCCTGGAGTGAAATCAGGAACATCTCTTTCAATG
ATAAGAAATTTGTCATCAAGCCCATTGACAAAAAAGCCCCGGACTTCGTCTTCTATGCTCCCCGGCTGC
GGATTAACAAGCGGATCTTGGCCTTGTGCATGGGGAACCATGAACTATACATGCGCCGTCGCAAGCCT
GATACCATTGAGGTGCAGCAGATGAAGGCACAGGCCCGGGAGGAGAAGCACCAGAAGCAGATGGAG
CGTGCTATGCTGGAAAATGAGAAGAAGAAGCGTGAAATGGCAGAGAAGGAGAAAGAGAAGATTGAA
CGGGAGAAGGAGGAGCTGATGGAGAGGCTGAAGCAGATCGAGGAACAGACTAAGAAGGCTCAGCAA
GAACTGGAAGAACAGACCCGTAGGGCTCTGGAACTTGAGGAGGAACGGAAGCGTGCCCAGAGCGAGG
```

TABLE 1-continued

```
CTGAAAAGCTGGCCAAGGAGCGTCAAGAAGCTGAAGAGGCCAAGGAGGCCTTGCTGCAGGCCTCCCG
GGACCAGAAAAAGACTCAGGAACAGCTGGCCTTGGAAATGGCAGAGCTGACAGCTCGAATCTCCCAG
CTGGAGATGGCCCGACAGAAGAAGGAGAGTGAGGCTGTGGAGTGGCAGCAGAAGGCCCAGATGGTA
CAGGAAGACTTGGAGAAGACCCGTGCTGAGCTGAAGACTGCCATGAGTACACCTCATGTGGCAGAGC
CTGCTGAGAATGAGCAGGATGAGCAGGATGAGAATGGGGCAGAGGCTAGTGCTGACCTACGGGCTGA
TGCTATGGCCAAGGACCGCAGTGAGGAGGAACGTACCACTGAGGCAGAGAAGAATGAGCGTGTGCAG
AAGCACCTGAAGGCCCTCACTTCGGAGCTGGCCAATGCCAGAGATGAGTCCAAGAAGACTGCCAATG
ACATGATCCATGCTGAGAACATGCGACTGGGCCGAGACAAATACAAGACCCTGCGCCAGATCCGGCA
GGGCAACACCAAGCAGCGCATTGACGAATTTGAGTCTATGTAATGGGCACCCAGCCTCTAGGGACCCC
TCCTCCCTTTTTCCTTGTCCCCACACTCCTACACCTAACTCACCTAACTCATACTGTGCTGGAGCCACTA
ACTAGAGCAGCCCTGGAGTCATGCCAAGCATTTAATGTAGCCATGGGACCAAACCTAGCCCCTTAGCC
CCCACCCACTTCCCTGGGCAAATGAATGGCTCACTATGGTGCCAATGGAACCTCCTTTCTCTTCTCTGT
TCCATTGAATCTGTATGGCTAGAATATCCTACTTCTCCAGCCTAGAGGTACTTTCCACTTGATTTTGCA
AATGCCCTTACACTTACTGTTGTCCTATGGGAGTCAAGTGTGGAGTAGGTTGGAAGCTAGCTCCCCTCC
TCTCCCCTACCACTGTCTTCTTCAGGGTCCTGAGATTTACACGGTTGGAGTGTTATGCGGTCTAGGGAA
TGAGACAGGACCTAGGATATCTTCTCCAGGATGTCAACTGACCTAAAATTTGCCCTCCCATCCCGTTTA
GAGTTATTTAGGCTTTGTAACGATTGGGGGATAAAAAGATGTTCAGTCATTTTTGTTTCTACCTCCCAG
ATCGGATCTGTTGCAAACTCAGCCTCAATAAGCCTTGTCGTTGACTTTAGGGACTCAATTTCTCCCCAG
GGTGGATGGGGAAATGGTGCCTTCAAGACCTTCACCAAACATACTAGAAGGGCATTGGCCATTCTAT
TGTGGCAAGGCTGAGTAGAAGATCCTACCCCAATTCCTTGTAGGAGTATAGGCCGGTCTAAAGTGAGC
TCTATGGGCAGATCTACCCCTTACTTATTATTCCAGATCTGCAGTCACTTCGTGGGATCTGCCCCTCCCT
GCTTCAATACCCAAATCCTCTCCAGCTATAACAGTAGGGATGAGTACCCAAAAGCTCAGCCAGCCCCA
TCAGGACTCTTGTGAAAAGAGAGGATATGTTCACACCTAGCGTCAGTATTTTCCCTGCTAGGGGTTTTA
GGTCTCTTCCCCTCTCAGAGCTACTTGGGCCATAGCTCCTGCTCCACAGCCATCCCAGCCTTGGCATCT
AGAGCTTGATGCCAGTAGGCTCAACTAGGGAGTGAGTGCAAAAGCTGAGTATGGTGAGAGAAGCCT
GTGCCCTGATCCAAGTTTACTCAACCCTCTCAGGTGACCAAAATCCCCTTCTCATCACTCCCCTCCAAA
GAGGTGACTGGGCCCTGCCTCTGTTTGACAAACCTCTAACCCAGGTCTTGACACCAGCTGTTCTGTCCC
TTGGAGCTGTAAACCAGAGAGCTGCTGGGGATTCTGGCCTAGTCCCTTCCACACCCCCACCCCTTGCTC
TCAACCCAGGAGCATCCACCTCCTTCTCTGTCTCATGTGTGCTCTTCTTCTTTCTACAGTATTATGTACT
CTACTGATATCTAAATATTGATTTCTGCCTTCCTTGCTAATGCACCATTAGAAGATATTAGTCTTGGGG
CAGGATGATTTTGGCCTCATTACTTTACCACCCCCACACCTGGAAAGCATATACTATATTACAAAATGA
CATTTTTGCCAAAATTATTAATATAAGAAGCTTTCAGTATTAGTGATGTCATCTGTCACTATAGGTCATA
CAATCCATTCTTAAAGTACTTGTTATTTGTTTTTTATTATTACTGTTTGTCTTCTCCCCAGGGTTCAGTCCT
CAAGGGGCCATCCTGTCCCACCATGCAGTGCCCCTAGCTTAGAGCCTCCCTCAATTCCCCCTGCCCACC
ACCCCCCACTCTGTGCCTGACCTTGAGGAGTCTTGTGTGCATTGCTCTGAATTAGCTCACTTGGTGATA
TGTCCTATATTGGCTAAATTGAAACCTGGAATTGTGGGGCAATCTATTAATAGCTGCCTTAAAGTCAGT
AACTTACCCTTAGGGAGGCTGGGGAAAAGGTTAGATTTTGTATTCAGGGGTTTTTTGTGTACTTTTTG
GGTTTTTTAAAAATTGTTTTTGGAGGGGTTTATGCTCAATCCATGTTCTATTTCAGTGCCAATAAAATTT
AGGAAGACTTCAAAAAAAAAAAA
```

Caveolin 1 (see, e.g. Accession No. NM_001753) (SEQ ID NO: 2)

```
GGGAGAAACGTTCTCACTCGCTCTCTGCTCGCTGCGGGCGCTCCCCGCCCTCTGCTGCCAGAACCTTGG
GGATGTGCCTAGACCCGGCGCAGCACACGTGCGGGCCAACGCGAGCAGAACAAACCTTTGGCGGGC
GGCCAGGAGGCTCCCTCCCAGCCACCGCCCCCCTCGAGCGCCTTTTTTTCCCCCCATACAATACAAGAT
CTTCCTTCCTCAGTTCCCTTAAAGCACAGCCGAGGGAAACCTCCTCACAGTTTTCATCCACGGGC
CAGCATGTCTGGGGGCAAATACGTAGACTCGGAGGGACATCTCTACACCGTTCCCATCCGGGAACAGG
GCAACATCTACAAGCCCAACAACAAGGCCATGGCAGACGAGCTGAGCGAGAAGCAAGTGTACGACGG
GCACACCAAGGAGATCGACCTGGTCAACCGCGACCCTAAACACCTCAACGATGACGTGGTCAAGATT
GACTTTGAAGATGTGATTGCAGAACCAGAAGGGACACACAGTTTTGACGGCATTTGGAAGGCCAGCTT
CACCACCTTCACTGTGACGAAATACTGGTTTTACCGCTTGCTGTCTGCCCTCTTTGGCATCCCGATGGC
ACTCATCTGGGGCATTTACTTCGCCATTCTCTCTTTCCTGCACATCTGGGCAGTTGTACCGCCATTAAG
AGCTTCCTGATTGAGATTCAGTGCATCAGCCGTGTCTATTCCATCTACGTCCACACCGTCTGTGACCCA
CTCTTTGAAGCTGTTGGGAAAATATTCAGCAATGTCCGCATCAACTTGCAGAAAGAAATATAAATGAC
ATTTCAAGGATAGAAGTATACCTGATTTTTTTCCTTTTAATTTTCCTGGTGCCAATTTCAAGTTCCAAG
TTGCTAATACAGCAACAATTTATGAATTGAATTATCTTGGTTGAAAATAAAAGATCACTTTCTCAGTT
TTCATAAGTATTATGTCTCTTCTGAGCTATTTCATCTATTTTTGCAGCTCTGAATTTTTAAAACCCATTT
AAATTTTTTTCCTTACCTTTTTATTTGCATGTGGATCAACCATCGCTTTATTGGCTGAGATATGAACATA
TTGTTGAAAGGTAATTTGAGAGAAATATGAAGAACTGAGGAGGAAAAAAAAAAAAAAGAAAAGAAC
CAACAACCTCAACTGCCTACTCCAAAATGTTGGTCATTTTATGTTAAGGGAAGAATTCCAGGGTATGG
CCATGGAGTGTACAAGTATGTGGGCAGATTTTCAGCAAACTCTTTTCCCACTGTTTAAGGAGTTAGTGG
ATTACTGCCATTCACTTCATAATCCAGTAGGATCCAGTGATCCTTACAAGTTAGAAAACATAATCTTCT
GCCTTCTCATGATCCAACTAATGCCTTACTCTTCTTGAAATTTTAACCTATCTATATTTCTGTGCCTGAA
TATTTGTTATGTAGATAACAAGACCTCAGTGCCTTCCTGTTTTTCACATTTTCCTTTTCAAATAGGGTCT
AACTCAGCAACTCGCTTTAGGTCAGCAGCCTCCCTGAAGACCAAAATTAGAATATCCATGACCTAGTT
TTCCATGCGTGTTTCTGACTCTGAGCTACAGAGTCTGGTGAAGCTCACTTCTGGGCTTCATCTGGCAAC
ATCTTTATCCGTAGTGGGTATGGTTGAGACTAGCCCAATGAAATGAATTAAAGTGGACCAATAGGGCT
GAGCTCTCTGTGGGCTGGCAGTCCTGGAAGCCAGCTTTCCCTGCCTCTCATCAACTGAATGAGGTCAGC
ATGTCTATTCAGCTTCGTTTATTTTCAAGAATAATCACGCTTTCCTGAATCCAAACTAATCCATCACCG
GGGTGGTTTAGTGGCTCAACATTGTGTTCCCATTTCAGCTGATCAGTGGGCCTCCAAGGAGGGGCTGT
AAAATGGAGGCCATTGTGTGAGCCTATCAGAGTTGCTGCAAACCTGACCCCTGCTCAGTAAAGCACTT
GCAACGTCTGTTATGCTGTGACACATGGCCCTCCCCCCTGCCAGGAGCTTTGGACCTAATCCAAGCAT
CCCTTTGCCCAGAAAGAAGATGGGGGAGGAGGCAGTAATAAAAAGATTGAAGTATTTTGCTGGAATA
AGTTCAAATTCTTCTGAACTCAAACTGAGGAATTTCACCTGTAAACCTGAGTCGTACAGAAAGCTGCC
TGGTATATCCAAAGCTTTTTATTCCTCCTGCTCATATTGTGATTCTGCCTTTGGGACTTTTCTTAAAC
CTTCAGTTATGATTTTTTTTCATACACTTATTGGAACTCTGCTTGATTTTTGCCTCTTCCAGTCTTCCTG
ACACTTTAATTACCAACCTGTTACCTACTTTGACTTTTTGCATTTAAAACAGACACTGGCATGGATATA
GTTTTACTTTTTAAACTGTGTACATAAGTGAAAATGTGCTATACTGCATACTTTTTAAATGTAAAGATAT
```

TABLE 1-continued

```
TTTTATCTTTATATGAAGAAAATCACTTAGGAAATGGCTTTGTGATTCAATGTGTAAACTGTGTATTCC
AAGACATGTCTGTTCTACATAGATGCTTAGTCCCTCATGCAAATCAATTACTGGTCCAAAAGATTGCTG
AAATTTTATATGCTTACTGATATATTTTACAATTTTTTATCATGCATGTCCTGTAAAGGTTACAAGCCTG
CACAATAAAAATGTTTAACGGTT
```

Yes-associated Protein 1 (See, e.g. Accession No. NM_006106)
(SEQ ID NO: 3)

```
CCGAGTGCCTCGCAGCCCCTCCCGAGGCGCAGCCGCCAGACCAGTGGAGCCGGGGCGCAGGGCGGGG
GCGGAGGCGCCGGGGCGGGGATGCGGGGCCGCGGCGCAGCCCCCCGGCCCTGAGAGCGAGGACAG
CGCCGCCCGGCCCGCAGCCGTCGCCGCTTCTCCACCTCGGCCCGTGGAGCCGGGGCGTCCGGGCGTAG
CCCTCGCTGGCCTGGGTCAGGGGGTGCGCGTCGGGGGAGGCAGAAGCCATGGATCCCGGGCAGCAGC
CGCCGCCTCAACCGGCCCCCCAGGGCCAAGGGCAGCCGCCTTCGCAGCCCCCGCAGGGGCAGGGCCC
GCCGTCGGGACCCGGGCAACCGGCACCCGCGGCGACCCAGGCGGCCGCAGGCACCCCCGCCGGG
CATCAGATCGTGCACGTCCGCGGGGACTCGGAGACCGACCTGGAGGCGCTCTTCAACGCCGTCATGAA
CCCCAAGACGGCCAACGTGCCCCAGACCGTGCCCATGAGGCTCCGGAAGCTGCCCGACTCCTTCTTCA
AGCCGCCGGAGCCCAAATCCCACTCCCGACAGGCCAGTACTGATGCAGGCACTGCAGGAGCCCTGACT
CCACAGCATGTTCGAGCTCATTCCTCTCCAGCTTCTCTGCAGTTGGGAGCTGTTTCTCCTGGGACACTG
ACCCCCACTGGAGTAGTCTCTGGCCCAGCAGCTACACCCACAGCTCAGCATCTTCGACAGTCTTCTTTT
GAGATACCTGATGATGTACCTCTGCCAGCAGGTTGGGAGATGGCAAAGACATCTTCTGGTCAGAGATA
CTTCTTAAATCATCGATCAGACAACAACATGGCAGGACCCCACAGGAGTTGCATGCTGTCCCAGATGA
ACGTCACAGCCCCCACCAGTCCACCAGTGCAGCAGAATATGATGAACTCGGCTTCAGCCATGAACCAG
AGAATCAGTCAGAGTGCTCCAGTGAAACAGCCACCACCCCTGCCTCCCCAGAGCCCACAGGGAGGCG
TCATGGGTGGCAGCAACTCCAACCAGCAGCAACAGATGCGACTGCAGCAACTGCAGATGGAGAAGGA
GAGGCTGCGGCTGAAACAGCAAGAACTGCTTCGGCAGGTGAGGCCACAGGAGTTAGCCCTGCGTAGC
CAGTTACCAACACTGGAGCAGGATGGTGGGACTCAAAATCCAGTGTCTTCTCCCGGGATGTCTCAGGA
ATTGAGAACAATGACGACCAATAGCTCAGATCCTTTCCTTAACAGTGGCACCTATCACTCTCGAGATG
AGAGTACAGACAGTGGACTAAGCATGAGCAGCTACAGTGTCCCTCGAACCCCAGATGACTTCCTGAAC
AGTGTGGATGAGATGGATACAGGTGATAATCAACCAAAGCACCCTGCCCTCACAGCAGAACCGTTT
CCCAGACTACCTTGAAGCCATTCCTGGGACAAATGTGGACCTTGGAACACTGGAAGGAGATGGAATG
AACATAGAAGGAGAGGAGCTGATGCCAAGTCTGCAGGAAGCTTTGAGTTCTGACATCCTTAATGACAT
GGAGTCTGTTTTGGCTGCCACCAAGCTAGATAAAGAAAGCTTTCTTACATGGTTATAGAGCCCTCAGG
CAGACTGAATTCTAAATCTGTGAAGGATCTAAGGAGACACATGCACCGGAAATTTCCATAAGCCAGTT
GCAGTTTTCAGGCTAATACAGAAAAAGATGAACAAACGTCCAGCAAGATACTTTAATCCTCTATTTTG
CTCTTCCTTGTCCATTGCTGCTGTTAATGTATTGCTGACCTCTTTCACAGTTGGCTCTAAAGAATCAAAA
GAAAAAAACTTTTTATTTCTTTTGCTATTAAAACTACTGTTCATTTTGGGGCTGGGGAAGTGAGCCT
GTTTGGATGATGGATGCCATTCCTTTTGCCCAGTTAAATGTTCACCAATCATTTTAACTAAATACTCAG
ACTTAGAAGTCAGATGCTTCATGTCACAGCATTTAGTTTGTTCAACAGTTGTTTCTTCAGCTTCCTTTGT
CCAGTGGAAAAACATGATTTACTGGTCTGACAAGCCAAAAATGTTATATCTGATATTAAATACTTAAT
GCTGATTTGAAGAGATAGCTGAAACCAAGGCTGAAGACTGTTTTACTTTCAGTATTTTCTTTTCCTCCT
AGTGCTATCATTAGTCACATAATGACCTTGATTTTATTTTAGGAGCTTATAAGGCATGAGACAATTTCC
ATATAAATATATTAATTATTGCCACATACTCTAATATAGATTTTGGTGGATAATTTTGTGGGTGTGCAT
TTTGTTCTGTTTTGTTGGGTTTTTTGTTTTTTTGTTTTTGGCAGGGTCGGTGGGGGGTTGGTTGGTTGG
TTGGTTTTGTCGGAACCTAGGCAAATGACCATATTAGTGAATCTGTTAATAGTTGTAGCTTGGGATGGT
TATTGTAGTTGTTTTGGTAAAATCTTCATTTCCTGGTTTTTTTTACCACCTTATTTAAATCTCGATTATCT
GCTCTCTCTTTTATATACATACACACACCCAAACATAACATTTATAATAGTTGGTAGTGGAATGATTC
CTTTTTTAGGTTTCCCTGCTTTCCAGTTAATTTTTAAAATGGTAGCGCTTTGTATGCATTTAGAATACAT
GACTAGTAGTTTATATTTCACTGGTAGTTTAAATCTGGTTGGGGCAGTCTGCAGATGTTTGAAGTAGTT
TAGTGTTCTAGAAAGAGCTATTACTGTGGATAGTGCCTAGGGGAGTGCTCCACGCCCTCTGGGCATAC
GGTAGATATTATCTGATGAATTGGAAAGGAGCAAACCAGAAATGGCTTTATTTTCTCCCTTGGACTAA
TTTTTAAGTCTCGATTGGAATTCAGTGAGTAGGTTCATAATGTGCATGACAGAAATAAGCTTTATAGTG
GTTTACCTTCATTTAGCTTTGGAAGTTTTCTTTGCCTTAGTTTTGGAAGTAAATTCTAGTTTGTAGTTCT
CATTTGTAATGAACACATTAACGACTAGATTAAAATATTGCCTTCAAGATTGTTCTTACTTACAAGACT
TGCTCCTACTTCTATGCTGAAAATTGACCCTGGATAGAATACTATAAGGTTTTGAGTTAGCTGGAAAAG
TGATCAGATTAATAAATGTATATTGGTAGTTGAATTTAGCAAAGAAATAGAGATAATCATGATTATAC
CTTTATTTTTACAGGAAGAGATGATGTAACTAGAGTATGTGTCTACAGGAGTAATAATGGTTTCCAAA
GAGTATTTTTAAAGGAACAAAACGAGCATGAATTAACTCTTCAATATAAGCTATGAAGTAATAGTTG
GTTGTGAATTAAAGTGGCACCAGCTAGCACCTCTGTGTTTAAGGGTCTTTCAATGTTTCTAGAATAAG
CCCTTATTTTCAAGGGTTCATAACAGGCATAAAATCTCTTCTCCTGGCAAAAGCTGCTATGAAAAGCCT
CAGCTTGGGAAGATAGATTTTTTTCCCCCCAATTACAAAATCTAAGTATTTTGGCCCTTCAATTTGGAG
GAGGGCAAAAGTTGGAAGTAAGAAGTTTTATTTTAAGTACTTTCAGTGCTCAAAAAAATGCAATCACT
GTGTTGTATATAATAGTTCATAGGTTGATCACTCATAATAATTGACTCTAAGGCTTTTATTAAGAAAAC
AGCAGAAAGATTAAATCTTGAATTAAGTCTGGGGGGAAATGGCCACTGCAGATGGAGTTTTAGAGTA
GTAATGAAATTCTACCTAGAATGCAAAATTGGGTATATGAATTACATAGCATGTTGTTGGGATTTTTT
TAATGTGCAGAAGATCAAAGCTACTTGGAAGGAGTGCCTATAATTTGCCAGTAGCCACAGATTAAGAT
TATATCTTATATATCAGCAGATTAGCTTTAGCTTAGGGGAGGGTGGGAAAGTTTGGGGGGGGGGTTG
TGAAGATTTAGGGGGACCTTGATAGAGAACTTTATAAACTTCTTTCTCTTTAATAAAGACTTGTCTTAC
ACCGTGCTGCCATTAAAGGCAGCTGTTCTAGAGTTTCAGTCACCTAAGTACACCCACAAAACAATATG
AATATGGAGATCTTCCTTTACCCCTCAACTTTAATTTGCCAGTTATACCTCAGTGTTGTAGCAGTACT
GTGATACCTGGCACAGTGCTTTGATCTTACGATGCCCTCTGTACTGACCTGAAGGAGACCTAAGAGTC
CTTTCCCTTTTGAGTTTGAATCATAGCCTTGATGTGGTCTCTTGTTTTTATGTCCTTGTTCCTAATGTAAA
AGTGCTTAACTGCTTCTTGGTTGTATTGGGTAGCATTGGGATAAGATTTTAACTGGGTATTCTTGAATT
GCTTTTACAATAAACCAATTTTATAATCTTTAAATTTATCAACTTTTTACATTTGTGTTATTTTCAGTCA
GGGCTTCTTAGATCTACTTATGGTTGATGGAGCACATTGATTTGGAGTTTCAGATCTTCCAAAGCACTA
TTTGTTGTAATAACTTTTCTAAATGTAGTGCCTTTAAAGGAAAAATGAACACAGGGAAGTGACTTTGCT
ACAAATAATGTTGCTGTGTTAAGTATTCATATTAAATACATGCCTTCTATATGGAACATGGCAGAAAG
ACTGAAAAATAACAGTAATTAATTGTGTAATTCAGAATTCATACCAATCAGTGTTGAAACTCAAACAT
TGCAAAAGTGGGTGGCAATATTCAGTGCTTAACACTTTTCTAGCGTTGGTACATCTGAGAAATGAGTG
CTCAGGTGGATTTTATCCTCGCAAGCATGTTGTTATAAGAATTGTGGGTGTGCCTATCATAACAATTGT
TTTCTGTATCTTGAAAAAGTATTCTCCACATTTTAAATGTTTTATATTAGAGAATTCTTTAATGCACACT
```

TABLE 1-continued

```
TGTCAAATATATATATATAGTACCAATGTTACCTTTTTATTTTTTGTTTTAGATGTAAGAGCATGCTCAT
ATGTTAGGTACTTACATAAATTGTTACATTATTTTTTCTTATGTAATACCTTTTTGTTTGTTTATGTGGTT
CAAATATATTCTTTCCTTAAAAAAAAAAAAAAAAAAAAAAAAAAAAAAAAAAAAAAA
```

TABLE 1B: MCY POLYPEPTIDE SEQUENCES
Moesin, see, e.g. Accession No. NP_002435)(SEQ ID NO: 4)

```
MPKTISVRVTTMDAELEFAIQPNTTGKQLFDQVVKTIGLREVWFFGLQYQDTKGFSTWLKLNKKVTAQDV
RKESPLLFKFRAKFYPEDVSEELIQDITQRLFFLQVKEGILNDDIYCPPETAVLLASYAVQSKYGDFNKEVHK
SGYLAGDKLLPQRVLEQHKLNKDQWEERIQVWHEEHRGMLREDAVLEYLKIAQDLEMYGVNYFSIKNKK
GSELWLGVDALGLNIYEQNDRLTPKIGFPWSEIRNISFNDKKFVIKPIDKKAPDFVFYAPRLRINKRILALCM
GNHELYMRRRKPDTIEVQQMKAQAREEKHQKQMERNMLENEKKKREMAEKEKEKIEREKEELMERLKQI
EEQTKKAQQELEEQTRRALELEQERKRAQSEAEKLAKERQEAEEAKEALLQASRDQKKTQEQLALEMAEL
TARISQLEMARQKKESEAVEWQQKAQMVQEDLEKTRAELKTAMSTPHVAEPAENEQDEQDENGAEASAD
LRADAMAKDRSEEERTTEAEKNERVQKHLKALTSELANARDESKKTANDMIHAENMRLGRDKYKTLRQI
RQGNTKQRIDEFESM
```

Caveolin 1 (see, e.g. Accession No. AAH82246) (SEQ ID NO: 5)

```
MSGGKYVDSEGHLYTVPIREQGNIYKPNNKAMADELSEKQVYDAHTKEIDLVNRDPKHLNDDVVKIDFED
VIAEPEGTHSFDGIWKASFTTFTVTKYWFYRLLSALFGIPMALIWGIYFAILSFLHIWAVVPCIKSFLIEIQCIS
RVYSIYVHTVCDPLFEAVGKIFSNVRINLQKEI
```

Yes Associated-protein 1 (see, e.g. Accession No. NP_006097)
(SEQ ID: NO: 6)

```
MDPGQQPPPQPAPQGQGQPPSQPPQGQGPPSGPGQPAPAATQAAPQAPPAGHQIVHVRGDSETDLEALFNA
VMNPKTANVPQTVPMRLRKLPDSFFKPPEPKSHSRQASTDAGTAGALTPQHVRAHSSPASLQLGAVSPGTL
TPTGVVSGPAATPTAQHLRQSSFEIPDDVPLPAGWEMAKTSSGQRYFLNHIDQTTTWQDPRKAMLSQMNV
TAPTSPPVQQNMMNSASAMNQRISQSAPVKQPPPLAPQSPQGGVMGGSNSNQQQQMRLQQLQMEKERLR
LKQQELLRQVRPQELALRSQLPTLEQDGGTQNPVSSPGMSQELRTMTTNSSDPFLNSGTYHSRDESTDSGLS
MSSYSVPRTPDDFLNSVDEMDTGDTINQSTLPSQQNRFPDYLEAIPGTNVDLGTLEGDGMNIEGEELMPSLQ
EALSSDILNDMESVLAATKLDKESFLTWL
```

TABLE 1C: ESTROGEN RECEPTOR POLYNUCLEOTIDE SEQUENCE
(see, e.g., Accession No. NM_000125) (SEQ ID NO: 7)

```
GAGTTGTGCCTGGAGTGATGTTTAAGCCAATGTCAGGGCAAGGCAACAGTCCCTGGCCGTCCTCCAGC
ACCTTTGTAATGCATATGAGCTCGGGAGACCAGTACTTAAAGTTGGAGGCCCGGGAGCCCAGGAGCTG
GCGGAGGGCGTTCGTCCTGGGACTGCACTTGCTCCCGTCGGGTCGCCCGGCTTCACCGGACCCGCAGG
CTCCCGGGGCAGGGCCGGGGCCAGAGCTCGCGTGTCGGCGGGACATGCGCTGCGTCGCGTCTAACCTC
GGGCTGTGCTCTTTTTCCAGGTGGCCCGCCGGTTTCTGAGCCTTCTGCCCTGCGGGGACACGGTCTGCA
CCCTGCCCGCGGCCACGGACCATGACCATGACCCTCCACACCAAAGCATCCGGGATGGCCCTACTGCA
TCAGATCCAAGGGAACGAGCTGGAGCCCTGAACCGTCCGCAGCTCAAGATCCCCCTGGAGCGGCCCC
TGGGCGAGGTGTACCTGGACAGCAGCAAGCCCGCCGTGTACAACTACCCCGAGGGCGCCGCCTACGA
GTTCAACGCCGCGGCCGCCGCCAACGCGCAGGTCTACGGTCAGACGGCCTCCCCTACGGCCCGGGT
CTGAGGCTGCGGCGTTCGGCTCCAACGGCCTGGGGGGTTTCCCCCCACTCAACAGCGTGTCTCCGAGC
CCGCTGATGCTACTGCACCCGCCGCCGCAGCTGTCGCCTTTCCTGCAGCCCCACGGCCAGCAGGTGCC
CTACTACCTGGAGAACGAGCCCAGCGGCTACACGGTGCGCGAGGCCGGCCCGCCGGCATTCTACAGG
CCAAATTCAGATAATCGACGCCAGGGTGGCAGAGAAAGATTGGCAGTACCAATGACAAGGGAAGTA
TGGCTATGGAATCTGCCAAGGAGACTCGCTACTGTGCAGTGTGCAATGACTATGCTTCAGGCTACCAT
TATGGAGTCTGGTCCTGTGAGGGCTGCAAGGCCTTCTTCAAGAGAAGTATTCAAGGACATAACGACTA
TATGTGTCCAGCCACCAACCAGTGCACCATTGATAAAAACAGGAGGAAGAGCTGCCAGGCCTGCCGG
CTCCGCAAATGCTACGAAGTGGGAATGATGAAAGGTGGGATACCAGAAAAGACCGAAGAGGAGGAGA
ATGTTGAAACACAAGCGCCAGAGAGATGATGGGGAGGGCAGGGGTGAAGTGGGGTCTGCTGGAGACA
TGAGAGCTGCCAACCTTTGGCCAAGCCCGCTCATGATCAAACGCTCTAAGAAGAACAGCCTGGCCTTG
TCCCTGACGGCCGACCAGATGGTCAGTGCCTTGTTGGATGCTGAGCCCCCCATACTCTATTCCGAGTAT
GATCCTACCAGACCCTTCAGTGAAGCTTCGATGATGGGCTTACTGACCAACCTGGCAGACAGGGAGCT
GGTTCACATGATCAACTGGGCGAAGAGGGTGCCAGGCTTTGTGGATTTGACCCTCCATGATCAGGTCC
ACCTTCTAGAATGTGCCTGGCTAGAGATCCTGATGATTGGTCTCGTCTGGCGCTCCATGGAGCACCCAG
GGAAGCTACTGTTTGCTCCTAACTTGCTCTTGGACAGGAACCAGGGAAAATGTGTAGAGGGCATGGTG
GAGATCTTCGACATGCTGCTGGCTACATCATGTCGGTTCCGCATGATGAATCTGCAGGGAGAGGAGTT
TGTGTGCCTCAAATCTATTATTTTGCTTAATTCTGGAGTGTACACATTTCTGTCCAGCACCCTGAAGTCT
CTGGAAGAGAAGGACCATATCCACCGAGTCCTGGACAAGATCACAGACACTTTGATCCACCTGATGGC
CAAGGCAGGCCTGACCCTGCAGCAGCAGCACCAGCGGCTGGCCCAGCTCCTCCTCATCCTCTCCCACA
TCAGGCACATGAGTAACAAAGGCATGGAGCATCTGTACAGCATGAAGTGCAAGAACGTGGTGCCCCT
CTATGACCTGCTGCTGGAGATGCTGGACGCCCACCGCCTACACGCCCCACTAGCCGTGGAGGGGCAT
CCGTGGAGGAGACGGACCAAAGCCACTTGGCCACTGCGGGCTCTACTTCATCGCATTCCTTGCAAAAG
TATTACATCACGGGGGAGGCAGAGGGTTTCCCTGCCACGGTCGAGAGCTCCCTGGCTCCCACACGGT
TCAGATAATCCCTGCTGCATTTTACCCTCATCATGCACCACTTTAGCCAAATTCTGTCTCCTGCATACAC
TCCGGCATGCATCCAACACCAATGGCTTCTAGATGAGTGGCCATTCATTTGCTTGCTCAGTTCTTAGT
GGCACATCTTCTGTCTTCTGTTGGGAACAGCCAAAGGGATTCCAAGGCTAAATCTTTGTAACAGCTCTC
TTTCCCCCTTGCTATGTTACTAAGCGTGAGGATTCCCGTAGCTCTTCACAGCTGAACTCAGTCTATGGG
TTGGGGCTCAGATAACTCTGTGCATTTAAGCTACTTGTAGAGACCCAGGCCTGGAGAGTAGACATTTT
GCCTCTGATAAGCACTTTTTAAATGGCTCTAAGAATAAGCCACAGCAAAGAATTTAAAGTGGCTCCTT
TAATTGGTGACTTGGAGAAAGCTAGGTCAAGGGTTTATTATAGCACCCTCTTGTATTCCTATGGCAATG
CATCCTTTTATGAAAGTGGTACACCTTAAAGCTTTTATATGACTGTAGCAGAGTATCTGGTGATTGTCA
ATTCATTCCCCCTATAGGAATACAAGGGGCACACAGGGAAGGCAGATCCCCTAGTTGGCAAGACTATT
TTAACTTGATACACTGCAGATTCAGATGTGCTGAAAGCTCTGCCTCTGGCTTTCCGGTCATGGGTTCCA
GTTAATTCATGCCTCCCATGGACCTATGGAGAGCAGCAAGTTGATCTTAGTTAAGTCTCCCTATATGAG
```

TABLE 1-continued

```
GGATAAGTTCCTGATTTTTGTTTTTATTTTTGTGTTACAAAAGAAAGCCCTCCCTCCCTGAACTTGCAGT
AAGGTCAGCTTCAGGACCTGTTCCAGTGGGCACTGTACTTGGATCTTCCCGGCGTGTGTGTGCCTTACA
CAGGGGGTGAACTGTTCACTGTGGTGATGCATGATGAGGGTAAATGGTAGTTGAAAGGAGCAGGGGCC
CTGGTGTTGCATTTAGCCCTGGGGCATGGAGCTGAACAGTACTTGTGCAGGATTGTTGTGGCTACTAG
AGAACAAGAGGGAAAGTAGGGCAGAAACTGGATACAGTTCTGAGGCACAGCCAGACTTGCTCAGGGT
GGCCCTGCCACAGGCTGCAGCTACCTAGGAACATTCCTTGCAGACCCCGCATTGCCCTTTGGGGGTGC
CCTGGGATCCCTGGGGTAGTCCAGCTCTTCTTCATTTCCCAGCGTGGCCCTGGTTGGAAGAAGCAGCTG
TCACAGCTGCTGTAGACAGCTGTGTTCCTACAATTGGCCCAGCACCCTGGGGGCACGGGAGAAGGGTGG
GGACCGTTGCTGTCACTACTCAGGCTGACTGGGGCCTGGTCAGATTACGTATGCCCTTGGTGGTTTAGA
GATAATCCAAAATCAGGGTTTGGTTTGGGGAAGAAAATCCTCCCCCTTCCTCCCCGGCCCCGTTCCCTA
CCGCCTCCACTCCTGCCAGCTCATTTCCTTCAATTTCCTTTGAACCTATAGGCTAAAAAGAAAGGCTC
ATTCCAGCCACAGGGCAGCCTTCCCTGGGCCTTTGCTTCTCTAGCACAATTATGGGTTACTTCCTTTTTC
TTAACAAAAAAGAATGTTTGATTTCCTCTGGGTGACCTTATTGTCTGTAATTGAAAGCCTATTGAGAGG
TGATGTCTGTGTTAGCCAATGACCCAGGTGAGCTGCTCGGGCTTCTCTTGGTATGTCTTGTTTGGAAAA
GTGGATTTCATTCATTTCTGATTGTCCAGTTAAGTGATCACCAAAGGACTGAGAATCTGGGAGGGCAA
AAAAAAAAAAAAAGTTTTTATGTGCACTTAAATTTGGGGACAATTTTATGTATCTGTGTTAAGGATAT
GTTTAAGAACATAATTCTTTTGTTGCTGTTTGTTTAAGAAGCACCTTAGTTTGTTTAAGAAGCACCTTAT
ATAGTATAATATATATATTTTTTTGAAATTACATTGCTTGTTTATCAGACAATTGAATGTAGTAATTCTGTT
CTGGATTTAATTTGACTGGGTTAACATGCAAAAACCAAGGAAAAATATTTAGTTTTTTTTTTTTTTTTG
TATACTTTTCAAGCTACCTTGTCATGTATACAGTCATTTATGCCTAAAGCCTGGTGATTATTCATTTAAA
TGAAGATCACATTTCATATCAACTTTTGTATCCACAGTAGACAAAATAGCACTAATTCAGATGCCTATT
GTTGGATATTGAATGACAGACAATCTTATGTAGCAAAGATTATGCCTGAAAAGGAAAATTATTCAGGG
CAGCTAATTTTGCTTTTACCAAAATATCAGTAGTAATATTTTTGGACAGTAGCTAATGGGTCAGTGGGT
TCTTTTTAATGTTTATACTTAGATTTTCTTTTAAAAAAATTAAAATAAAACAAAAAAAAATTTCTAGGA
CTAGACGATGTAATACCAGCTAAAGCCAAACAATTATACAGTGGAAGGTTTTACATTATTCATCCAAT
GTGTTTCTATTCATGTTAAGATACTACTACATTTGAAGTGGGCAGAGAACATCAGATGATTGAAATGTT
CGCCCAGGGGTCTCCAGCAACTTTGGAAATCTCTTTGTATTTTTACTTGAAGTGCCACTAATGGACAGC
AGATATTTCTGGCTGATGTTGGTATTGGGTGTAGGAACATGATTTAAAAAAAAAACTCTTGCCTCTGCT
TTCCCCCACTCTGAGGCAAGTTAAAATGTAAAAGATGTGATTTATCTGGGGGGCTCAGGTATGGTGGG
GAAGTGGATTCAGGAATCTGGGGAATGGCAAATATATTAAGAAGAGTATTGAAAGTATTTGGAGGAA
AATGGTTAATTCTGGGTGTGCACCAGGGTTCAGTAGAGTCCACTTCTGCCCTGGAGACCACAAATCAA
CTAGCTCCATTTACAGCCATTTCTAAAATGGCAGCTTCAGTTGTAGAGAAGAAAGAACAACATCAGCA
GTAAAGTCCATGGAATAGCTAGTGGTCTGTGTTTCTTTTCGCCATTGCCTAGCTTGCCGTAATGATTCT
ATAATGCCATCATGCAGCAATTATGAGAGGCTAGGTCATCCAAAGAGAAGACCCTATCAATGTAGGTT
GCAAAATCTAACCCCTAAGGAAGTGCAGTCTTTGATTTGATTTCCCTAGTAACCTTGCAGATATGTTTA
ACCAAGCCATAGCCCATGCCTTTTGAGGGCTGAACAAATAAGGGACTTACTGATAATTTACTTTTGATC
ACATTAAGGTGTTCTCACCTTGAAATCTTATACACTGAAATGGCCATTGATTTAGGCCACTGGCTTAGA
GTACTCCTTCCCCTGCATGACACTGATTACAAATACTTTCCTATTCATACTTTCCAATTATGAGATGGA
CTGTGGGTACTGGGAGTGATCACTAACACCATAGTAATGTCTAATATTCACAGGCAGATCTGCTTGGG
GAAGCTAGTTATGTGAAAGGCAAATAGAGTCATACAGTAGCTCAAAAGAACAACCATAATTCTCTTTGG
TGCAGGTCTTGGGAGCGTGATCTAGATTACACTGCACCATTCCCAAGTTAATCCCCTGAAAACTTACTC
TCAACTGGAGCAAATGAACTTTGGTCCCAAATATCCATCTTTTCAGTAGCGTTAATTATGCTCTGTTTC
CAACTGCATTTCCTTTCCAATTGAATTAAAGTGTGGCCTCGTTTTTAGTCATTTAAAATTGTTTTCTAAG
TAATTGCTGCCTCTATTATGGCACTTCAATTTTGCACTGTCTTTTGAGATTCAAGAAAAATTTCTATTCT
TTTTTTTGCATCCAATTGTGCCTGAACTTTTAAAATATGTAAATGCTGCCATGTTCCAAACCCATCGTCA
GTGTGTGTTTAGAGCTGTGCACCCTAGAAACAACATATTGTCCCATGAGCAGGTGCCTGAGACACA
GACCCCTTTGCATTCACAGAGAGGTCATTGGTTATAGAGACTTGAATTAATAAGTGACATTATGCCAG
TTTCTGTTCTCTCACAGGTGATAAACAATGCTTTTTGTGCACTACATACTCTTCAGTGTAGAGCTCTTGT
TTTATGGGAAAAGGCTCAAATGCCAAATTGTGTTTGATGGATTAATATGCCCTTTTGCCGATGCACTACT
ATTACTGATGTGACTCGGTTTTGTCGCAGCTTTGCTTTGTTTAATGAAACACACTTGTAAACCTCTTTTG
CACTTTGAAAAAGAATCCAGCGGGATGCTCGAGCCACCTGTAAACAATTTTCTCAACCTATTTGATGTTC
AAATAAAGAATTAAACT
```

TABLE 1D. PROGESTERONE RECEPTOR POLYNUCLEOTIDE SEQUENCE *HOMO SAPIENS*
(see, e.g., Accession No. NM_000926) (SEQ ID NO: 8)

```
GGATCCATTTTATAAGCTCAAAGATAATTACTTTTCAGACTAAGAATATTTAGGGTAAAAGTACTGTT
CAACATCTCTACTGAGGATGTTATGATGTAGCACACTGTATAAGCTGGAGCTAAAGGAAACTTTCCTT
AAAGTGCTATTTACTAAAAATTGGAACACATTCCTTAAGACAAATCGAAGTGTGGCACACAACATCCA
AACTTCCATCATAGATACAGAGGTGTTACCATCTCCCACTCCCAAATTTCTTTGTCACGCTGAGGATAC
TCAAGAGGAGCAGGACATGTTGGTCGCAGCAGGAGAAACTTGAAAGCATTCACTTTTATGGAACTCAT
AAGGGAGAGAATCTCTTATTTAGTATCGTCCTTGATACATTTATTATTTTAAAAGATAATGTAGCCAAA
TGTCTTCCTCTGTGTTAAATCTTTACAAAACTGAAATCTTAAAATGGTGACAAAAATTCTACTTCTGAT
AGAATCTATTCATTTTTCCAATTAGATAGGGCATAATTCTTAATTTGCAAAACAAAACGTAATATGCTT
ATGAGGTTCCATCCCAAAGAACCTGCTATTGAGAGTAGCATTCAGAATAACGGGTGGAAATGCCAACT
CCAGAGTTTCAGATCCTACCGGTAATTGGGGTAGGGAGGGGCTTTGGGCGGGGCCTCCCTAGAGGAGG
AGGCGTTGTTAGAAAGCTGTCTGGCCAGTCCACAGCTGTCACTAATCGGGGTAAGCCTTGTTGTATTTG
TGCGTGTGGGTGGCATTCTCAATGAGAACTAGCTTCACTTGTCATTTGAGTGAAATCTACAACCCGAG
GCGGCTAGTGCTCCCGCAGTACTGGGATCTGAGATCTTCGGAGATGACTGTCGCCCGCAGTACGGAGC
CAGCAGAAGTCCGACCCTTCCTGGGAATGGGCTGTACCGAGAGGTCCACTAGCCCCAGGGTTTAGT
GAGGGGGCAGTGGAACTCAGCGAGGGACTGAGAGCTTCACAGCATGCACGAGTTTGATGCCAGAGAA
AAAGTCGGGAGATAAAGGAGCCGCGTGTCACTAAATTGCCGTCGGAGCCGCAGCCACTCAAGTGCCG
GACTTGTGAGTACTCTGCGTCTCCAGTCCTCGGACAGAAGTTGGAGAACTCTCTTGGAGAACTCCCCG
AGTTAGGAGACGAGATCTCCTAACAATTACTACTTTTTCTTGACCTTGCCGTCCCACTTGCCGCTCGCTGGGAC
AAACGACAGCCACAGTTCCCCTGACGACAGGATGGAGGCCAAGGGCAGGAGCTGACCAGCGCCGCCC
TCCCCCCGCCCCGACCCAGGAGGTGGAGATCCCTCCGGTCCAGCCACATTCAACACCCACTTTCTCCTC
CCTCTGCCCCTATATTCCCGAAACCCCCTCCTCCTTCCCTTTTCCCTCCTCCTGGAGACGGGGGAGGAG
AAAAGGGGAGTCCAGTCGTCATGACTGAGCTGAAGGCAAAGGGTCCCCGGGCTCCCCACGTGGCGGG
CGGCCCGCCCTCCCCCGAGGTCGGATCCCCACTGCTGTGTCGCCCAGCCGCAGGTCCGTTCCCGGGGA
```

TABLE 1-continued

```
GCCAGACCTCGGACACCTTGCCTGCCTGTTTCGGCCATACCTATCTCCCTGGACGGGCTACTCTTCCCTC
GGCCCTGCCAGGGACAGGACCCCTCCGACGAAAAGACGCAGGACCAGCAGTCGCTGTCGGACGTGGA
GGGCGCATATTCCAGAGCTGAAGCTACAAGGGGTGCTGGAGGCAGCAGTTCTAGTCCCCCAGAAAAG
GACAGCGGACTGCTGGACAGTGTCTTGGAGACTCTGTTGGCGCCCTCAGGTCCCGGGCAGAGCCAACC
CAGCCCTCCCGCCTGCGAGGTCACCAGCTCTTGGTGCCTGTTTGGCCCCGAACTTCCCGAAGATCCACC
GGCTGCCCCGCCACCCAGCGGGTGTTGTCCCCGCTCATGAGCCGGTCCGGGTGCAAGGTTGGAGACA
GCTCCGGGACGGGAGCTGCCCATAAAGTGCTGCCCCGGGGCCTGTCACCAGCCCGGCAGCTGCTGCTC
CCGGCCTCTGAGAGCCCTCACTGGTCCGGGGCCCAGTGAAGCCGTCTCCGCAGGCCGCTGCGGTGGA
GGTTGAGGAGGAGGATGGCTCTGAGTCCGAGGAGTCTGCGGGTCCGCTTCTGAAGGGCAAACCTCGG
GCTCTGGGTGGCGCGGCGGCTGGAGGAGGAGCCGCGGCTGTCCCGCCGGGGGCGGCAGCAGGAGGCG
TCGCCCTGGTCCCCAAGGAAGATTCCCGCTTCTCAGCGCCCAGGGTCGCCCTGGTGGAGCAGGACGCG
CCGATGGCGCCCGGGCGCTCCCCGCTGGCCACCACGGTGATGGATTTCATCCACGTGCCTATCCTGCCT
CTCAATGACGCCTTATTGGCAGCGCGCACTCGGCAGCTGCTGGAAGACGAAAGTTACGACGGCGGGGC
CGGGGCTGCCAGCGCCTTTGCCCCGCCGCGGAGTTCACCCTGTGCCTCGTCACCCCGGTCGCTGTAGG
CGACTTCCCCGACTGCGCGTACCCGCCCGACGCCGAGCCCAAGGACGACGCGTACCCTCTCTATAGCG
ACTTCCAGCCGCCCGCTCTAAAGATAAAGGAGGAGGAGGAAGGCGCGGAGGCCTCCGCGCGCTCCCC
GCGTTCCTACCTTGTGGCCGGTGCCAACCCCGCAGCCTTCCCGGATTTCCCGTTGGGGCCACCGCCCC
GCTGCCGCCGCGAGCGACCCCATCCAGACCCGGGGAAGCGGCGGTGACGGCCGCACCCGCCAGTGCC
TCAGTCTCGTCTGCGTCCTCCTCGGGGTCGACCCTGGAGTGCATCCTGTACAAAGCGGAGGGCGCGCC
GCCCCAGCAGGGCCCGTTCGCGCCGCCGCCCTGCAAGGCGCCGGGCGCGAGCGGCTGCCTGCTCCCGC
GGGACGGCCTGCCCTCCACCTCCGCCTCTGCCGCCGCCGCCGGGGCGGCCCCCGCGCTCTACCCTGCA
CTCGGCCTCAACGGGCTCCCGCAGCTCGGCTACGAGGCCGCCGTGCTCAAGGAGGGCCTGCCGCAGGT
CTACCCGCCCTATCTCAACTACCTGAGGCCGGATTCAGAAGCCAGCCAGAGCCCACAATACAGCTTCG
AGTCATTACCTCAGAAGATTTGTTTAATCTGTGGGGATGAAGCATCAGGCTGTCATTATGGTGTCCTTA
CCTGTGGGAGCTGTAAGGTCTTCTTTAAGAGGGCAATGGAAGGGCAGCACAACTACTTATGTGCTGGA
AGAAATGACTGCATCGTTGATAAAAATCCGCAGAAAAAACTGCCCAGCATGTCGCCTTAGAAAGTGCTG
TCAGGCTGGCATGGTCCTTGGAGGTCGAAAATTTAAAAAGTTCAATAAAGTCAGAGTTGTGAGAGCAC
TGGATGCTGTTGCTCTCCCACAGCCAGTGGGCGTTCCAAATGAAAGCCAAGCCCTAAGCCAGAGATTC
ACTTTTTCACCAGGTCAAGACATACAGTTGATTCCACCACTGATCAACCTGTTAATGACATTGAACCA
GATGTGATCTATGCAGGACATGACAACACAAAACCTGACACCTCCAGTTCTTTGCTGACAAGTCTTAA
TCAACTAGGCGAGAGGCAACTTCTTTCAGTAGTCAAGTGGTCTAAATCATTGCCAGGTTTTCGAAACTT
ACATATTGATGACCAGATAACTCTCATTCAGTATTCTTGGATGAGCTTAATGGTGTTTGGTCTAGGATG
GAGATCCTACAAACACGTCAGTGGGCAGATGCTGTATTTTGCCATTGCCTGATCTAATACTAAATGAACAGC
GGATGAAAGAATCATCATTCTATTCATTATGCCTTACCATGTGGCAGATCCCACAGGAGTTTGTCAAGC
TTCAAGTTAGCAAGAAGAGTTCCTCTGTATGAAAGTATTGTTACTTCTTAATACAATTCCTTTGGAAG
GGCTACGAAGTCAAACCCAGTTTGAGGAGATGAGGTCAAGCTACATTAGAGAGCTCATCAAGGCAAT
TGGTTTGAGGCAAAAAGGAGTTGTGTCGAGCTCACAGCGTTTCTATCAACTTACAAAACTTCTTGATA
ACTTGCATGATCTTGTCAAACAACTTCATCTGTACTGCTTGAATACATTTATCCAGTCCCGGGCACTGA
GTGTTGAATTTCCAGAAATGATGTCTGAAGTTATTGCTGCACAATTACCCAAGATATTGGCAGGGATG
GTGAAACCCCTTCTCTTTCATAAAAAGTGAATGTCATCTTTTTCTTTTAAAGAATTAAATTTTGTGGTAT
GTCTTTTTGTTTTGGTCAGGATTATGAGGTCTTGAGTTTTTATAATGTTCTTCTGAAAGCCTTACATTTA
TAACATCATAGTGTGTAAATTTAAAAGAAAAATTGTGAGGTTCTAATTATTTTCTTTTATAAAGTATAA
TTAGAATGTTTAACTGTTTTGTTTACCCATATTTTCTTGAAGAATTTACAAGATTGAAAAAGTACTAAA
ATTGTTAAAGTAAACTATCTTATCCATATTTATTTCATACCATGTAGGTGAGGATTTTTAACTTTTGCATC
TAACAAATCATCGACTTAAGAGAAAAAATCTTACATGTAATAACACAAAGCTATTATATGTTATTTCT
AGGTAACTCCCTTTGTGTCAATTATATTTCCAAAAATGAACCTTTAAAATGGTATGCAAATTTTTGTCT
ATATATATTTGTGTGAGGAGGAAATTCATAACTTTCCTCAGATTTTCAAAAGTATTTTTAATGCAAAAA
ATGTAGAAAGAGTTTAAAACCACTAAAATAGATTGATGTTCTTCAAACTAGGCAAAACAACTCATATG
TTAAGACCATTTCCAGATTGGAAACACAAATCTCTTAGGAAGTTAATAAGTAGATTCATATCATTATG
CAAATAGTATTGTGGGTTTTGTAGGTTTTTAAAATAACCTTTTTTGGGGAGAGAATTGTCCTCTAATGA
GGTATTGCGAGTGG
```

TABLE 1E: HER2 POLYNUCLEOTIDE SEQUENCE *HOMO SAPIENS*
(see, e.g., Accession No. NM_004448) (SEQ ID NO: 9)

```
GGAGGAGGTGGAGGAGGAGGGCTGCTTGAGGAAGTATAAGAATGAAGTTGTGAAGCTGAGATTCCCC
TCCATTGGGACCGGAGAAACCAGGGGAGCCCCCCGGGCAGCCGCGCGCCCCTTCCCACGGGCCCTTT
ACTGCGCCGCGCGCCCGGCCCCCACCCCTCGCAGCACCCCGCGCCCCGCGCCCTCCCAGCCGGGTCCA
GCCGGAGCCATGGGGCCGGAGCCGCAGTGAGCACCATGGAGCTGGCGGCCTTGTGCCGCTGGGGGCT
CCTCCTCGCCCTCTTGCCCCCGGAGCCGCGAGCACCCAAGTGTGCACCGGCACAGACATGAAGCTGC
GGCTCCCTGCCAGTCCCGAGACCCACCTGGACATGCTCCGCCACCTCTACCAGGGCTGCCAGGTGGTG
CAGGGAAACCTGGAACTCACCTACCTGCCCACCAATGCCAGCCTGTCCTTCCTGCAGGATATCCAGGA
GGTGCAGGGCTACGTGCTCATCGCTCACAACCAAGTGAGGCAGGTCCCACTGCAGAGGCTGCGGATTG
TGCGAGGCACCCAGCTCTTTGAGGACAACTATGCCCTGGCCGTGCTAGACAATGGAGACCCGCTGAAC
AATACCACCCCTGTCACAGGGGCCTCCCCAGGAGGCCTGCGGGAGCTGCAGCTTCGAAGCCTCACAGA
GATCTTGAAAGGAGGGGTCTTGATCCAGCGGAACCCCCAGCTCTGCTACCAGGACACGATTTTGTGGA
AGGACATCTTCCACAAGAACAACCAGCTGGCTCTCACACTGATAGACACCAACCGCTCTCGGGCCTGC
CACCCCTGTTCTCCGATGTGTAAGGGCTCCCGCTGCTGGGGAGAGAGTTCTGAGGATTGTCAGAGCCT
GACGCGCACTGTCTGTGCCGGTGGCTGTGCCCGCTGCAAGGGGCCACTGCCCACTGACTGCTGCCATG
AGCAGTGTGCTGCCGGCTGCACGGGCCCCAAGCACTCTGACTGCCTGGCCTGCCTCCACTTCAACCAC
AGTGGCATCTGTGAGCTGCACTGCCCAGCCCTGGTCACCTACAACACAGACACGTTTGAGTCCATGCC
CAATCCCGAGGGCCGGTATACATTCGGCGCCAGCTGTGTGACTGCCTGTCCCTACAACTACCTTTCTAC
GGACGTGGATCCTGCACCCTCGTCTGCCCCCTGCACAACCAAGAGGGTGACAGCAGAGGATGGAACA
CAGCGGTGTGAGAAGTGCAGCAAGCCCTGTGCCCGAGTGTGCTATGGTCTGGGCATGGAGCACTTGCG
AGAGGTGAGGGCAGTTACCAGTGCCAATATCCAGGAGTTTGCTGGCTGCAAGAAGATCTTTGGGAGCC
TGGCATTTCTGCCGGAGAGCTTTGATGGGGACCCAGCCTCCAACACTGCCCCGCTCCAGCCAGAGCAG
CTCCAAGTGTTTGAGACTCTGGAAGAGATCACAGGTTACCTATACATCTCAGCATGGCCGGACAGCCT
GCCTGACCTCAGCGTCTTCCAGAACCTGCAAGTAATCCGGGGACGAATTCTGCACAATGGCGCCTACT
CGCTGACCCTGCAAGGGCTGGGCATCAGCTGGCTGGGGCTGCGCTCACTGAGGGAACTGGGCAGTGG
ACTGGCCCTCATCCACCATAACACCCACCTCTGCTTCGTGCACACGGTGCCCTGGGACCAGCTCTTTCG
```

TABLE 1-continued

```
GAACCCGCACCAAGCTCTGCTCCACACTGCCAACCGGCCAGAGGACGAGTGTGTGGGCGAGGGCCTG
GCCTG CCACCAGCTG TGCGCCCGAG GGCACTGCTGGGGTCCAGGGCCCACCCAGTGTGTCAAC
TGCAGCCAGTTGCTTCGGGGCCAGGAGTGCGTGGAGGAATGCCGAGTACTGCAGGGGCTCCCCAGGG
AGTATGTGAATGCCAGGCACTGTTTGCCGTGCCACCCTGAGTGTCAGCCCCAGAATGCTCAGTGACC
TGTTTTGGACCGGAGGCTGACCAGTGTGTGGCCTGTGCCCACTATAAGGACCCTCCCTTCTGCGTGGCC
CGCTGCCCCAGCGGTGTGAAACCTGACCTCTCCTACATGCCCATCTGGAAGTTTCCAGATGAGGAGGG
CGCATGCGAGCGTTGCCCCATCAACTGCACCCACTCCTGTGTGGACCTGGATGACAAGGGCTGCCCCG
CCGAGCAGAGAGCCAGCCCTCTGACGTCCATCATCTCTGCGGTGGTTGGCATTCTGCTGGTCGTGGTCT
TGGGGGTGGTCTTTGGGATCCTCATCAAGCGACGGCAGCAGAAGATCCGGAAGTACACGATGCGGAG
ACTGCTGCAGGAAACGGAGCTGGTGGAGCCGCTGACACCTAGCGGAGCGATGCCCAACCAGGCGCAG
ATGCGGATCCTGAAAGAGACGGAGCTGAGGAAGGTGAAGGTGCTTGGATCTGGCGCTTTTGGCACAG
TCTACAAGGGCATCTGGATCCCTGATGGGAGAATGTGAAAATTCCAGTGGCCATCAAAGTGTTGAGG
GAAAACACATCCCCAAAGCCAACAAAGAAATCTTAGACGAAGCATACGTGATGGCTGGTGTGGGCT
CCCCATATGTCTCCCGCCTTCTGGGCATCTGCCTGACATCCACGGTGCAGCTGGTGACACAGCTTATGC
CCTATGGCTGCCTCTTAGACCATGTCCGGGAAAACCGCGGACGCCTGGGCTCCCAGGACCTGCTGAAC
TGGTGTATGCAGATTGCCAAGGGGATGAGCTACCTGGAGGATGTGCCGGCTCGTACACAGGGACTTGGC
CGCTCGGAACGTGCTGGTCAAGAGTCCCAACCATGTCAAAATTACAGACTTCGGGCTGGCTCGGCTGC
TGGACATTGACGAGACAGAGTACCATGCAGATGGGGGCAAGGTGCCCATCAAGTGGATGGCGCTGGA
GTCCATTCTCCGCCGGCGGTTCACCCACCAGAGTGATGTGTGGAGTTATGGTGTGACTGTGTGGGAGC
TGATGACTTTTGGGGCAAAACCTTACGATGGGATCCCAGCCCGGGAGATCCCTGACCTGCTGGAAAAG
GGGGAGCGGCTGCCCCAGCCCCCCATCTGCACCATTGATGTCTACATGATCATGGTCAAATGTTGGAT
GATTGACTCTCAATGTCGGCCAAGATTGCGGGAGTTGGTGTCTGAATTCTCCCGCATGGCCAGGGACC
CCCAGCGCTTTGTGGTCATCCAGAATGAGGACTTGGGCCCAGCCAGTCCCTTGGACAGCACCTTCTAC
CGCTCACTGCTGGAGGACGATGACATGGGGGACCTGGTGGATGCTGAGGAGTATCTGGTACCCCAGCA
GGGCTTCTTCTGTCCAGACCCTGCCCCGGGCGCTGGGGGCATGGTCCACCACAGGCACCGCAGCTCAT
CTACCAGGAGTGGCGGTGGGGACCTGACACTAGGGCTGGAGCCCTCTGAAGAGGAGGCCCCCAGGTC
TCCACTGGCACCCTCCGAAGGGGCTGGCTCCGATGTATTTGATGGTGACCTGGGAATGGGGGCAGCCA
AGGGGCTGCAAAGCCTCCCCACACATGACCCCAGCCCTCTACAGCGGTACAGTGAGGACCCCACAGTA
CCCCTGCCCTCTGAGACTGATGGCTACGTTGCCCCCCTGACCTGCAGCCCCCAGCCTGAATATGTGAAC
CAGCCAGATGTTCGGCCCCAGCCCCCTTCGCCCCGAGAGGGCCCTCTGCCCTGCTGCCCGACCTGCTGGT
GCCACTCTGGAAAGGCCCAAGACTCTCTCCCCAGGGAAGAATGGGGTCGTCAAAGACGTTTTTGCCTT
TGGGGGTGCCGTGGAGAACCCCGAGTACTTGACACCCCAGGGAGGAGCTGCCCCTCAGCCCCACCCTC
CTCCTGCCTTCAGCCCAGCCTTCGACAACCTCTATTACTGGGACCAGGACCCACCAGAGCGGGGGGCT
CCACCCAGCACCTTCAAAGGGACACCTACGGCAGAGAACCCAGAGTACCTGGGTCTGGACGTGCCCAG
TGTGAACCAGAAGGCCAAGTCCGCAGAAGCCCTGATGTGTCCTCAGGGAGCAGGGAAGGCCTGACTT
CTGCTGGCATCAGAGGTGGGAGGGCCCTCCGACCACTTCCAGGGGAACCTGCCATGCCAGGAACCTG
TCCTAAGGAACCTTCCTTCCTGCTTGAGTTCCCAGATGGCTGGAAGGGGTCCAGCCTCGTTGGAAGAG
GAACAGCACTGGGGAGTCTTTGTGGATTCTGAGGCCCTGCCCAATGAGACTCTAGGGTCCAGTGGATG
CCACAGCCCAGCTTGGCCCTTTCCTTCCAGATCCTGGGTACTGAAAGCCTTAGGGAAGCTGGCCTGAG
AGGGGAAGCGGCCCTAAGGGAGTGTCTAAGAACAAAAGCGACCCATTCAGAGACTGTCCCTGAAACC
TAGTACTGCCCCCCATGAGGAAGGAACAGCAATGGTGTCAGTATCCAGGCTTTGTACAGAGTGCTTTT
CTGTTTAGTTTTTACTTTTTTTGTTTTGTTTTTTAAAGATGAAATAAAGACCCAGGGGGAGAATGGGT
GTTGTATGGGGAGGCAAGTGTGGGGGGTCCTTCTCCACACCCACTTTGTCCATTTGCAAATATATTTTG
GAAAACAGCTA
```

TABLE 1F VIMENTIN POLYNUCLEOTIDE SEQUENCE *HOMO SAPIENS*
(see, e.g., Accession No. NM_003380) (SEQ ID NO: 10)

```
GTCCCCGCGCCAGAGACGCAGCCGCGCTCCCACCACCCACACCCACCGCGCCCTCGTTCGCCTCTTCTC
CGGGGAGCCAGTCCGCGCCACCGCCGCCGCCCAGGCCATCGCCACCCTCCGCAGCCATGTCCACCAGGT
CCGTGTGGTCGTCCTCCTACCGCAGGATGTTCGGCGGCCCGGGCACCGCGAGCCGGCCGAGCTCCAGC
CGGAGCTACGTGACTACGTCCACCCGCACCTACAGCCTGGGCAGCGCGCTGCGCCCCAGCACCAGCCG
CAGCCTCTACGCCTCGTCCCCGGCGGCGTGTATGCCACGCGCTCCTCTGCCGTGCGCCTGCGGAGCA
GCGTGCCCGGGGTGCGGCTCCTGCAGGACTCGGTGGACTTCTCGCTGGCCGACGCCATCAACACCGAG
TTCAAGAACACCCGCACCAACGAGAAGGTGGAGCTGCAGGAGCTGAATGACCGCTTCGCCAACTACA
TCGACAAGGTGCGCTTCCTGGAGCAGCAGAATAAGATCCTGCTGGCCGAGCTCGAGCAGCTCAAGGG
CCAAGGCAAGTCGCGCCTGGGGGACCTCTACGAGGAGGAGATGCGGGAGCTCTCGCCGGCAGGTGGAC
CAGCTAACCAACGACAAAGCGCGCGTCGAGGTGGAGCGCGACAACCTGGCCGAGGACATCATGCGCC
TCCGGGAGAAATTGCAGGAGGAGATGCTTCAGAGAGAGGAAGCCGAAAACACCCTGCAATCTTTCAG
ACAGGATGTTGACAATGCGTCTCTGGCACGTCTTGACCTTGAACGCAAAGTGGAATCTTTGCAAGAAG
AGATTGCCTTTTTGAAGAAACTCCACGAAGAGGAAATCCAGGAGCTGCAGGCTCAGATTCAGGAACA
GCATGTCCAAATCGATGTGGATGTTTCCAAGCCTGACCTCACGGCTGCCCTGCGTGACGTACGTCAGC
AATATGAAAGTGTGGCTGCCAAGAACCTGCAGGAGGCAGAAGAATGGTACAAATCCAAGTTTGCTGA
CCTCTCTGAGGCTGCCAACCGGAACAATGACGCCCTGCGCCAGGCAAAGCAGGAGTCCACTGAGTACC
GGAGACAGGTGCAGTCCCTCACCTGTGAAGTGGATGCCCTTAAAGGAACCAATGAGTCCCTGGAACGC
CAGATGCGTGAAATGGAAGAGAACTTTGCCGTTGAAGCTGCTAACTACCAAGACACTATTGGCCGCCT
GCAGGATGAGATTCAGAATATGAAGGAGGAAATGGCTCGTCACCTTCGTGAATACCAAGACCTGCTCA
ATGTTAAGATGGCCCTTGACATTGAGATTGCCACCTACAGGAAGCTGCTGGAAGGCGAGGAGAGCAG
GATTTCTCTGCCTCTTCCAAACTTTTCCTCCCTGAACCTGAGGGAAACTAATCTGGATTCACTCCCTCTG
GTTGATACCCACTCAAAAAGGACACTTCTGATTAAGCAGTTGAACATAGAGATGGACAGGTTATCAA
CGAAACTTCTCAGCATCACGATGACCTTGAATAAAAATTGCACACACTCAGTGCAGCAATATATTACC
AGCAAGAATAAAAAGAAATCCATATCTTAAAGAAACAGCTTTCAAGTGCCTTTCTGCAGTTTTTCAG
GAGCGCAAGATAGATTTGGAATAGGAATAAGCTCTAGTTCTTAACAACCGACACTCCTACAAGATTTA
GAAAAAGTTTACAACATAATCTAGTTTACAGAAAAATCTTGTGCTAGAATACTTTTTAAAAGGTATTT
TGAATACCATTAAAACTGCTTTTTTTTTTCCAGCAAGTATCCAACCAACTTGGTCTGCTTCAATAAATC
TTTGGAAAAACTC
```

TABLE 1-continued

TABLE 1G: CYTOKERATIN 5 POLYNUCLEOTIDE SEQUENCE HOMO SAPIENS
(see, e.g., Accession No. NM_000424)(SEQ ID NO: 11)

TCGACAGCTCTCTCGCCCAGCCCAGTTCTGGAAGGGATAAAAGGGGGCATCACCGTTCCTGGGTAAC
AGAGCCACCTTCTGCGTCCTGCTGAGCTCTGTTCTCTCCAGCACCTCCCAACCCACTAGTGCCTGGTTC
TCTTGCTCCACCAGGAACAAGCCACCATGTCTCGCCAGTCAAGTGTGTCCTTCCGGAGCGGGGGCAGT
CGTAGCTTCAGCACCGCCTCTGCCATCACCCCGTCTGTCTCCCGCACCAGCTTCACCTCCGTGTCCCGG
TCCGGGGGTGGCGGTGGTGGTGGCTTCGGCAGGGTCAGCCTTGCGGGTGCTTGTGGAGTGGGTGGCTA
TGGCAGCCGGAGCCTCTACAACCTGGGGGGCTCCAAGAGGATATCCATCAGCACTAGAGGAGGCAGC
TTCAGGAACCGGTTTGGTGCTGGTGCTGGAGGCGGCTATGGCTTTGGAGGTGGTGCCGGTAGTGGATT
TGGTTTCGGCGGTGGAGCTGGTGGTGGCTTTGGGCTCGGTGGCGGAGCTGGCTTTGGAGGTGGCTTCG
GTGGCCCTGGCTTTCCTGTCTGCCCTCCTGGAGGTATCCAAGAGGTCACTGTCAACCAGAGTCTCCTGA
CTCCCCTCAACCTGCAAATCGACCCCAGCATCCAGAGGGTGAGGACCGAGGAGCCAGAGCAGATCAA
GACCCTCAACAATAAGTTTGCCTCCTTCATCGACAAGGTGCGGTTCCTGGAGCAGCAGAACAAGGTTC
TGGACACCAAGTGGACCCTGCTGCAGGAGCAGGGCACCAAGACTGTGAGGCAGAACCTGGAGCCGTT
GTTCGAGCAGTACATCAACAACCTCAGGAGGCAGCTGGACAGCATCGTGGGGGAACGGGGCCGCCTG
GACTCAGAGCTGAGAAACATGCAGGACCTGGTGGAAGACTTCAAGAACAAGTATGAGGAGATCAA
ACAAGCGTACCACTGCTGAGAATGAGTTTGTGATGCTGAAGAAGGATGTAGATGCTGCCTACATGAAC
AAGGTGGAGCTGGAGGCCAAGGTTGATGCACTGATGGATGAGATTAACTTCATGAAGATGTTCTTTGA
TGCGGAGCTGTCCCAGATGCAGACGCATGTCTCTGACACCTCAGTGGTCCTCTCCATGGACAACAACC
GCAACCTGGACCTGGATAGCATCATCGCTGAGGTCAAGGCCCAGTATGAGGAGATTGCCAACCGCAG
CCGGACAGAAGCCGAGTCCTGGTATCAGACCAAGTATGAGGAGCTGCAGCAGACAGCTGGCCGGCAT
GGCGATGACCTCCGCAACACCAAGCATGAGATCACAGAGATGAACCGGATGATCCAGAGGCTGAGAG
CCGAGATTGACAATGTCAAGAAACAGTGCGCCAATCTGCAGAACGCCATTGCGGATGCCGAGCAGCG
TGGGGAGCTGGCCCTCAAGGATGCCAGGAACAAGCTGGCCGAGCTGGAGGAGGCCCTGCAGAAGGCC
AAGCAGGACATGGCCCGGCTGCTGCGTGAGTACCAGGAGCTCATGAACACCAAGCTGGCCCTGGACG
TGGAGATCGCCACTTACCGCAAGCTGCTGGAGGGCGAGGAATGCAGACTCAGTGGAGAAGGAGTTGG
ACCAGTCAACATCTCTGTTGTCACAAGCAGTGTTTCCTCTGGATATGGCAGTGGCAGTGGCTATGGCG
GTGGCCTCGGTGGAGGTCTTGGCGGCGGCCTCGGTGGAGGTAGCAGTGGAAGCTAC
TACTCCAGCAGCAGTGGGGGTGTCGGCCTAGGTGGTGGGCTCAGTGTGGGGGGCTCTGGCTTCAGTGC
AAGCAGTGGCCGAGGGCTGGGGGTGGGCTTTGGCAGTGGCGGGGGTAGCAGCTCCAGCGTCAAATTT
GTCTCCACCACCTCCTCCTCCCGGAAGAGCTTCAAGAGCTAAGAACCTGCTGCAAGTCACTGCCTTCCA
AGTGCAGCAACCAGCCCATGGAGATTGCCTCTTCTAGGCAGTTGCCTGTCCAAGCCATGTTTTATCCTTTC
TGGAGAGTAGTCTAGACCAAGCCAATTGCAGAACCACATTCTTTGGTTCCCAGGAGAGCCCCATTCCC
AGCCCCTGGTCTCCCGTGCCGCAGTTCTATATTCTGCTTCAAATCAGCCTTCAGGTTTCCCACAGCATG
GCCCCTGCTGACACGAGAACCCAAAGTTTTCCCAAATCTAAATCATCAAAACAGAATCCCCACCCCAA
TCCCAAATTTTGTTTTGGTTCTAACTACCTCCAGAATGTGTTCAATAAAATGCTTTTATAATAT

TABLE 1H: CYTOKERATIN 17 POLYNUCLEOTIDE SEQUENCE HOMO SAPIENS
(see, e.g., Accession No. NM_000422)(SEQ ID NO: 12)

CTCCTCTCCAGCCCTTCTCCTGTGTGCCTGCCTCCTGCCGCCGCCACCATGACCACCTCCATCCGCCAGT
TCACCTCCTCCAGCTCCATCAAGGGCTCCTCCGGCCTGGGGGGCGGCTCGTCCCGCACCTCGTGCCGGC
TGTCTGCCGGCCTGGGTGCCGGCTCCTGCAGGCTGGGATCTGCTGGCGGCCTGGGCAGCACCCTCGGG
GGTAGCAGCTACTCCAGCTGCTACAGCTTTGGCTCTGGTGGTGGCTATGGCAGCAGCTTTGGGGGTGTT
GATGGGCTGCTGGCTGGAGGTGAGAAGGCCACCATGCAGAACCTCAATGACCGCCTGGCCTCCTACCT
GGACAAGGTGCGTGCCCTGGAGGAGGCCAACACTGAGCTGGAGGTGAAGATCCGTGACTGGTACCAG
AGGCAGGCCCCGGGGCCCGCCCGTGACTACAGCCAGTACTACAGGACAATTGAGGAGCTGCAGAACA
AGATCCTCACAGCCACCGTGGACAATGCCAACATCCTGCTACAGATTGACAATGCCCGTCTGGCTGCT
GATGACTTCCGCACCAAGTTTGAGACAGAGCAGGCCCTGCGCATGAGTGTGGAGGCCGACATCAATGG
CCTGCGCAGGGTGCTGGATGAGCTGACCCTGGCCAGAGCCGACCTGGAGATGCAGATTGAGAACCTC
AAGGAGGAGCTGGCCTACCTGAAGAAGAACCACGAGGAGGAGATGAACGCCCTGCGAGGCCAGGTG
GGTGGTGAGATCAATGTGGAGATGGACGCTGCCCCAGGCGTGGACCTGAGCCGCATCCTCAACGAGA
TGCGTGACCAGTATGAGAAGATGGCAGAGAAGAACCGCAAGGATGCTGAGGATTGGTTCTTCAGCAA
GACAGAGGAACTGAACCGCGAGGTGGCCACCAACAGTGAGCTGGTGCAGAGTGGCAAGAGTGAGATC
TCGGAGCTCCGGCGCACCATGCAGGCCTTGGAGATAGAGCTGCAGTCCCAGCTCAGCATGAAAGCATC
CCTGGAGGGCAACCTGGCGGAGACAGAGAACCGCTACTGCGTGCAGCTGTCCCAGATCCAGGGGCTG
ATTGGCAGCGTGGAGGAGCAGCTGGCCCAGCTTCGCTGCGAGATGGAGCAGCAGAACCAGGAATACA
AAATCCTGCTGGATGTGAAGACGCGGCTGGAGCAGGAGATTGCCACCTACCGCCGCCTGCTGGAGGG
AGAGGATGCCCACCTGACTCAGTACAAGAAAGAACCGGTGACCACCCGTCAGGTGCGTACCATTGTG
GAAGAGGTCCAGGATGGCAAGGTCATCTCCTCCCGCGAGCAGGTCCACCAGACCACCCGCTGAGGAC
TCAGCTACCCCGGCCGGCCACCCAGGAGGCAGGGAGCAGCCGCCCCATCTGCCCCACAGTCTCCGGCC
TCTCCAGCCTCAGCCCCCTGCTTCAGTCCCCTTCCCCATGCTTCCTTGCCTGATGACAATAAAGCTTGTTG
ACTCAGCTAAAAAAAAAAAAAAA

TABLE 1I: CYTOKERATIN 8 POLYNUCLEOTIDE SEQUENCE HOMO SAPIENS
(see, e.g., Accession No. NM_902273) (SEQ ID NO: 13)

ATTCCTGAGAGCTCTCCTCACCAAGAAGCAGCTTCTCCGCTCCTTCTAGGATCTCCGCCTGGTTCGGCC
CGCCTGCCTCCACTCCTGCCTCTACCATGTCCATCAGGGTGACCCAGAAGTCCTACAAGGTGTCCACCT
CTGGCCCCCGGGCCTTCAGCAGCCGCTCCTACACGAGTGGGCCCGGTTCCCGCATCAGCTCCTCGAGC
TTCTCCCGAGTGGGCAGCAGCAACTTTCGCGGTGGCCTGGGCGGCGGCTATGGTGGGGCCAGCGGCAT
GGGAGGCATCACCGCAGTTACGGTCAACCAGAGCCTGCTGAGCCCCCTTGTCCTGGAGGTGGACCCCA
ACATCCAGGCCGTGCGCACCCAGGAGAAGGAGCAGATCAAGACCCTCAACAACAAGTTTGCCTCCTTC
ATAGACAAGGTACGTTCCTGGAGCAGCAGAACAAGATGCTGGAGACAAAGTGGAGCCTCCTGCAGC
AGCAGAAGACGGCTCGAAGCAACATGGACAACATGTTCGAGAGCTACATCAACAACCTTAGGCGGCA
GCTGGAGACTCTGGGCCAGGAGAAGCTGAAGCTGGAGGCGGAGCTTGGCAACATGCAGGGGCTGGTG
GAGGACTTCAAGAACAAGTATGAGGATGAGATCAATAAGCGTACAGAGATGGAGAACGAATTTGTCC
TCATCAAGAAGGATGTGGATGAAGCTTACATGAACAAGGTAGAGCTGGAGTCTCGCCTGGAAGGGCT
GACCGACGAGATCAACTTCCTCAGGCAGCTATATGAAGAGGAGATCCGGGAGCTGCAGTCCCAGATCT

TABLE 1-continued

```
CGGACACATCTGTGGTGCTGTCCATGGACAACAGCCGCTCCCTGGACATGGACAGCATCATTGCTGAG
GTCAAGGCACAGTACGAGGATATTGCCAACCGCAGCCGGGCTGAGGCTGAGAGCATGTACCAGATCA
AGTATGAGGAGCTGCAGAGCCTGGCTGGGAAGCACGGGGATGACCTGCGGCGCACAAAGACTGAGAT
CTCTGAGATGAACCGGAACATCAGCCGGCTCCAGGCTGAGATTGAGGGCCTCAAAGGCCAGAGGGCT
TCCCTGGAGGCCGCCATTGCAGATGCCGAGCAGCGTGGAGAGCTGGCCATTAAGGATGCCAACGCCA
AGTTGTCCGAGCTGGAGGCCGCCCTGCAGCGGGCCAAGCAGGACATGGCGCGGCAGCTGCGTGAGTA
CCAGGAGCTGATGAACGTCAAGCTGGCCCTGGACATCGAGATCGCCACCTACAGGAAGCTGCTGGAG
GGCGAGGAGAGCCGGCTGGAGTCTGGGATGCAGAACATGAGTATTCATACGAAGACCACCAGCGGCT
ATGCAGGTGGTCTGAGCTCGGCCTATGGGGGCCTCACAAGCCCCGGCCTCAGCTACGACCTGGGCTCC
AGCTTTGGCTCTGGCGCGGGCTCCAGCTCCTTCAGCCGCACCAGCTCCTCCAGGGCCGTGGTTGTGAA
GAAGATCGAGACACGTGATGGGAAGCTGGTGTCTGAGTCCTCTGACGTCCTGCCCAAGTGAACAGCTG
CGGCAGCCCCTCCCAGCCTACCCCTCCTGCGCTGCCCCAGAGCCTGGGAAGGAGGCCGCTATGCAGGG
TAGCACTGGGAACAGGAGACCCACCTGAGGCTCAGCCCTAGCCCTCAGCCCACCTGGGGAGTTTACTA
CCTGGGGACCCCCCTTGCCCATGCCTCCAGCTACAAAACAATTCAATTGCTTTTTTTTTTGGTCCAAA
ATAAAACCTCAGCTAGCTCTGCCAATGTC
```

TABLE 1J: CYTOKERATIN 18 POLYNUCLEOTIDE SEQUENCE HOMO SAPIENS
(see, e.g., Accession No. NM_199187)(SEQ ID NO: 14)

```
GCAGCCTCGAGGGCCAACAACACCTGCTGTCCGTGTCCATGGCCGGTTGGCCACCCCGTTTCTGGGGG
CATGAGCTTCACCACTCGCTCACCTTCTCCACCAACTACCGGTCCCTGGCTCTGTCCAGGCGCCCAG
CTACGGCGCCCGGCCGGTCAGCAGCGCGGCCAGCGTCTATGCAGGCGCTGGGGGCTCTGGTTCCCGGA
TCTCCGTGTCCCGCTCCACCAGCTTCAGGGGCGGCATGGGGTCCGGGGGCCTGGCCACCGGGATAGCC
GGGGGTCTGGCAGGAATGGGAGGCATCCAGAACGAGAAGGAGACCATGCAAAGCCTGAACGACCGC
CTGGCCTCTTACCTGGACAGAGTGAGGAGCCTGGAGACCGAGAACCGGAGGCTGGAGAGCAAAATCC
GGGAGCACTTGGAGAAGAAGGGACCCCAGGTCAGAGACTGGAGCCATTACTTCAAGATCATCGAGGA
CCTGAGGGCTCAGATCTTCGCAAATACTGTGGACAATGCCCGCATCGTTCTGCAGATTGACAATGCCC
GTCTTGCTGCTGATGACTTTAGAGTCAAGTATGAGACAGAGCTGGCCATGCGCCAGTCTGTGGAGAAC
GACATCCATGGGCTCCGCAAGGTCATTGATGACACCAATATCACGACTGCAGCTGGAGACAGAGAT
CGAGGCTCTCAAGGAGGAGCTGCTCTTCATGAAGAAGAACCACGAAGAGGAAGTAAAAGGCCTACAA
GCCCAGATTGCCAGCTCTGGGTTGACCGTGGAGGTAGATGCCCCAAATCTCAGGACCTCGCCAAGAT
CATGGCAGACATCCGGGCCCAATATGACGAGCTGGCTCGGAAGAACCGAGAGGAGCTAGACAAGTAC
TGGTCTCAGCAGATTGAGGAGAGCACCACAGTGGTCACCACAGCTGCTGAGGTTGGAGCTGCTGA
GACGACGCTCACAGAGCTGAGACGTACAGTCCAGTCCTTGGAGATCGACCTGGACTCCATGAGAAATC
TGAAGGCCAGCTTGGAGAACAGCCTGAGGGAGGTGGAGGCCCGCTACGCCCTACAGATGGAGCAGCT
CAACGGGATCCTGCTGCACCTTGAGTCAGAGCTGGCACAGACCCGGGCAGAGGGACAGCGCCAGGCC
CAGGAGTATCTAGCCCTGCTGAACATCAAGGTCAAGCTGGAAGGTGAGATCGCCACCTACCGCCGCCT
GCTGGAAGATGGCGAGGACTTTAATCTTGGTGATGCCTTGGACAGCGCAACTCCATGCAAACCATCC
AAAAGACCACCACCGGCCGGATAGTGGATGGCAAAGTGGTGTCTGAGACCAATGACACCAAAGTTCT
GAGGCATTAAGCCAGCAGAAGCAGGGTACCCTTTGGGGAGCAGGAGGCCAATAAAAAGTTCAGAGTT
CAAAAAAAAAAAAAAAAAAA
```

TABLE 1K: c-SRC POLYNUCLEOTIDE SEQUENCE HOMO SAPIENS
(see, e.g., Accession No.: NM_004383)(SEQ ID NO: 15)

```
TCCGGGCGGCCCCCGGCAGCCAGCGCGACGTTCCAAAATCGAACCTCAGTGGCGGCGCTCGGAAGC
GGAACTCTGCCGGGGCCGCGCCGGCTACATTGTTTCCTCCCCCCGACTCCCTCCCGCCCCCTTCCCCCG
CCTTTCTTCCCTCCGCGACCCGGGCCGTGCGTCCGTCCCCCTGCCTCTGCCTGGCGGTCCCTCCTCCCCT
CTCCTTGCACCCCATACCTCTTTGTACCGCACCCCCTGGGGACCCCTGCGCCCCTCCCCTCCCCCCTGAC
CGCATGGACCGTCCCGCAGGCCGCTGATGCCGCCCGCGGCGAGGTGGCCCGGACCGCAGTGCCCCAA
GAGAGCTCTAATGGTACCAAGTGACAGGTTGGCTTTACTGTGACTCGGGGACGCCAGAGCTCCTGAGA
AGATGTCAGCAATACAGGCCGCCTGGCCATCCGGTACAGAATGTATTGCCAAGTACAACTTCCACGGC
ACTGCCGAGCAGGACCTGCCCTTCTGCAAAGGAGACGTGCTCACCATTGTGGCCGTCACCAAGGACCC
CAACTGGTACAAAGCCAAAAACAAGGTGGGCCGTGAGGGCATCATCCCAGCCAACTACGTCCAGAAG
CGGGAGGGCGTGAAGGCGGGTACCAAACTCAGCCTCATGCCTTGGTTCCACGGCAAGATCACACGGG
AGCAGGCTGAGCGGCTTCTGTACCCGCCGAGACAGGCCTGTTCCTGGTGCGGGAGAGCACCAACTAC
CCCGGAGACTACACGCTGTGCGTGAGCTGCGACGGCAAGGTGGAGCATACCGCATCATGACCATGC
CAGCAAGCTCAGCATCGACGAGGAGGTGTACTTTGAGAACCTCATGCAGCTGGTGGAGCACTACACCT
CAGACGCAGATGGACTCTGTACGCGCCTCATTAAACCAAAGGTCATGGAGGGCACAGTGGCGGCCCA
GGATGAGTTCTACCGCAGCGGCTGGGCCCTGAACATGAAGGAGCTGAAGCTGCTGCAGACCATCGGG
AAGGGGGAGTTCGGAGACGTGATGCTGGGCGATTACCGAGGGAACAAAGTCGCCGTCAAGTGCATTA
AGAACGACGCCACTGCCCAGGCCTTCCTGGCTGAAGCCTCAGTCATGACGCAACTGCGGCATAGCAAC
CTGGTCAGCTCCTGGGCGTGATCGTGGAGGAGAAGGGCGGGCTCTACATCGTCACTGAGTACATGGC
CAAGGGGAGCCTTGTGACTACCTGCGGCTCTAGGGGTCGGTCAGTGCTGGGCGGAGACTGTCTCCTCA
AGTTCTCGCTAGATGTCTGCGAGGCCATGGAATACCTGGAGGGCAACAATTTCGTGCATCGAGACCTG
GCTGCCCGCAATGTGCTGGTGTCTGAGGACAACGTGGCCAAGGTCAGCGACTTTGGTCTCACCAAGGA
GGCGTCCAGCACCCAGGACACGGGCAAGCTGCCAGTCAAGTGGACAGCCCCTGAGGCCCTGAGAGAG
AAGAAATTCTCCACTAAGTCTGACGTGTGGAGTTTCGGAATCCTTCTCTGGGAAATCTACTCCTTTGGG
CGAGTGCCTTATCCAAGAATTCCCCTGAAGGACGTCGTCCCTCGGGTGGAGAAGGGCTACAAGATGGA
TGCCCCCGACGGCTGCCCGCCCGCAGTCTATGAAGTCATGAAGAACTGCTGGCACCTGGACGCCGCCA
TGCGGCCCTCCTTCCTACAGCTCCGAGAGCAGCTTGAGCACATCAAAACCCACGAGCTGCACCTGTGA
CGGCTGGCCTCTGGGTCATGGGCTGTGTGGGACTGAACCTGGAAGATCATGGACCTGGTGCCCC
TGCTCACTGGGCCCGAGCCTGAACTGAGCCCCAGCTGGCGGGCCTTTTTCCTGCGTCCCAGCCT
GCACCCCTCCGGCCCCGTCTCTCTTGGACCCACCTGTGGGGCCTGGGGAGCCCACTGAGGGGCCAGGG
AGGAAGGAGGCCACGGAGCGGGCGGCAGCGCCCCACCACGTCGGGCTTCCCTGGCCTCCCGCCACTC
GCCTTCTTAGAGTTTTATTCCTTTCCTTTTTTGAGATTTTTTTTCCGTGTGTTTATTTTTTATTATTTTTCA
AGATAAGGAGAAAGAAAGTACCCAGCAAATGGGCATTTTACAAGAAGTACGAATCTTATTTTTCCTGT
CCTGCCCGTGAGGTGGGGGGGACCGGGCCCCTCTCTAGGGACCCCTCGGCCCAGCCTCATTCCCCATT
```

TABLE 1-continued

CTGTGTCCCATGTCCCGTGTCTCCTCGGTCGCCCCGTGTTTGCGCTTGACCATGTTGCACTGTTTGCATG
GGCCCGAGGCAGACGTCTGTCAGGGGCTTGGATTTCGTGTGGCGCTGCCACCCGCCCACCCGCCTTGT
GAGATGGAATCGTAATAAACCACGCCATGAGGAAAAAA

TABLE 1L: c-abl POLYNUCLEOTIDE SEQUENCE *HOMO SAPIENS*
(see, e.g., Accession No. X16416)(SEQ ID NO: 16)

CGCGGCCGCCCTGGGCGGGCGCGGGCGGCGGGCGGCGGTGAGGGCGGCCTGCGGGGCGGCGCCCGGG
GGCCGGGCCGAGCCGGGCCTGAGCCGGGCCCGGACCGAGCTGGGAGAGGGGCTCCGGCCCGATCGTT
CGCTTGGCGCAAAATGTTGGAGATCTGCCTGAAGCTGGTGGGCTGCAAATCCAAGAAGGGGCTGTCCT
CGTCCTCCAGCTGTTATCTGGAAGAAGCCCTTCAGCGGCCAGTAGCATCTGACTTTGAGCCTCAGGGTC
TGAGTGAAGCCGCTCGTTGGAACTCCAAGGAAAACCTTCTGCTGGACCCAGTGAAAATGACCCCAAC
CTTTTCGTTGCACTGTATGATTTTGTGGCCAGTGGAGATAACACTCTAAGCATAACTAAAGGTGAAAA
GCTCCGGGTCTTAGGCTATAATCACAATGGGGAATGGTGTGAAGCCCAAACCAAAATGGCCAAGGC
TGGGTCCCAAGCAACTACATCACGCCAGTCAACAGTCTGGAGAAACACTCCTGGTACCATGGGCCTGT
GTCCCGCAATGCCGCTGAGTATCTGCTGAGCAGCGGGATCAATGGCAGCTTCTTGGTGCGTGAGAGTG
AGAGCAGTCCTGGCCAGAGGTCCATCTCGCTGAGATACGAAGGGAGGGGTGTACCATTACAGGATCAA
CACTGCTTCTGATGGCAAGCTCTACGTCTCCTCCGAGAGCCGCTTCAACACCCTGGCCGAGTTGGTTCA
TCATCATTAACGGTGGCCGACGGGCTCATCACCACGCTCCATTATCCAGCCCAAAGCGCAACAAGC
CCACTGTCTATGGTGTGTCCCCCAACTACGACAAGTGGGAGATGGAACGCACGGACATCACCATGAAG
CACAAGCTGGGCGGGGGCCAGTACGGGGAGGTGTACGAGGGCGTGTGGAAGAAATACAGCCTGACGG
TGGCCGTGAAGACCTTGAAGGAGGACACCATGGAGGTGGAAGAGTTCTTGAAAGAAGCTGCAGTCAT
GAAAGAGATCAAACACCCTAACCTGGTGCAGCTCCTTGGGGTCTGCACCCGGGAGCCCCCGTTCTATA
TCATCACTGAGTTCATGACCTACGGGAACCTCCTGGACTACCTGAGGGAGTGCAACCGGCAGGAGGTG
AACGCCGTGGTGCTGCTGTACATGGCCACTCAGATCTCGTCAGCCATGGAGTACCTGGAGAAGAAAAA
CTTCATCCACAGAGATCTTGCTGCCCGAAACTGCCTGGTAGGGGAGAACCACTTGGTGAAGGTAGCTG
ATTTTGGCCTGAGCAGGTTGATGACAGGGGACACCTACACAGCCCATGCTGGAGCCAAGTTCCCCATC
AAATGGACTGCACCCGAGAGCCTGGCCTACAACAAGTTCTCCATCAAGTCCGACGTCTGGGCATTTGG
AGTATTGCTTTGGGAAATTGCTACCTATGGCATGTCCCCTTACCCGGGAATTGACCTGTCCCAGGTGTA
TGAGCTGCTAGAGAAGGACTACCGCATGGAGCGCCCAGAAGGCTGCCCAGAGAAGGTCTATGAACTC
ATGCGAGCATGTTGGCAGTGGAATCCCTCTGACCGGCCCTCCTTTGCTGAAATCCACCAAGCCTTTGAA
ACAATGTTCCAGGAATCCAGTATCTCAGACGAAGTGGAAAAGGAGCTGGGGAAACAAGGCGTCCGTG
GGGCTGTGAGTACCTTGCTGCAGGCCCCAGAGCTGCCCACCAAGACGAGGACCTCCAGGAGAGCTGC
AGAGCACAGAGACACCACTGACGTGCCTGAGATGCCTCACTCCAAGGGCCAGGGAGAGAGCGATCCT
CTGGACCATGAGCCTGCCGTGTCTCCATTGCTCCCTGAAAAGAGCGAGGTCCCCCGGAGGGCGGCCT
GAATGAAGATGAGCGCCTTCTCCCCAAAGACAAAAGACCAACTTGTTCAGCGCCTTGATCAAGAAG
AAGAAGAAGACAGCCCCAACCCCTCCCAAACGCAGCAGCTCCTTCCGGGAGATGGACGGCCAGCCGG
AGCGCAGAGGGCCGGCGAGGAAGAGGGCCGAGACATCCAACAACGGGGCACTGGCTTTCACCCCCGTT
GGACACAGCTGACCCAGCCAAGTCCCCAAAGCCCAGCAATGGGGCTGGGGTCCCCAATGGAGCCCTC
CGGGAGTCCGGGGGCTCAGGCTTCCGGTCTCCCCACCTGTGGAAGAAGTCCAGCACGCTGACCAGCAG
CCGCCTAGCCACCGGCGAGGAGGAGGGCGGTGGCAGCTCCAGCAAGCGCTTCCTGCGCTCTTGCTCCG
CCTCCTGCGTTCCCCATGGGGCCAAGGACACGGAGTGGAGGTCAGTCACGCTGCCTCTGGGACTTGCAG
TCCACGGGAAGACAGTTTGACTCGTCCACATTTGGAGGGCACAAAAAGTGAGAAGCCGGCTCTGCCTCG
GAAGAGGGCAGGGAGAACAGGTCTGACCAGGTGACCCGAGGCACAGTAACGCCTCCCCCCAGGCTG
GTGAAAAAGAATGAGGAAGCTGCTGATGAGGTCTTCAAAGACATCATGGAGTCCAGCCCGGGCTCCA
GCCCGCCCAACCTGACTCCAAAACCCCTCCGGCGGCAGGTCAGCCCCTGCCTCGGGCGC
CACAAGGAAGAAGCTGAAAAGGGCAGTGCCTTAGGGACCCCTGCTGCAGCTGAGCCAGTGACCCCCA
CCAGCAAAGCAGGCTCAGGTGCACCAGGGGGCACCAGCAAGGGCCCCGCCGAGGAGTCCAGAGTGAG
GAGGCACAAGCACTCCTCTGAGTCGCCAGGGAGGGACAAGGGGAAATTGTCCAGGCTCAAACCTGCC
CCGCCGCCCCCACCAGCAGCCTCTGCAGGGAAGGCTGGAGGAAAGCCCTCGCAGAGCCCGAGCCAGG
AGGCGGCCGGGGAGGCAGTCCTGGGCGCAAAGACAAAAGCCACGAGTCTGGTTGATGCTGTGAACAG
TGACGCTGCCAAGCGCAGCCAGCCGGGAGAGGGCCTCAAAAAGCCCGTGCTCCCGGCCACTCCAAAG
CCACAGTCGGCCAAGCCGTCGGGGACCCCCATCAGCCGAGCCCCCGTTCCCTCCACGTTGCCATCAGC
ATCCTCGGCCCTGGCAGGGACCAGCCGTCTTCCACTGCCTTCATCCCTCTCATATCAACCCGAGTGTC
TCTTCGGAAAACCCGCCAGCCTCCAGAGCGGATCGCCAGCGGCGCCATCACCAAGGGCGTGGTCCTGG
ACAGCACCGAGGCGCTGTGCCTCGCCATCTCTAGGAACTCCGAGCAGATGGCCAGCCACAGCGCAGTG
CTGGAGGCCGGCAAAAACCTCTACACGTTCTGCGTGAGCTATGTGGATTCCATCCAGCAAATGAGGAA
CAAGTTTGCCTTCCGAGAGGCCATCAACAAACTGGAGAATAATCTCCGGGAGCTTCAGATCTGCCCGG
CGAGAGCAGGCAGTGGTCCGGCGGCCACTCAGGACTTCAGCAAGCTCCTCAGTTCGGTGAAGGAAATC
AGTGACATAGTGCAGAGGTAGCAGCAGTCAGGGTCAGGTGTCAGGCCCGTCGGAGCTGCCTGCAGC
ACATGCGGGCTCGCCCATACCCATGACAGTGGCTGACAAGGGACTAGTGAGTCAGCACCTTGGCCCAG
GAGCTCTGCGCCAGGCAGAGCTGAGGGCCCTGTGGAGTCCAGCTCTACTACCTACGTTTGCACCGCCT
GCCCTCCCGCACCTTCCTCCTCCCCGCTCCGTCTCTGTCCTCGAATTTTATCTGTGGAGTTCCTGCTCCG
TGGACTGCAGTCGGCATGCCAGGACCCGCCAGCCCCGCTCCCACCTAGTGCCCCAGACTGAGCTCTCC
AGGCCAGGTGGGAACGGCTGATGTGGACTGTCTTTTTCATTTTTTTCTCTGGAGCCCCTCCTCCCCC
GGCTGGGCCTCCTTCTTCCACTTCTCCAAGAATGGAAGCCTGAACTGAGGCCTTGTGTGCAGGCCCTC
TGCCTGCACTCCCTGGCCTTGCCCGTCGTGTGCTGAAGACATGTTTCAAGAACCGCCATTTCGGGAGG
GCATGCACGGGCCATGGACACGGCTGGTCACTCTGCCCTCTGGTGCTGCCCGGGTGGGGTGCACTCG
CCATTTCCTCACGTGCAGGACAGCTCTTGATTTGGGTGGAAAACAGGGTGCTAAAGCCAACCAGCCTT
TGGGTCCTGGGCAGGTGGGAGCTGAAAAGGATCGAGGCATGGGGCATGTCCTTTCCATCGTCCACAT
CCCCAGAGCCCAGCTCTTGCTCTCTTGTGACGTGCACTGTGACCTTCTGGCAAGAAAGCTTGAGTCTCAA
GGGTGGCAGGTCACTGTCACTGCCGACATCCCTCCCCCAGCAGAATGGAGGCAGGGGACAAGGGAGG
CAGTGGCTAGTGGGGTGAACAGCTGGTGCCAAATAGCCCCAGACTGGGCCCAGGCAGGTCTGCAAGG
GCCCAGAGTGAACCGTCCTTTCACACATCTGGGTGCCCTGAAGGGCCTTCCCCTCCCCACTCCTCTA
AGACAAAGTAGATTCTTACAGGCCCCTTTCCTTTGGAACAAGCAACAGCCTTCACTTTTCTGAGTTCTTGA
AGCATTTCAAAGCCCTGCCTCTGTGTAGCCGCCCTGAGAGAATAGAGCTGCCACTGGGCACCTCGC
GACAGGTGGGAGGAAAGGGCCTGCGCAGTCCTGGTCCTGGCTGCACTCTTGAACTGGGCGAATGTCTT
ATTTAATTACCGTGAGTGACATAGCCTCATGTTCTGTGGGGTCATCAGGGAGGGTTAGGAAAACCAC
AAACGGAGCCCCTGAAAGCCTCACGTATTTCACAGAGACACGCCTGCCATCTTCTCCCCGAGGCTGCCC
CAGGCCGGAGCCCAGATACCGGCGGGCTGTGACTCTGGGCAGGGACCCGGGGTCTCCTGGACCTTGAC

TABLE 1-continued

```
AGAGCAGCTAACTCCGAGAGCAGTGGGCAGGTGGCCGCCCCTGAGGCTTCACGCCGGAGAAGCCACC
TTCCCGCCCCTTCATACCGCCTCGTGCCAGCAGCCTCGCACAGGCCCTAGCTTTACGCTCATCACCTAA
ACTTGTACTTTATTTTTCTGATAGAAATGGTTTCCTCTGGATCGTTTTATGCGGTTCTTACAGCACATCA
CCTCTTTCCCCCCGACGGCTGTGACGCAGCGGAGAGGCACTAGTCACCGACAGCGGCCTTGAAGACAG
AGCAAAGCCCCACCCAGGTCCCCCGACTGCCTGTCTCCATGAGGTACTGGTCCCTTCCTTTTGTTAAC
GTGATGTGCCACTATATTTTACACGTATCTCTTGGTATGCATCTTTTATAGACGCTCTTTTCTAAGTGGC
GTGTGCATAGCGTCCTGCCCTGCCCTCGGGGCCTGTGGTGGCTCCCCCTCTGCTTCTCGGGGTCCAGT
GCATTTTGTTTCTGTATATGATTCTCTGTGGTTTTTTTTGAATCCAAATCTGTCCTCTGTAGTATTTTTTA
AATAAATCAGTGTTTACATTAG
```

What is claimed:

1. A method for determining the responsiveness of a mammalian breast tumor cell to treatment with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof, the method comprising determining the level of expression of yes-associated protein 1 in a biological sample comprising a breast tumor cell; and correlating a finding of elevated expression of yes-associated protein 1, as compared to the level of expression of a control, with said breast tumor cell being sensitive to said treatment with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof.

2. The method of claim 1 further comprising determining the level of expression of the caveolin-1 gene.

3. The method of claim 1 further comprising determining the level of expression of the moesin gene.

4. The method of claim 1 further comprising determining the level of expression of the caveolin-1 gene and the moesin gene.

5. The method of claim 1 wherein the breast tumor cell is a basal cell, a luminal cell, a mesenchymal cell, a cell having a mutation in the BRCA1 gene, a cell that has undergone an epithelial to mesenchymal transition, or a cell that has reduced expression of an estrogen, progesterone, and HER2 receptor as compared to the level of expression of said estrogen, progesterone, and HER2 receptor in a control cell.

6. The method of claim 1 wherein the level of expression is determined by detecting the level of mRNA transcribed from the yes-associated protein 1 gene.

7. The method of claim 1 wherein the level of expression is determined by detecting the level of cDNA produced from the reverse transcription of the mRNA transcribed from the yes-associated protein 1 gene.

8. The method of claim 1 wherein the level of expression is determined by detecting the level of the polypeptide encoded by the yes-associated protein 1 gene.

9. A method for determining the responsiveness of an individual with breast cancer to treatment with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof, comprising:

obtaining a biological sample comprising a breast tumor cell from said individual; and determining the level of expression in said biological sample comprising a breast tumor cell of yes-associated protein 1; and correlating a finding of elevated expression of yes-associated protein 1, as compared to the level of expression of a control, with said breast tumor cell being sensitive to said treatment with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt, solvate, or hydrate thereof.

10. The method of claim 9 further comprising determining the level of expression of the moesin gene.

11. The method of claim 9 further comprising determining the level of expression of the caveolin-1 gene.

12. The method of claim 9 further comprising determining the level of expression of the caveolin-1 gene and the moesin gene.

13. The method of claim 9 wherein the level of expression is determined by detecting the level of mRNA transcribed from the yes-associated protein 1 gene.

14. The method of claim 9 wherein the level of expression is determined by detecting the level of cDNA produced from the reverse transcription of the mRNA transcribed from the yes-associated protein 1 gene.

15. The method of claim 9 wherein the level of expression is determined by detecting the level of the polypeptide encoded by the yes-associated protein 1 gene.

* * * * *